(12) United States Patent
Lim et al.

(10) Patent No.: US 9,406,890 B2
(45) Date of Patent: *Aug. 2, 2016

(54) COMPOUND AND ORGANIC LIGHT-EMITTING DIODE INCLUDING THE SAME

(71) Applicants: Jin-O Lim, Yongin (KR); Seok-Hwan Hwang, Yongin (KR); Young-Kook Kim, Yongin (KR); Jun-Ha Park, Yongin (KR); Hye-Jin Jung, Yongin (KR); Eun-Young Lee, Yongin (KR); Sang-Hyun Han, Yongin (KR); Eun-Jae Jeong, Yongin (KR); Soo-Yon Kim, Yongin (KR); Jong-Hyuk Lee, Yongin (KR)

(72) Inventors: Jin-O Lim, Yongin (KR); Seok-Hwan Hwang, Yongin (KR); Young-Kook Kim, Yongin (KR); Jun-Ha Park, Yongin (KR); Hye-Jin Jung, Yongin (KR); Eun-Young Lee, Yongin (KR); Sang-Hyun Han, Yongin (KR); Eun-Jae Jeong, Yongin (KR); Soo-Yon Kim, Yongin (KR); Jong-Hyuk Lee, Yongin (KR)

(73) Assignee: SAMSUNG DISPLAY CO., LTD., Yongin, Gyeonggi-do (KR)

( * ) Notice: Subject to any disclaimer, the term of this patent is extended or adjusted under 35 U.S.C. 154(b) by 412 days.

This patent is subject to a terminal disclaimer.

(21) Appl. No.: 13/933,213

(22) Filed: Jul. 2, 2013

(65) Prior Publication Data
US 2014/0252323 A1 Sep. 11, 2014

(30) Foreign Application Priority Data

Mar. 5, 2013 (KR) .......................... 10-2013-0023565

(51) Int. Cl.
*H01L 51/00* (2006.01)
*H01L 27/32* (2006.01)
(Continued)

(52) U.S. Cl.
CPC .......... *H01L 51/0058* (2013.01); *C07D 209/56* (2013.01); *H01L 51/0072* (2013.01); *H01L 51/006* (2013.01); *H01L 51/0059* (2013.01); *H01L 51/5012* (2013.01)

(58) Field of Classification Search
None
See application file for complete search history.

(56) References Cited

U.S. PATENT DOCUMENTS 7,053,255 B2 5/2006 Ikeda et al.
7,233,019 B2 6/2007 Ionkin et al.
(Continued)

FOREIGN PATENT DOCUMENTS

JP 2009-215333 A 9/2009
KR 10-2006-0006760 A 1/2006

OTHER PUBLICATIONS

Aldrich; 4H-Benzo[def]Carbazole [Name of Reagents]; www.sigmaaldrich.com.
(Continued)

*Primary Examiner* — J. L. Yang
(74) *Attorney, Agent, or Firm* — Lee & Morse, P.C.

(57) ABSTRACT

An embodiment is directed to compound represented by Formula 1 below:

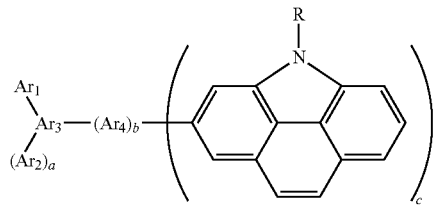

<Formula 1> wherein, in Formula 1,
$Ar_1, Ar_2, Ar_3$, and $Ar_4$ are each independently a substituted or unsubstituted $C_6$-$C_{60}$ aryl group, a substituted or unsubstituted $C_{10}$-$C_{60}$ condensed polycyclic group, or a substituted or unsubstituted $C_3$-$C_{60}$ heteroaryl group;
a is an integer from 0 to 2,
b is an integer from 0 to 4,
c is an integer from 1 to 3, and
when b is 2 or more, $Ar_4$ is identical to or different from each other.

19 Claims, 1 Drawing Sheet

(51) Int. Cl.
 *H01L 51/50* (2006.01)
 *C07D 209/56* (2006.01)

(56) References Cited

U.S. PATENT DOCUMENTS 7,429,372 B2   9/2008   Pez et al.

2005/0156164 A1   7/2005   Sotoyama
2014/0124747 A1*  5/2014   Hwang ............... H01L 51/0061
                                                  257/40

OTHER PUBLICATIONS

A Novel Conjugated Polymer Based on 4H-Benzo[def]Carbazole Backbone for OLED; 2009 Fall Assembly and Symposium. vol. 34, No. 2, 2009.

* cited by examiner

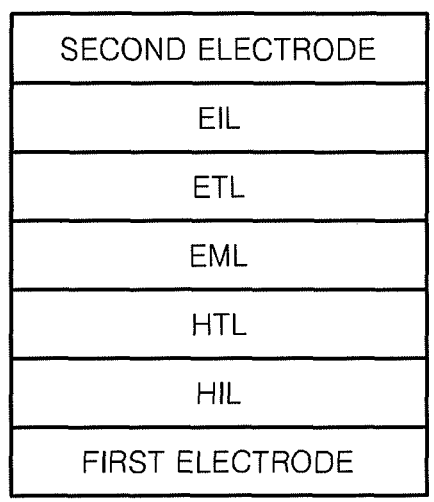

COMPOUND AND ORGANIC LIGHT-EMITTING DIODE INCLUDING THE SAME

CROSS-REFERENCE TO RELATED PATENT APPLICATION

This application claims the benefit of and priority under 35 U.S.C. §119 to Korean Patent Application No. 10-2013-0023565, filed on Mar. 5, 2013, in the Korean Intellectual Property Office, and entitled: "COMPOUND AND ORGANIC LIGHT-EMITTING DIODE INCLUDING THE SAME," which is incorporated by reference herein in its entirety.

BACKGROUND

1. Field

Embodiments relate to a compound and an organic light-emitting diode including the same.

2. Description of the Related Art

Organic light-emitting diodes (OLEDs), which are self-emitting diodes, have advantages such as wide viewing angles, excellent contrast, quick response, high brightness, and excellent driving voltage, and can provide multicolored images.

SUMMARY

Embodiments are directed to a compound represented by Formula 1 below:

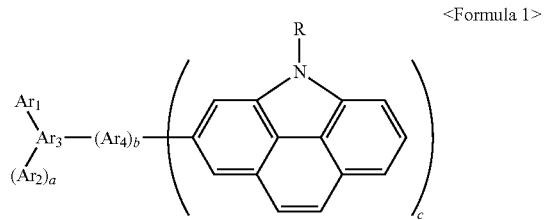

<Formula 1>

In, in Formula 1, $Ar_1$, $Ar_2$, $Ar_3$, $Ar_4$, and R may each independently be a substituted or unsubstituted $C_6$-$C_{60}$ aryl group, a substituted or unsubstituted $C_{10}$-$C_{60}$ condensed polycyclic group, or a substituted or unsubstituted $C_3$-$C_{60}$ heteroaryl group;

a may be an integer from 0 to 2, b may be an integer from 0 to 4, c may be an integer from 1 to 3, and when b is 2 or more, $Ar_4$ may be identical to or different from each other.

$Ar_1$ and $Ar_2$ may each independently be one of the following compounds represented by Formulas 2a to 2e below:

2a

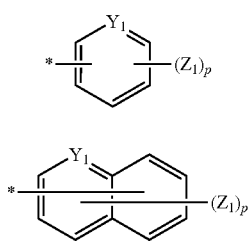

2b

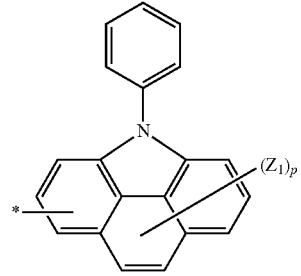

2c

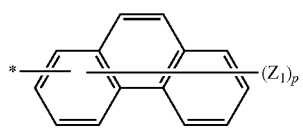

2d

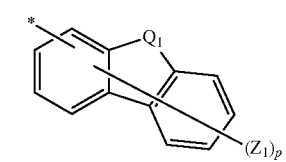

2e

In Formulas 2a to 2e, $Q_1$ may be a group represented by —C($R_{30}$)($R_{31}$)—, —N($R_{32}$)—, —S—, or —O—;

$Y_1$ may be CH or N;

$Z_1$, $R_{30}$, $R_{31}$, and $R_{32}$ may each independently be a hydrogen atom, a deuterium atom, a substituted or unsubstituted $C_1$-$C_{20}$ alkyl group, a substituted or unsubstituted $C_6$-$C_{20}$ aryl group, a substituted or unsubstituted $C_3$-$C_{20}$ heteroaryl group, a substituted or unsubstituted $C_6$-$C_{20}$ condensed polycyclic group, —Si($R_{40}$)$_3$, a halogen atom, a cyano group, a nitro group, a hydroxyl group, or a carboxyl group;

$R_{40}$ may be a substituted or unsubstituted $C_1$-$C_{20}$ alkyl group, a substituted or unsubstituted $C_6$-$C_{20}$ aryl group, a substituted or unsubstituted $C_3$-$C_{20}$ heteroaryl group, or a substituted or unsubstituted $C_6$-$C_{20}$ condensed polycyclic group;

p may be an integer from 1 to 9; and

* is a binding site.

$Ar_3$ may be represented by Formula 3a or Formula 3b below:

3a

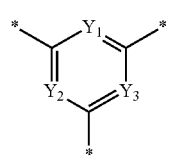

3b

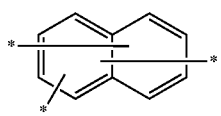

In Formulas 3a and 3b, $Y_1$, $Y_2$, and $Y_3$ may each independently be CH or N, and

* is a binding site.

Ar₄ may be one of the following compounds represented by Formulas 4a to 4f:

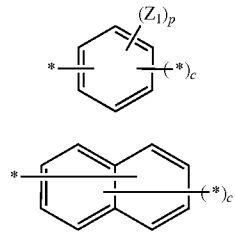

4a

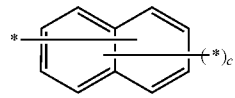

4b

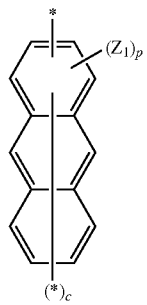

4c

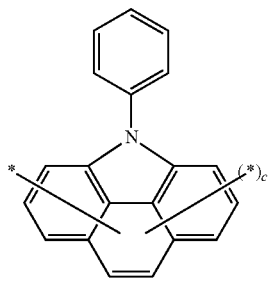

4d

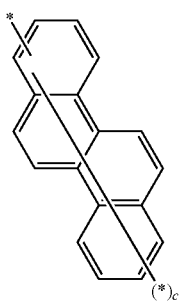

4e

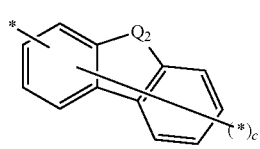

4f

In Formulas 4a to 4f, $Q_2$ may be a group represented by —C($R_{30}$)($R_{31}$)—;

$Z_1$, $R_{30}$, and $R_{31}$ may each independently be a hydrogen atom, a deuterium atom, a substituted or unsubstituted $C_1$-$C_{20}$ alkyl group, a substituted or unsubstituted $C_6$-$C_{20}$ aryl group, a substituted or unsubstituted $C_3$-$C_{20}$ heteroaryl group, a substituted or unsubstituted $C_6$-$C_{20}$ condensed polycyclic group, a halogen atom, a cyano group, a nitro group, a hydroxyl group, or a carboxyl group;

p may be an integer from 1 to 9;

c may be an integer from 1 to 3; and

* is a binding site.

R may be represented by Formula 5a or Formula 5b below:

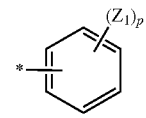

5a

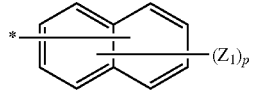

5b

In Formulas 5a and 5b, $Z_1$ may be a hydrogen atom, a deuterium atom, a substituted or unsubstituted $C_1$-$C_{20}$ alkyl group, a substituted or unsubstituted $C_6$-$C_{20}$ aryl group, a substituted or unsubstituted $C_3$-$C_{20}$ heteroaryl group, a substituted or unsubstituted $C_6$-$C_{20}$ condensed polycyclic group, a halogen atom, a cyano group, a nitro group, a hydroxyl group, or a carboxyl group;

p may be an integer from 1 to 7; and

* is a binding site.

The compound of Formula 1 above may be one of the following compounds below:

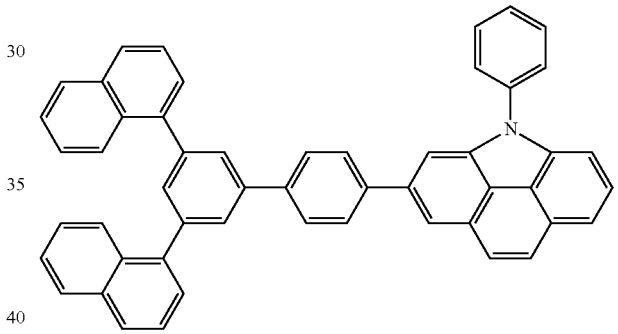

3

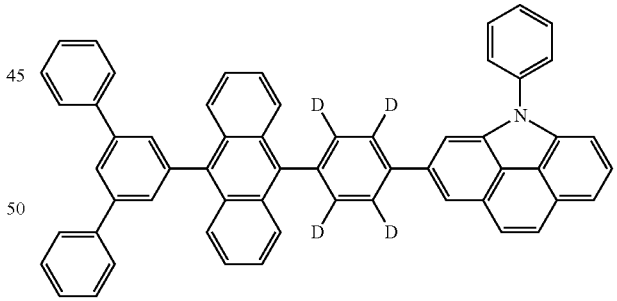

21

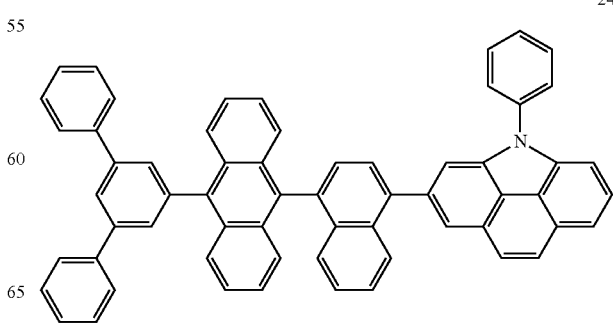

24

27

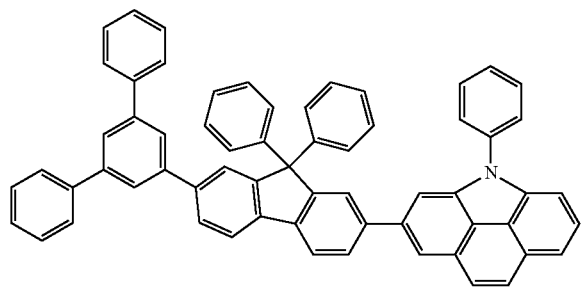

40

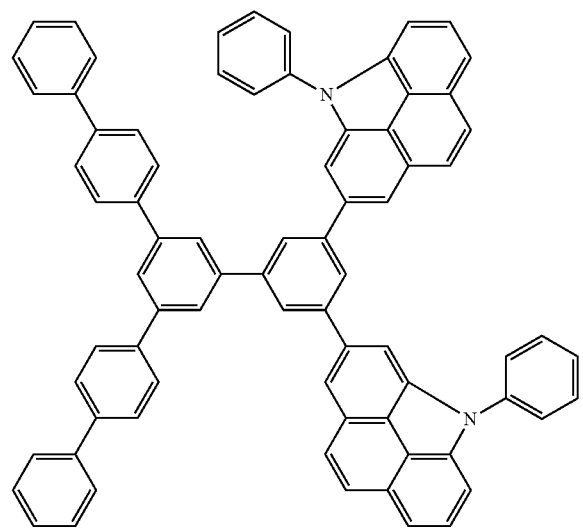

44

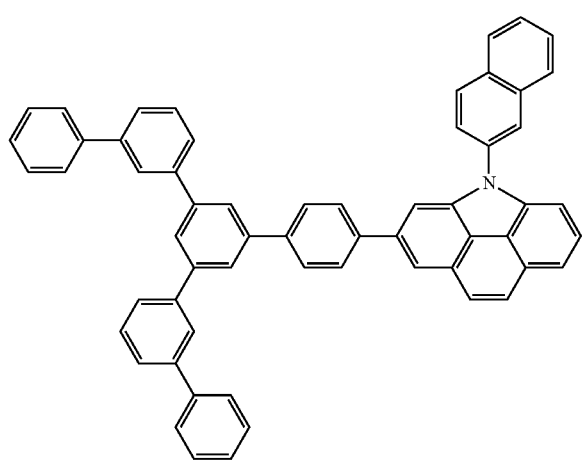

50

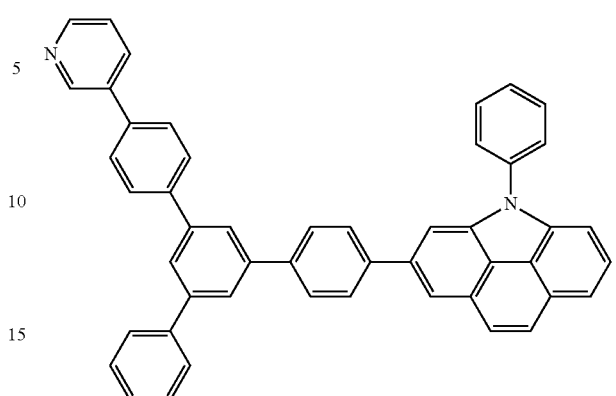

55

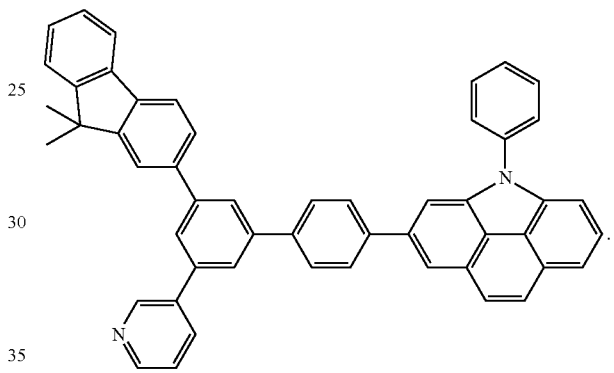

Embodiments are also directed to an organic light-emitting diode (OLED), including a first electrode, a second electrode, and an organic layer that is disposed between the first electrode and the second electrode, and includes a compound according to an embodiment.

The organic layer may be a blue emission layer or an electron transport layer.

The OLED may include a hole injection layer, a hole transport layer, or a functional layer having both hole injection and hole transport capabilities, and an emission layer that includes a compound according to an embodiment, the emission layer further including an anthracene-based compound, an arylamine-based compound, or a styryl-based compound.

The OLED may include a hole injection layer, a hole transport layer, or a functional layer having both hole injection and hole transport capabilities, and an emission layer that includes a compound according to an embodiment. At least one of a red emission layer, a green emission layer, a blue emission layer, and a white emission layer of the emission layer may include a phosphorescent compound.

The hole injection layer, the hole transport layer, or the functional layer having both hole injection and hole transport capabilities may include a charge-generating material.

The charge-generating material may be a p-dopant.

The p-dopant may be a quinone derivative.

The p-dopant may be a metal oxide.

The p-dopant may be a cyano group-containing compound.

The organic layer may include an electron transport layer, and the electron transport layer may include an electron-transporting organic compound and a metal complex.

The metal complex may be a lithium complex.

The metal complex may be lithium quinolate or Compound 203:

<Compound 203>

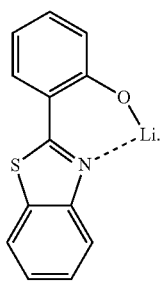

The organic layer may be formed of a compound according to an embodiment by using a wet process.

Embodiments are also directed to a flat panel display device including an OLED according to an embodiment. The first electrode of the OLED may be electrically connected to a source electrode or a drain electrode in a thin film transistor.

BRIEF DESCRIPTION OF THE DRAWING

Features will become apparent to those of skill in the art by describing in detail example embodiments with reference to the attached drawing in which:

FIG. 1 is a schematic view of a structure of an organic light-emitting diode (OLED) according to an embodiment.

DETAILED DESCRIPTION

Example embodiments will now be described more fully hereinafter with reference to the accompanying drawing; however, they may be embodied in different forms and should not be construed as limited to the embodiments set forth herein. Rather, these embodiments are provided so that this disclosure will be thorough and complete, and will fully convey the scope of the example embodiments to those skilled in the art. In the drawing FIGURE, dimensions may be exaggerated for clarity of illustration. Like reference numerals refer to like elements throughout.

As used herein, the term "and/or" includes any and all combinations of one or more of the associated listed items. Expressions such as "at least one of," when preceding a list of elements, modify the entire list of elements and do not modify the individual elements of the list.

According to an example embodiment, there is provided a compound represented by Formula 1 below:

<Formula 1>

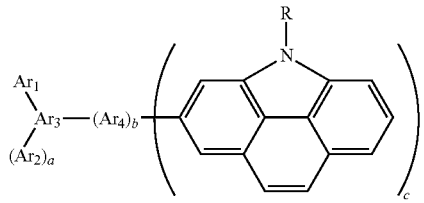

In Formula 1, $Ar_1$, $Ar_2$, $Ar_3$, $Ar_4$, and R may each independently be a substituted or unsubstituted $C_6$-$C_{60}$ aryl group, a substituted or unsubstituted $C_{10}$-$C_{60}$ condensed polycyclic group, or a substituted or unsubstituted $C_3$-$C_{60}$ heteroaryl group; and a may be an integer from 0 to 2, b may be an integer from 0 to 4, and c may be an integer from 1 to 3.

In some embodiments, when b is 2 or more, $Ar_4$ may be identical to or different from each other.

The compound of Formula 1 according to the present example embodiment may function as a light-emitting material for the OLED. Also, the compound of Formula 1 above may have a high glass transition temperature Tg or a melting point. Therefore, in regard to the OLED, the compound of Formula 1 above may increase its thermal resistance and high-temperature environment resistance against Joule heat that is generated in an organic layer, between organic layers, or between an organic layer and a metal electrode. The OLED manufactured using the compound of Formula 1 may have a large effect on increasing advantages such as high durability during storage or operation.

The substituents in the compound of Formula 1 above will now be described in more detail.

In some embodiments, $Ar_1$ and $Ar_2$ in Formula 1 above may each independently be one of the following compounds represented by Formulas 2a to 2e below:

2a

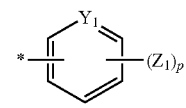

2b

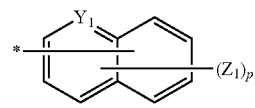

2c

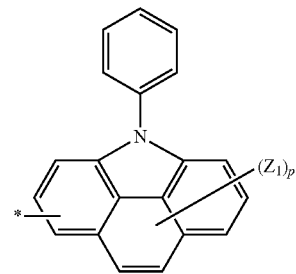

2d

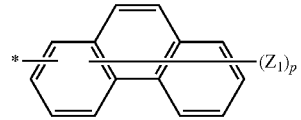

2e

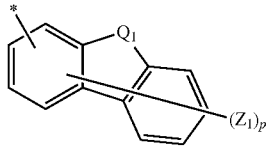

In Formulas 2a to 2e, $Q_1$ may be a group represented by —C($R_{30}$)($R_{31}$)—, —N($R_{32}$)—, —S—, or —O—;

$Y_1$ may be CH or N;

$Z_1$, $R_{30}$, $R_{31}$, and $R_{32}$ may each independently be a hydrogen atom, a deuterium atom, a substituted or unsubstituted $C_1$-$C_{20}$ alkyl group, a substituted or unsubstituted $C_6$-$C_{20}$ aryl group, a substituted or unsubstituted $C_3$-$C_{20}$ heteroaryl group, a substituted or unsubstituted $C_6$-$C_{20}$ condensed polycyclic group, —Si($R_{40}$)$_3$, a halogen atom, a cyano group, a nitro group, a hydroxyl group, or a carboxyl group;

$R_{40}$ may be a substituted or unsubstituted $C_1$-$C_{20}$ alkyl group, a substituted or unsubstituted $C_6$-$C_{20}$ aryl group, a substituted or unsubstituted $C_3$-$C_{20}$ heteroaryl group, or a substituted or unsubstituted $C_6$-$C_{20}$ condensed polycyclic group;

p may be an integer from 1 to 9; and * may be a binding site. In an implementation, $Q_1$ may be a linking group.

In some other embodiments, $Ar_3$ in Formula 1 above may be represented by Formula 3a or Formula 3b below:

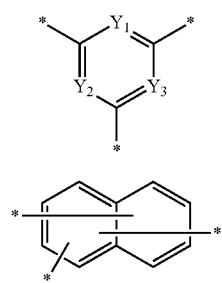

3a

3b

In Formulas 3a and 3b, $Y_1$, $Y_2$, and $Y_3$ may each independently be CH or N, and * may be a binding site.

In some other embodiments, $Ar_4$ in Formula 1 above may be one of the following compounds represented by Formulas 4a to 4f:

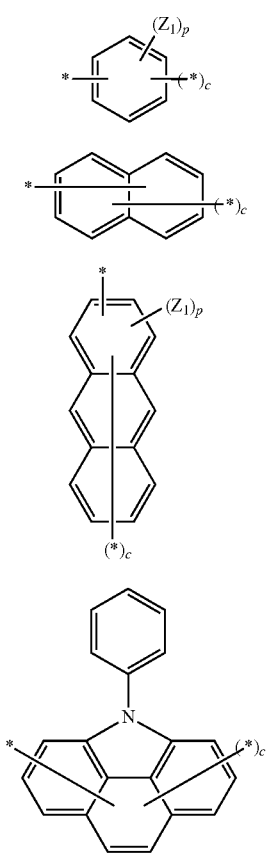

4a

4b

4c

4d

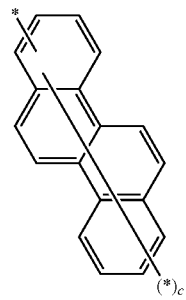

4e

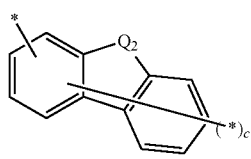

4f

In Formulas 4a to 4f, $Q_2$ may be a group represented by —C($R_{30}$)($R_{31}$)—;

$Z_1$, $R_{30}$, and $R_{31}$ may each independently be a hydrogen atom, a deuterium atom, a substituted or unsubstituted $C_1$-$C_{20}$ alkyl group, a substituted or unsubstituted $C_6$-$C_{20}$ aryl group, a substituted or unsubstituted $C_3$-$C_{20}$ heteroaryl group, a substituted or unsubstituted $C_6$-$C_{20}$ condensed polycyclic group, a halogen atom, a cyano group, a nitro group, a hydroxyl group, or a carboxyl group;

p may be an integer from 1 to 9; c may be an integer from 1 to 3; and * may be a binding site. In an implementation, $Q_2$ may be a linking group.

In some other embodiments, R in Formula 1 above may be represented by Formula 5a or Formula 5b below:

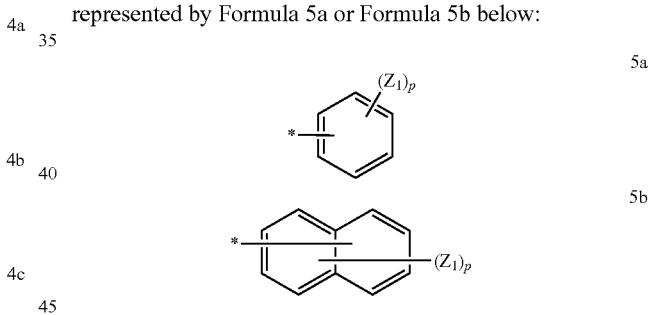

5a

5b

In Formulas 5a and 5b, $Z_1$ may be a hydrogen atom, a deuterium atom, a substituted or unsubstituted $C_1$-$C_{20}$ alkyl group, a substituted or unsubstituted $C_6$-$C_{20}$ aryl group, a substituted or unsubstituted $C_3$-$C_{20}$ heteroaryl group, a substituted or unsubstituted $C_6$-$C_{20}$ condensed polycyclic group, a halogen atom, a cyano group, a nitro group, a hydroxyl group, or a carboxyl group;

p may be an integer from 1 to 7; and * may be a binding site.

Hereinafter, the description of representative substituent used herein will now be described in detail. (In this regard, numbers of carbons limiting a substituent are non-limited, and thus the substituent characteristics are not limited).

The unsubstituted $C_1$-$C_{60}$ alkyl group used herein may be linear or branched. Non-limiting examples of the unsubstituted $C_1$-$C_{60}$ alkyl group are a methyl group, an ethyl group, a propyl group, an iso-butyl group, a sec-butyl group, a pentyl group, an iso-amyl group, a hexyl group, a heptyl group, an octyl group, a nonanyl group, and a dodecyl group. At least one hydrogen atom of the unsubstituted $C_1$-$C_{60}$ alkyl group may be substituted with a deuterium atom, a halogen atom, a hydroxyl group, a nitro group, a cyano group, an amino group, an amidino group, a hydrazine, a hydrazone, a carboxyl group or a salt thereof, a sulfonic acid group or a salt thereof, a phosphoric acid group or a salt thereof, a $C_1$-$C_{10}$ alkyl group, a $C_1$-$C_{10}$ alkoxy group, a $C_2$-$C_{10}$ alkenyl group, a $C_2$-$C_{10}$ alkynyl group, a $C_6$-$C_{16}$ aryl group, or a $C_4$-$C_{16}$ heteroaryl group.

The unsubstituted $C_2$-$C_{60}$ alkenyl group indicates an unsubstituted alkenyl group having at least one carbon-carbon double bond in the center or at a terminal thereof. Examples of the unsubstituted $C_2$-$C_{60}$ alkenyl group are an ethenyl group, a propenyl group, a butenyl group, and the like. At least one hydrogen atom of the unsubstituted alkenyl group may be substituted with the same substituent as used in the substituted alkyl group described above.

The unsubstituted $C_2$-$C_{60}$ alkynyl group indicates an unsubstituted alkynyl group having at least one carbon-carbon triple bond in the center or at a terminal of thereof. Examples of the unsubstituted $C_2$-$C_{60}$ alkynyl group are acetylene, propylene, phenylacetylene, naphthylacetylene, isopropylacetylene, t-butylacetylene, diphenylacetylene, and the like. At least one hydrogen atom of the unsubstituted $C_2$-$C_{60}$ alkynyl group may be substituted with the same substituent as used in the substituted alkyl group.

The unsubstituted $C_3$-$C_{60}$ cycloalkyl group indicates an alkyl group in the form of $C_3$-$C_{60}$ rings, and at least one hydrogen atom of the $C_3$-$C_{60}$ cycloalkyl group may be substituted with the same substituent with the same substituent as used in the $C_1$-$C_{60}$ alkyl group.

The unsubstituted $C_1$-$C_{60}$ alkoxy group has a structure of —OA (wherein, A is an unsubstituted $C_1$-$C_{60}$ alkyl group described above). Non-limiting examples of the unsubstituted $C_1$-$C_{60}$ alkoxy group are a methoxy group, an ethoxy group, a propoxy group, an isopropyloxy group, a butoxy group, a pentoxy group, and the like. At least one hydrogen atom of the unsubstituted alkoxy group may be substituted with the same substituent as used in the substituted alkyl group.

The unsubstituted $C_6$-$C_{60}$ aryl group indicates a carbocyclic aromatic system including at least one ring. When the unsubstituted $C_6$-$C_{60}$ aryl group has two or more of rings, the rings may be fused or linked to each other by a single bond. The term 'aryl' refers to an aromatic system such as phenyl, naphthyl, and anthracenyl. Also, at least one hydrogen atom of the aryl group may be substituted with the same substituent as used in the $C_1$-$C_{60}$ alkyl group.

Examples of the substituted or unsubstituted $C_6$-$C_{60}$ aryl group are a phenyl group, a $C_1$-$C_{10}$ alkylphenyl group (i.e., an ethylphenyl group), a halophenyl group (i.e., an o-, m-, and p-fluorophenyl group and a dichlorophenyl group), a cyanophenyl group, a dicyanophenyl, a trifluoromethoxyphenyl group, a biphenyl group, a halobiphenyl group, a cyanobiphenyl group, a $C_1$-$C_{10}$ alkylbiphenyl group, a $C_1$-$C_{10}$ alkoxybiphenyl group, an o-, m-, and p-tolyl group, an o-, m-, and p-cumenyl group, a mesityl group, a phenoxyphenyl group, a (α,α-dimethylbenzene)phenyl group, a (N,N'-dimethyl)aminophenyl group, a (N,N'-diphenyl)aminophenyl group, a pentalenyl group, an indenyl group, a naphthyl group, a halonaphthyl group (i.e., a fluoronaphthyl group), a $C_1$-$C_{10}$ alkylnaphthyl group (i.e., a methylnaphthyl group), a $C_1$-$C_{10}$ alkoxynaphthyl group (i.e., a methoxynaphthyl group), a cyanonaphthyl group, an anthracenyl group, an azulenyl group, a heptalenyl group, an acenaphthylenyl group, a phenalenyl group, a fluorenyl group, an anthraquinolyl group, a methylanthryl group, a phenanthryl group, a triphenylene group, a pyrenyl group, a chrycenyl group, an ethyl-chrysenyl group, a picenyl group, a perylenyl group, a chloroperylenyl group, a pentaphenyl group, a pentacenyl group, a tetraphenylenyl group, a hexaphenyl group, a hexacenyl group, a rubicenyl group, a coronelyl group, a trinaphthylenyl group, a heptaphenyl group, a heptacenyl group, a pyranthrenyl group, an ovalenyl group, and the like.

The unsubstituted $C_3$-$C_{60}$ heteroaryl group used herein may include one, two, or three hetero atoms selected from N, O, P, or S. When the unsubstituted $C_3$-$C_{60}$ heteroaryl group has two or more of rings, the rings are fused or linked to each other by a single bond. Examples of the unsubstituted $C_4$-$C_{60}$ heteroaryl group are a pyrazolyl group, an imidazolyl group, an oxazolyl group, a thiazolyl group, a triazolyl group, a tetrazolyl group, an oxadiazolyl group, a pyridinyl group, a pyridazinyl group, a pyrimidinyl group, a triazinyl group, a carbazolyl group, an indolyl group, a quinolinyl group, an isoquinolinyl group, and a dibenzothiophene group, and the like. In addition, at least one hydrogen atom of the heteroaryl group may be substituted with the same substituent as used in the unsubstituted $C_1$-$C_{60}$ alkyl group.

The unsubstituted $C_6$-$C_{60}$ aryloxy group is a group represented by —$OA_1$, wherein $A_1$ is a $C_6$-$C_{60}$ aryl group. Examples of the aryloxy group are a phenoxy group, and the like. At least one hydrogen atom of the aryloxy group may be substituted with the same substituent as used in the unsubstituted $C_1$-$C_{60}$ alkyl group.

The unsubstituted $C_6$-$C_{60}$ arylthio group is a group represented by —$SA_1$, wherein $A_1$ is a $C_6$-$C_{60}$ aryl group. Examples of the arylthio group are a benzylthio group, a naphthylthio group, and the like. At least one hydrogen atom of the arylthio group may be substituted with the same substituent as used in the unsubstituted $C_1$-$C_{60}$ alkyl group.

The unsubstituted $C_6$-$C_{60}$ condensed polycyclic group used herein refers to a substituent including at least two rings, wherein at least one aromatic ring and at least one non-aromatic ring are fused to each other, or a substituent having an unsaturated group within a ring but being unable to form a conjugated structure. The $C_6$-$C_{60}$ condensed polycyclic group may be, e.g., a fluorenyl group. Therefore, the unsubstituted $C_6$-$C_{60}$ condensed polycyclic group is distinct from the aryl or the heteroaryl groups in terms of being non-aromatic.

Examples of the compound of Formula 1 according to the present example embodiment are the following compounds below, but are not limited thereto:

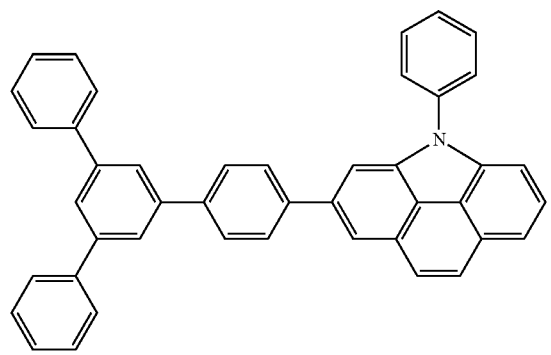

1

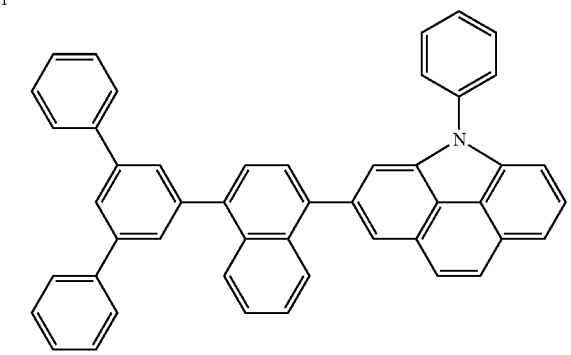

2

-continued
3
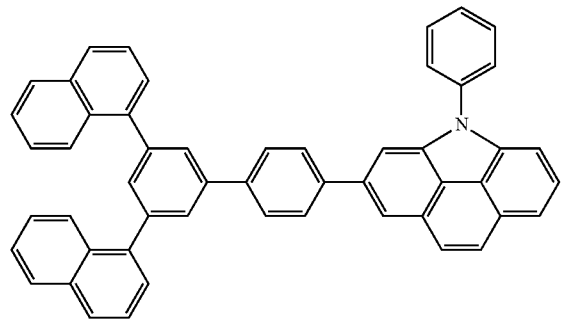
4
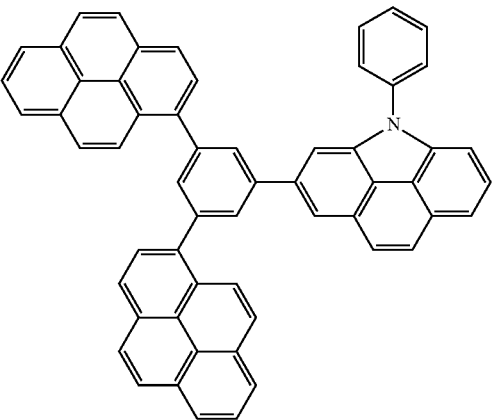
5
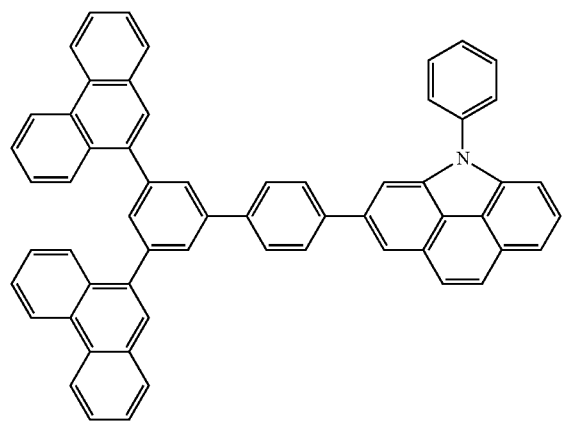
6
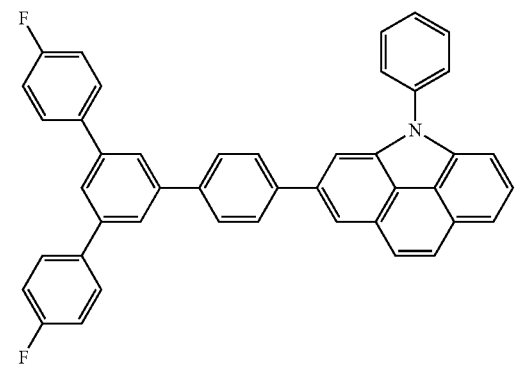
7
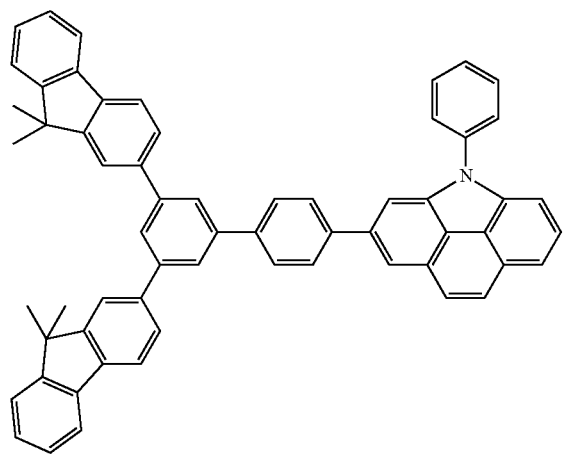
8
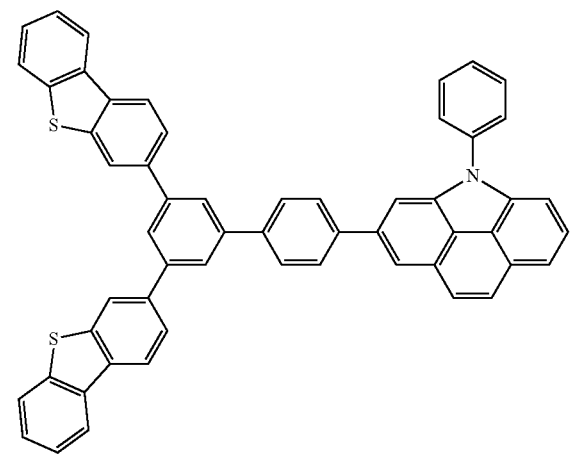

-continued
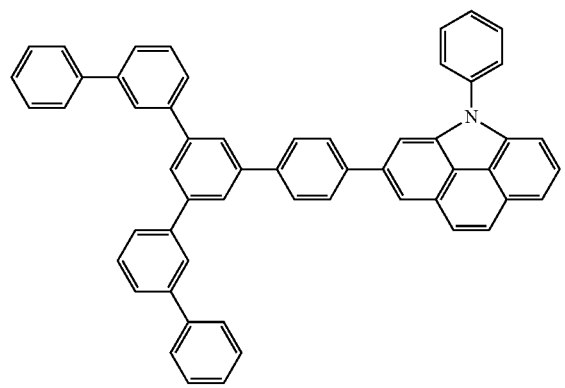
9
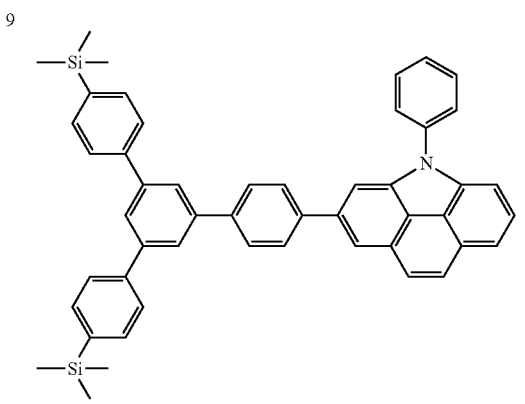
10
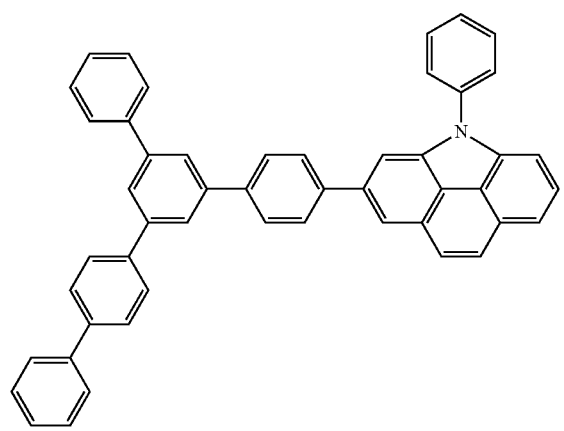
11
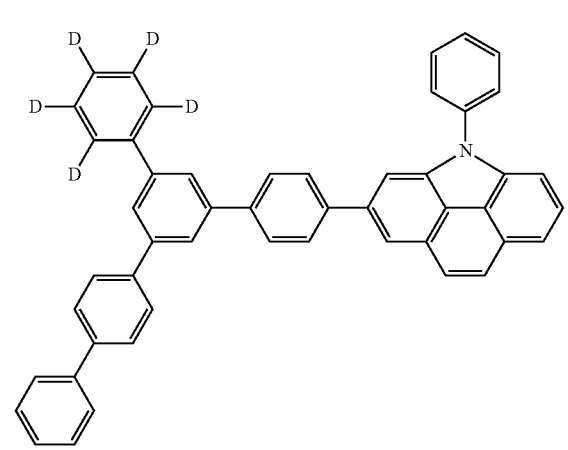
12
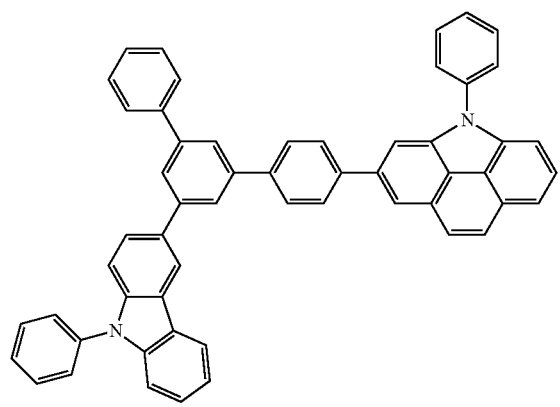
13
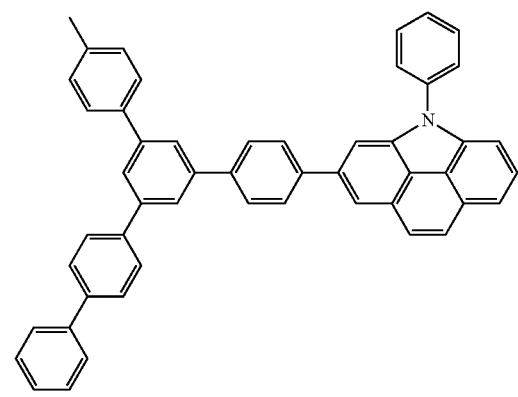
14

-continued
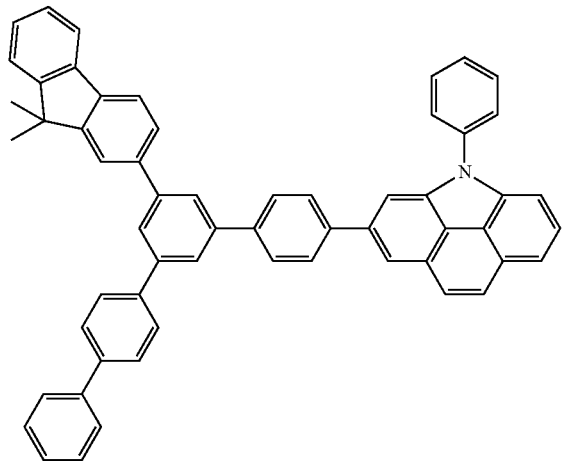
15
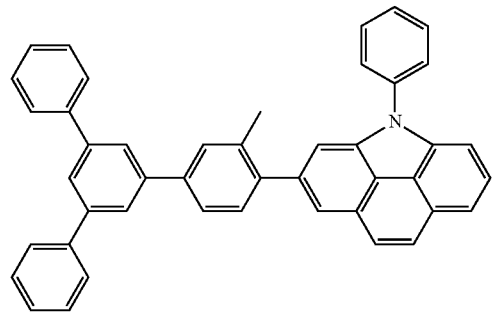
16
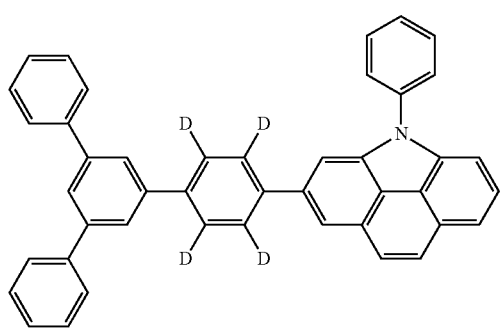
17
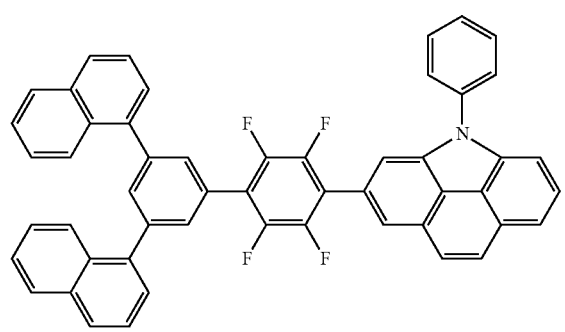
18
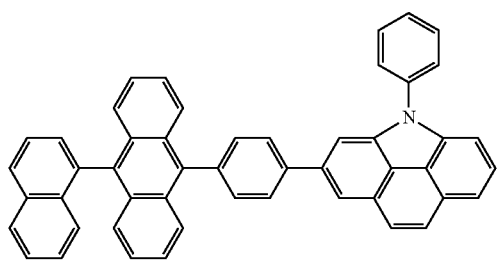
19
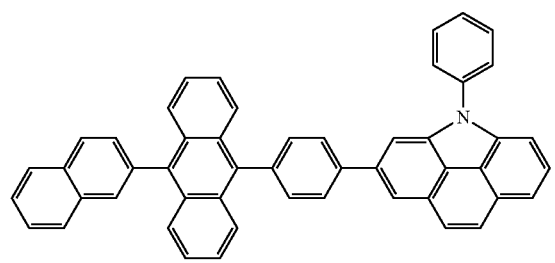
20
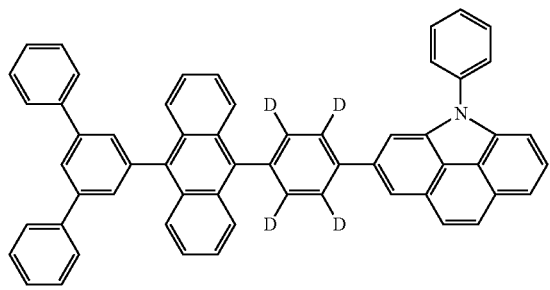
21
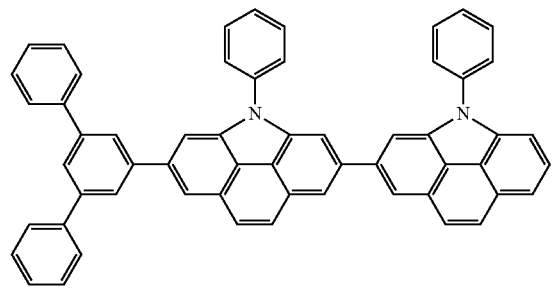
22

-continued
23
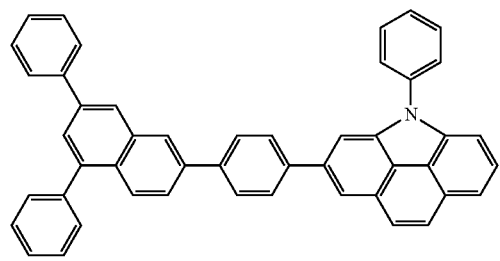
24
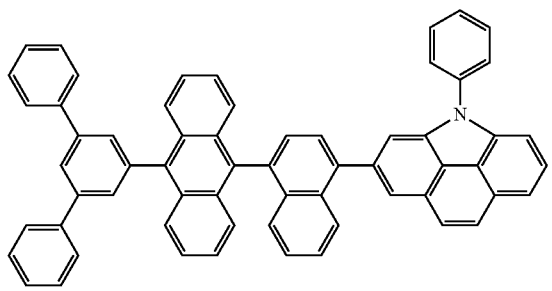
25
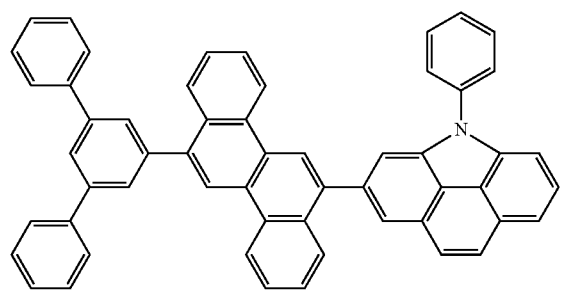
26
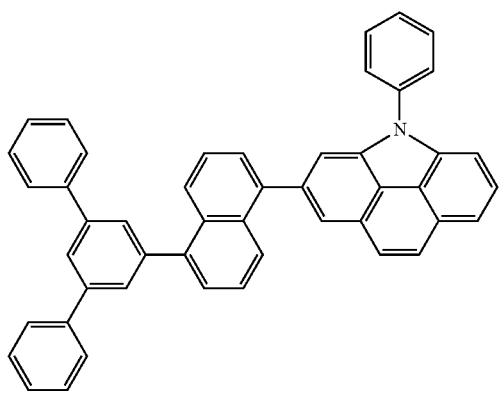
27
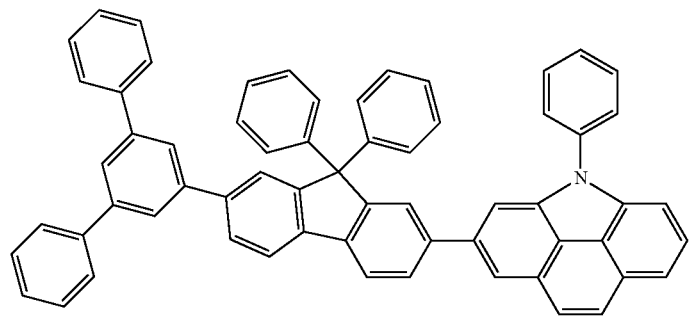
28
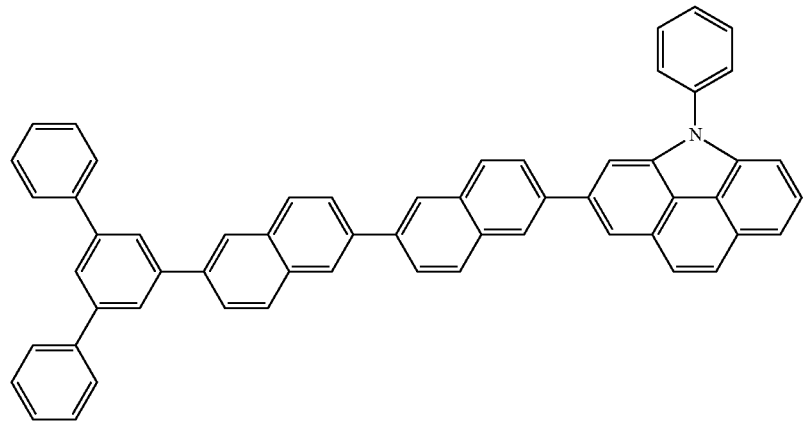

-continued
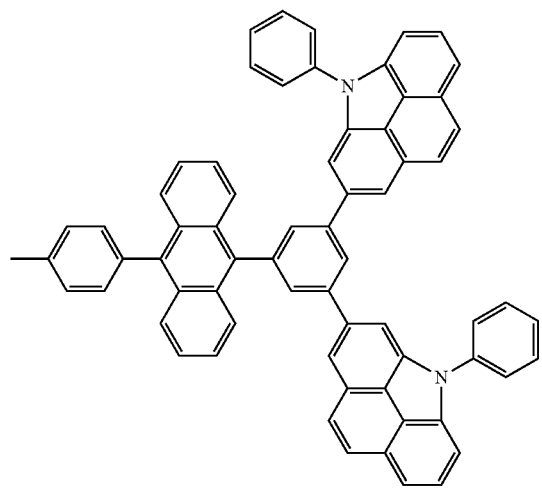
29
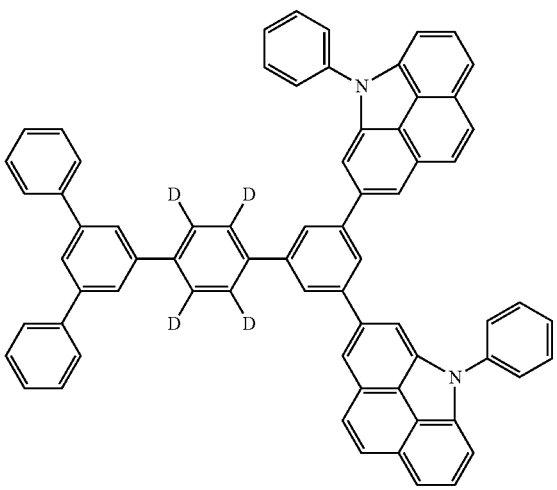
30
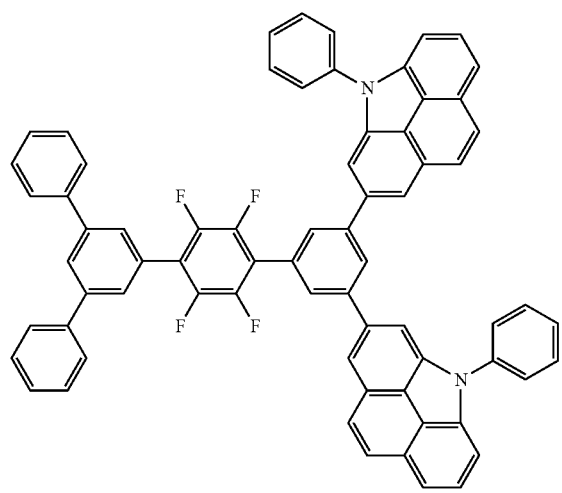
31
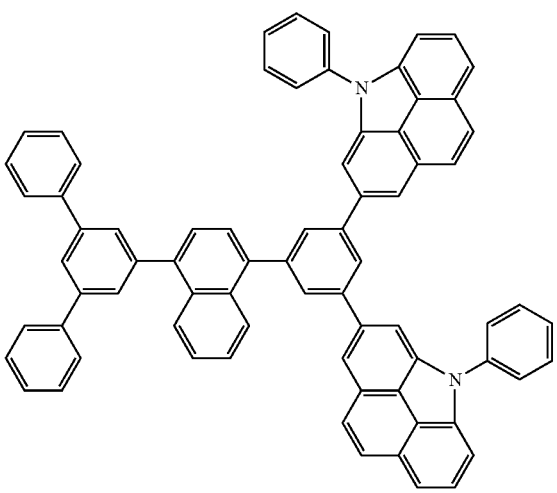
32
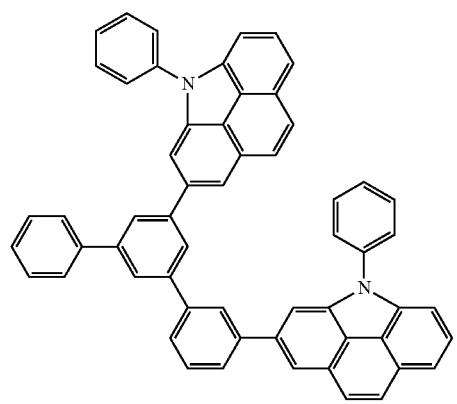
33
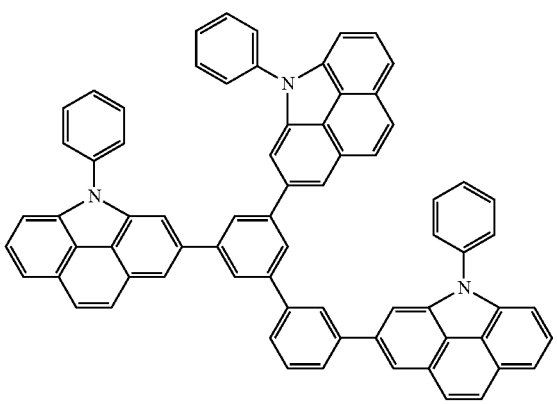
34

-continued
35
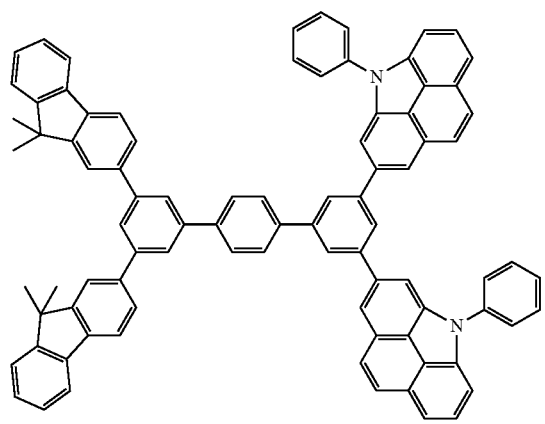
36
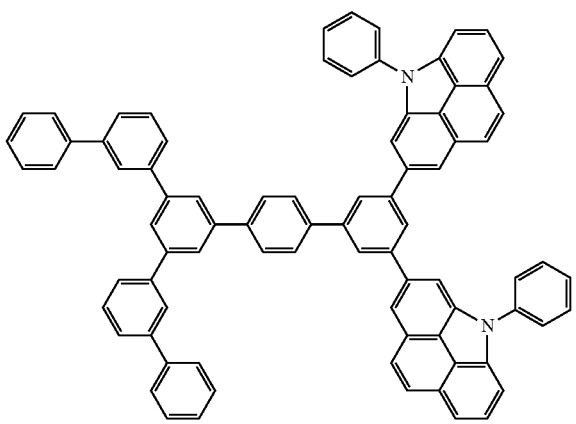
37
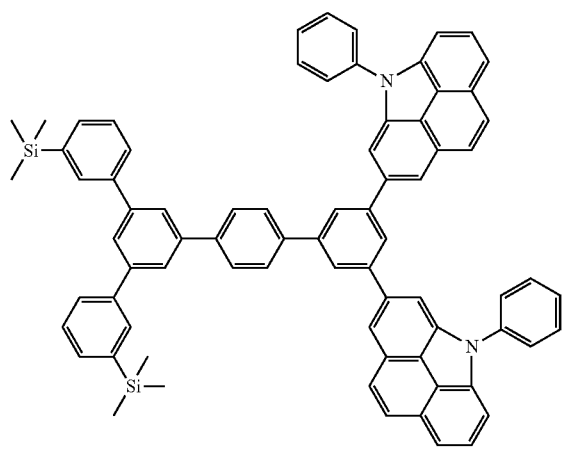
38
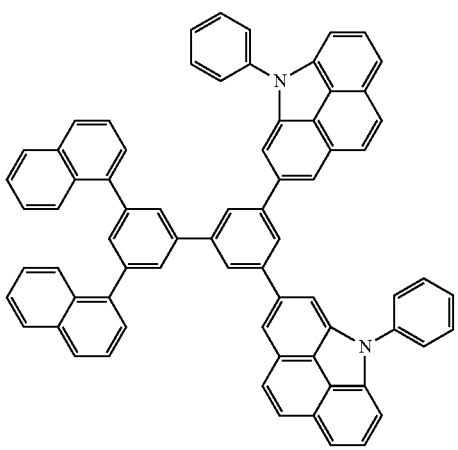
39
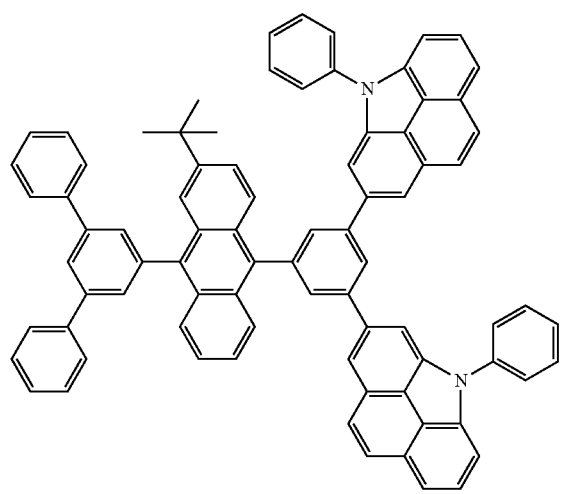
40
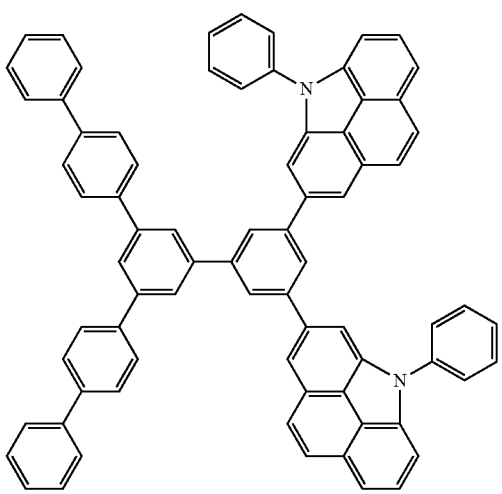

-continued
41
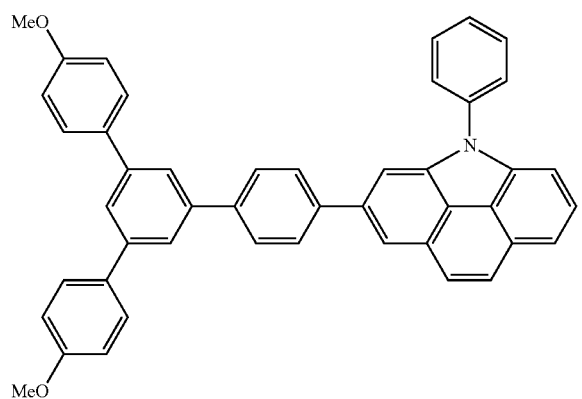
42
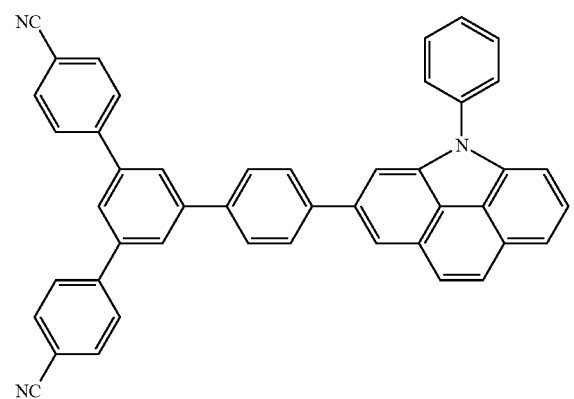
43
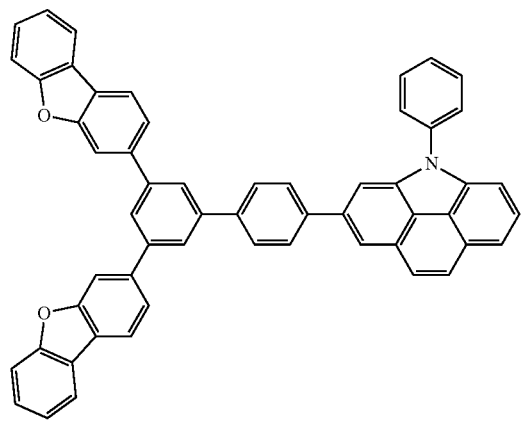
44
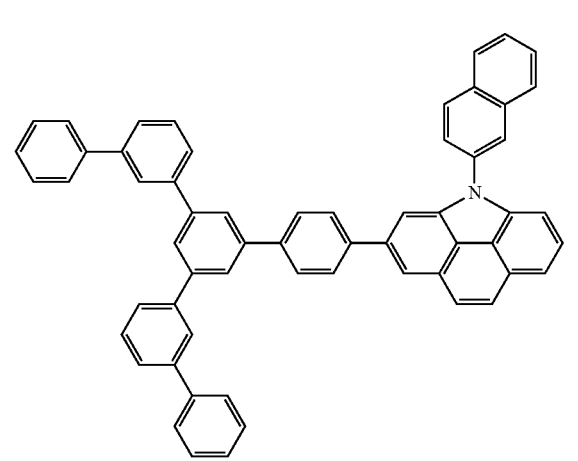
45
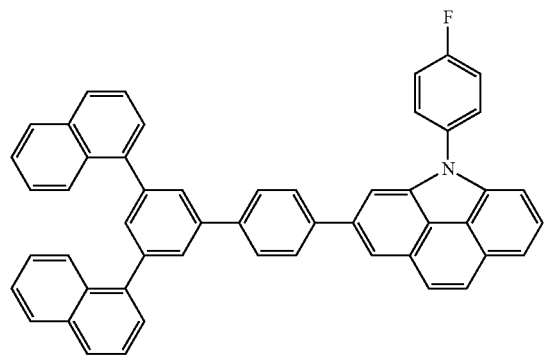
46
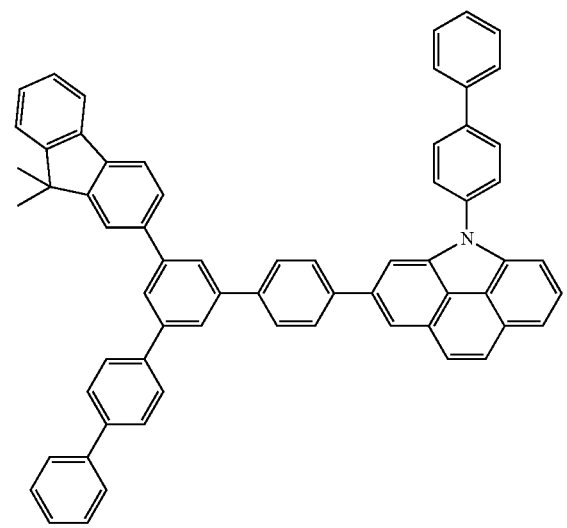

-continued
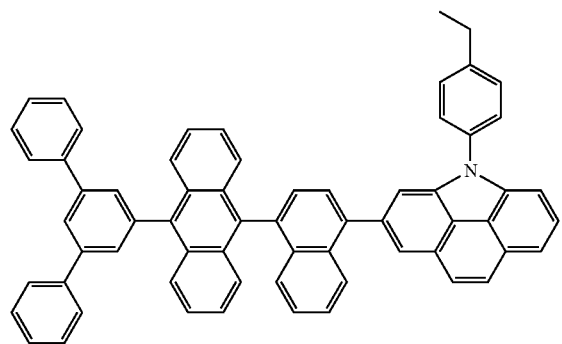
47
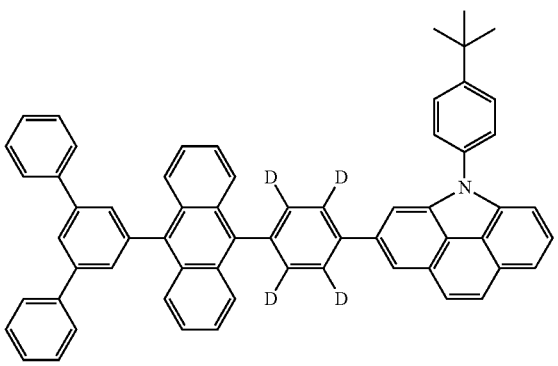
48
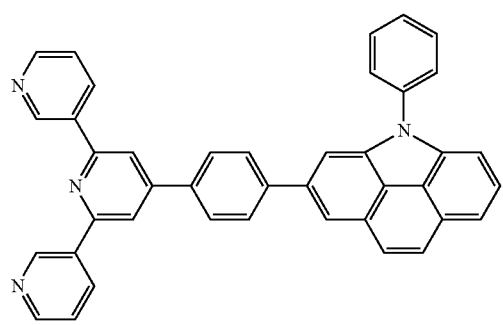
49
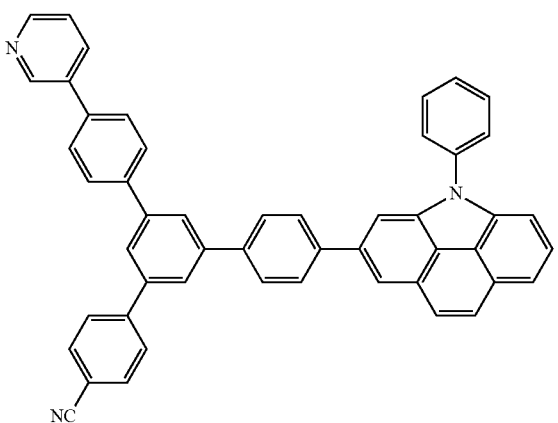
50
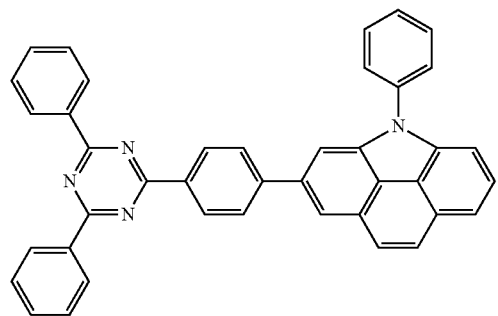
51
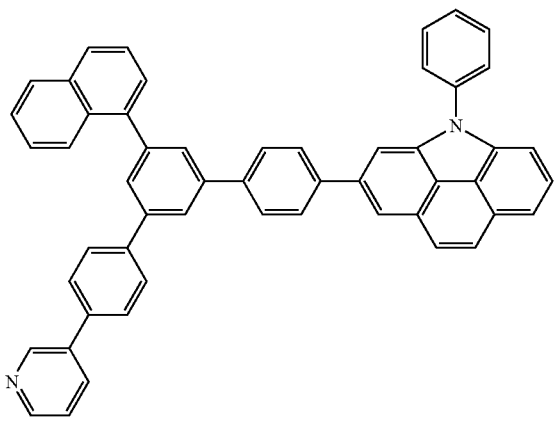
52
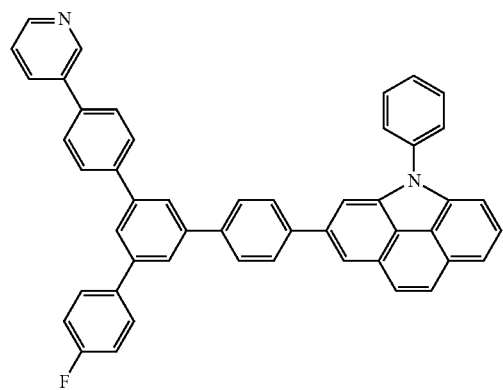
53
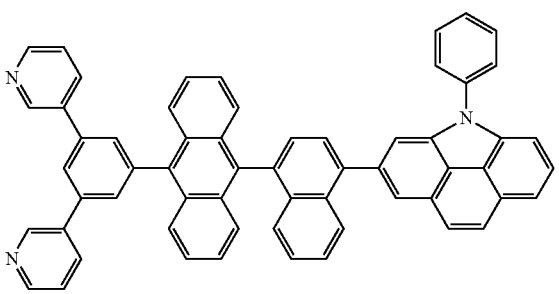
54

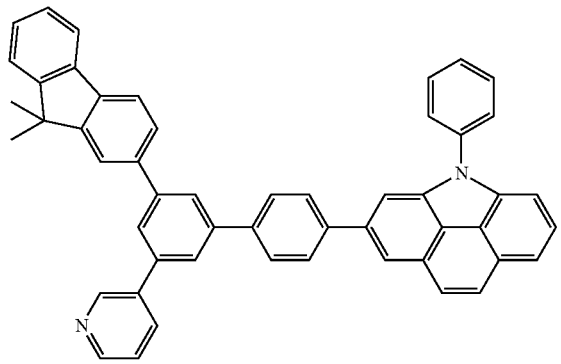

55

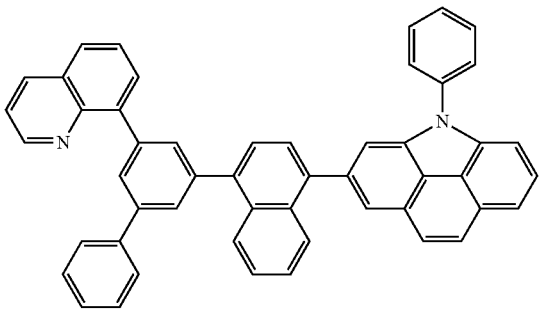

56

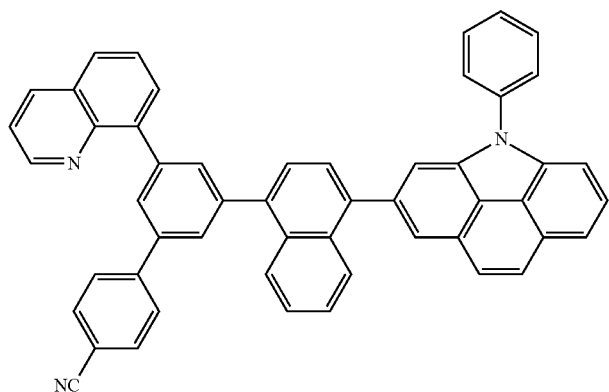

57

According to another example embodiment, an OLED includes a first electrode; a second electrode; and an organic layer that is disposed between the first electrode and the second electrode and includes the compound of Formula 1 above.

The organic layer may include at least one layer selected from a hole injection layer (HIL), a hole transport layer (HTL), a functional layer having both hole injection and hole transport capabilities (hereinafter, referred as a "H-functional layer"), a buffer layer, an electron blocking layer (EBL), an emission layer (EML), a hole blocking layer (HBL), an electron transport layer (ETL), an electron injection layer (EIL), and a functional layer having both electron injection and electron transport capabilities (hereinafter, referred as an "E-functional layer").

For example, the organic layer may be an EML or a charge-transfer layer. For example, the organic layer may be a blue EML or an ETL.

In some embodiments, the OLED may include an EIL, an ETL, an EML, a HIL, a HTL, or a H-functional layer having both hole injection and hole transport capabilities, wherein the EML may include the compound of Formulas above; and an anthracene-based compound, an arylamine-based compound, or a styryl-based compound.

In some other embodiments, the OLED may include an EIL, an ETL, an EML, a HIL, a HTL, or a H-functional layer having both hole injection and hole transport capabilities, wherein at least one of a red EML, a green EML, a blue EML, and a white EML of the EML may include a phosphorescent compound, and the HIL, the HTL, or the H-functional layer having both hole injection and hole transport capabilities may include a charge-generating material. The charge-generating material may be a p-dopant, and the p-dopant may be a quinone derivative, a metal oxide, or a cyano group-containing compound.

In some other embodiments, the organic layer may include an ETL, and the ETL may include an electron-transporting organic compound and a metal complex. The metal complex may be a lithium (Li) complex.

The term "organic layer" used herein refers to a single layer and/or a multi-layer disposed between the first electrode and the second electrode of the OLED.

In an example embodiment, the organic layer includes an EML, and the EML may include the compound of Formulas above. In some embodiments, the organic layer may include at least one layer of a HIL, a HTL, a H-functional layer having both hole injection and hole transport capabilities, and at least one layer of the HIL, the HTL, and the H-functional layer having both hole injection and hole transport capabilities may include the compound of Formulas above.

FIG. 1 is a schematic view of a structure of an OLED according to an example embodiment. Hereinafter, a structure and a manufacturing method of an OLED according to an example embodiment will be described in detail with reference to FIG. 1.

A substrate (not illustrated), which may be any suitable substrate that is in used in a general OLED, may be a glass substrate or a transparent plastic substrate with excellent mechanical strength, thermal stability, transparency, surface smoothness, ease of handling, and water resistance.

A first electrode may be formed by depositing or sputtering a material for a first electrode on the substrate. When the first electrode is an anode, the material for the first electrode may be selected from materials with a high work function to enable ease of hole injection. The first electrode may be a reflective electrode or a transmission electrode. The material for the first electrode may be a transparent material with high conductivity, and examples thereof are indium tin oxide (ITO), indium zinc oxide (IZO), tin oxide ($SnO_2$), and zinc oxide (ZnO). When magnesium (Mg), aluminum (Al), aluminum-lithium (Al—Li), calcium (Ca), magnesium-indium (Mg—In), magnesium-silver (Mg—Ag), or the like is used, the first electrode may be used as a reflective electrode.

The first electrode may have a single-layer structure or a multi-layer structure including at least two layers. For example, the first electrode may have a three-layered structure of ITO/Ag/ITO, but is not limited thereto.

The organic layer may be disposed on the first electrode.

The organic layer may include a HIL, a HTL, a buffer layer (not illustrated), an EML, an ETL, or an EIL.

An HIL may be formed on the first electrode by using various methods such as vacuum deposition, spin coating, casting, and Langmuir-Blodgett (LB) deposition.

When the HIL is formed using vacuum deposition, vacuum deposition conditions may vary depending on the compound that is used to form the HIL, and the desired structure and thermal properties of the HIL to be formed. For example, the vacuum deposition may be performed at a temperature of about 100° C. to about 500° C., a pressure of about $10^{-8}$ torr to about $10^{-3}$ torr, and a deposition rate of about 0.01 Å/sec to about 100 Å/sec. However, the deposition conditions are not limited thereto.

When the HIL is formed using spin coating, the coating conditions may vary depending on the compound that is used to form the HIL, and the desired structure and thermal properties of the HIL to be formed. For example, the coating rate may be in a range from about 2,000 rpm to about 5,000 rpm, and a temperature at which heat treatment is performed to remove a solvent after coating may be in a range from about 80° C. to about 200° C. However, the coating conditions are not limited thereto.

As a material for the HIL, a general hole-injecting material, for example, N,N'-diphenyl-N,N'-bis-[4-(phenyl-m-tolyl-amino)-phenyl]-biphenyl-4,4'-diamine (DNTPD), a phthalocyanine compound such as copper phthalocyanine, 4,4',4"-tris(3-methylphenylphenylamino)triphenylamine (m-MTDATA), N,N'-di(1-naphthyl)-N,N'-diphenylbenzidine (NPB), TDATA, 2-TNATA, polyaniline/dodecylbenzenesulfonic acid (Pani/DBSA), poly(3,4-ethylenedioxythiophene)/poly(4-styrenesulfonate) (PEDOT/PSS), polyaniline/camphor sulfonic acid (Pani/CSA), or polyaniline/poly(4-styrenesulfonate) (PANI/PSS) may be used, but the hole-injecting material is not limited thereto:

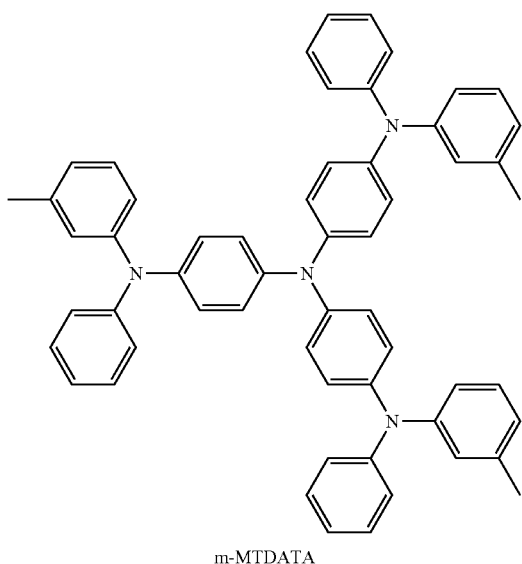

m-MTDATA

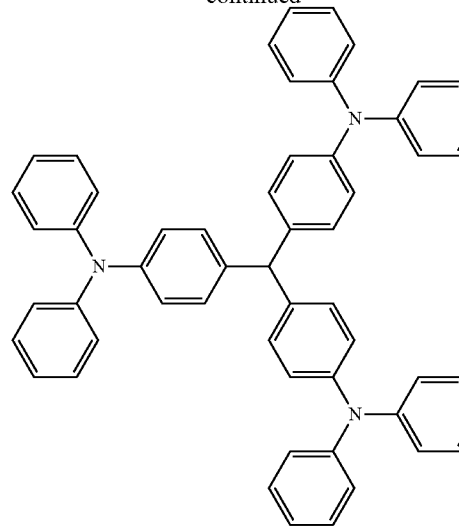

TDATA

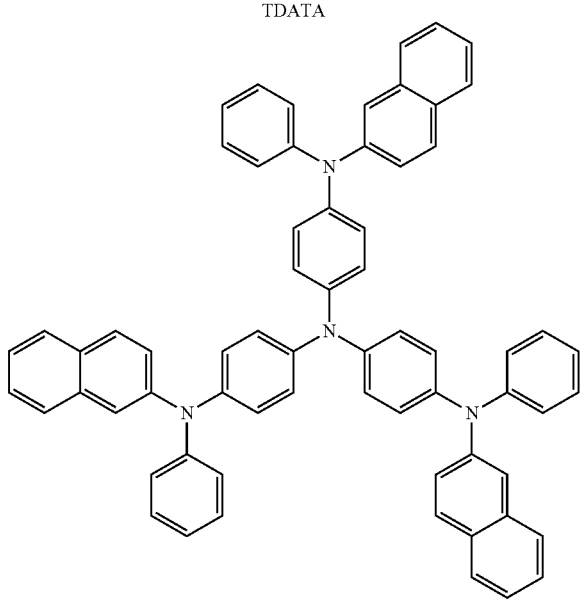

2-TNATA

A thickness of the HIL may be in a range from about 100 Å to about 10,000 Å, for example, from about 100 Å to about 1,000 Å. When the thickness of the HIL is within the above ranges, the HIL may have satisfactory hole injection characteristics without a substantial increase in a driving voltage.

Then, an HTL may be formed on the HIL by using vacuum deposition, spin coating, casting, LB deposition, or the like. When the HTL is formed using vacuum deposition or spin coating, the deposition and coating conditions may be similar to those for the formation of the HIL, although the deposition and coating conditions may vary depending on a compound that is used to form the HTL.

As a material for the HTL, a general hole-transporting material, for example, a carbazole derivative such as N-phenylcarbazole or polyvinylcarbazole, N,N'-bis(3-methylphenyl)-N,N'-diphenyl-[1,1-biphenyl]-4,4'-diamine (TPD), 4,4', 4"-tris(N-carbazolyl)triphenylamine) (TCTA), and N,N'-di (1-naphthyl)-N,N'-diphenylbenzidine (NPB) may be used, but the hole-transporting material is not limited thereto:

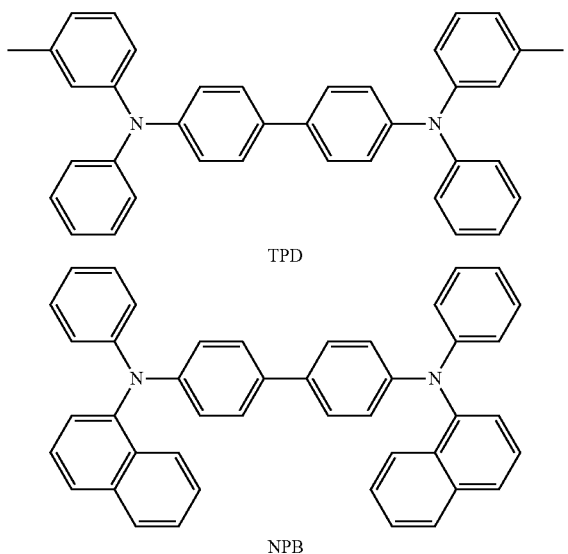

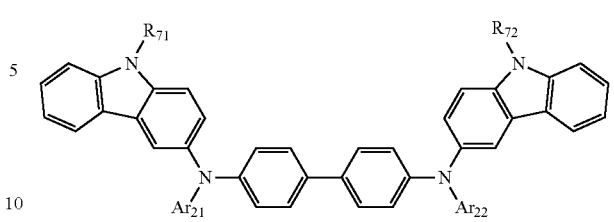

A thickness of the HTL may be in a range from about 50 Å to about 2,000 Å, for example, from about 100 Å to about 1,500 Å. When the thickness of the HTL is within the above ranges, the HTL may have satisfactory hole transport characteristics without a substantial increase in a driving voltage.

The H-functional layer (a functional layer having both hole injection and hole transport capabilities) may include one or more materials selected from the above-described materials for the HIL and the HTL. A thickness of the H-functional layer may be in a range from about 500 Å to about 10,000 Å, for example, from about 100 Å to about 1,000 Å. When the thickness of the H-functional layer is within the above ranges, the H-functional layer may have satisfactory hole injection and transport characteristics without a substantial increase in a driving voltage.

In some embodiments, at least one layer of the HIL, the HTL, and the H-functional layer may include at least one of the following compounds represented by Formulas 300 and 350 below:

<Formula 300>

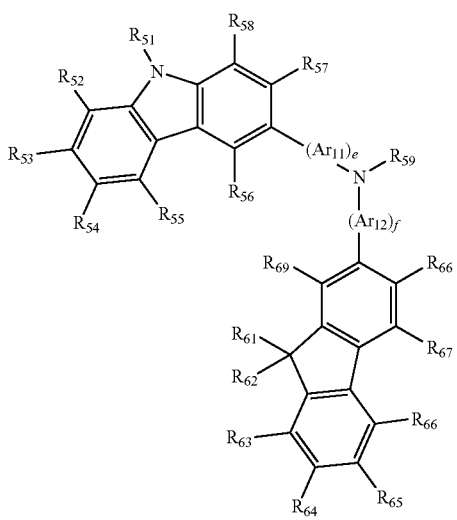

<Formula 350>

$Ar_{11}$, $Ar_{12}$, $Ar_{21}$, and $Ar_{22}$ in Formulas 300 and 350 may each independently be a substituted or unsubstituted $C_5$-$C_{60}$ arylene group.

e and f in Formula 300 may each independently be an integer from 0 to 5, for example, 0, 1, or 2. In some embodiments, e may be 1 and f may be 0, but are not limited thereto.

$R_{51}$ to $R_{58}$, $R_{61}$ to $R_{69}$, $R_{71}$, and $R_{72}$ in Formulas 300 and 350 may each independently be a hydrogen atom, a deuterium atom, a halogen atom, a hydroxyl group, a cyano group, a nitro group, an amino group, an amidino group, a hydrazine, a hydrazone, a carboxyl group or a salt thereof, a sulfonic acid or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_5$-$C_{60}$ aryl group, a substituted or unsubstituted $C_5$-$C_{60}$ aryloxy group, or a substituted or unsubstituted $C_5$-$C_{60}$ arylthio group. For example, $R_{51}$ to $R_{58}$, $R_{61}$ to $R_{69}$, $R_{71}$, and $R_{72}$ may each independently be selected from a hydrogen atom; a deuterium atom; a halogen atom; a hydroxyl group; a cyano group; a nitro group; an amino group; an amidino group; a hydrazine; a hydrazone; a carboxyl group or a salt thereof; a sulfonic acid or a salt thereof; a phosphoric acid or a salt thereof; a $C_1$-$C_{10}$ alkyl group (i.e., a methyl group, an ethyl group, a propyl group, a butyl group, a pentyl group, a hexyl group, or the like); a $C_1$-$C_{10}$ alkoxy group (i.e., a methoxy group, an ethoxy group, a propoxy group, a butoxy group, a pentoxy group, or the like);

a $C_1$-$C_{10}$ alkyl group and a $C_1$-$C_{10}$ alkoxy group, each substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid or a salt thereof, and a phosphoric acid or a salt thereof;

a phenyl group; a naphthyl group; an anthryl group; a fluorenyl group; a pyrenyl group; and a phenyl group, a naphthyl group, an anthryl group, a fluorenyl group, and a pyrenyl group, each substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid or a salt thereof, a phosphoric acid or a salt thereof, a $C_1$-$C_{10}$ alkyl group, and a $C_1$-$C_{10}$ alkoxy group, but is not limited thereto.

$R_{59}$ in Formula 300 may be selected from a phenyl group; a naphthyl group; an anthryl group; a biphenyl group; a pyridyl group; and a phenyl group, a naphthyl group, an anthryl group, a biphenyl group, and a pyridyl group, each substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid or a salt thereof, a phosphoric acid or a salt thereof, a substituted or unsubstituted $C_1$-$C_{20}$ alkyl group, and a substituted or unsubstituted $C_1$-$C_{20}$ alkoxy group.

In some embodiments, the compound of Formula 300 may be represented by 300A below, but the compound is not limited thereto:

<Formula 300A>

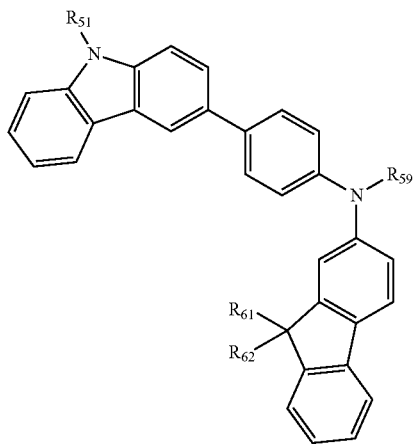

A detailed description of $R_{51}$, $R_{62}$, $R_{61}$, and $R_{59}$ in Formula 300A has already been described above.

For example, at least one layer of the HIL, HTL, and the H-functional layer may include at least one of the following Compounds 301 to 320, but is not limited thereto:

301

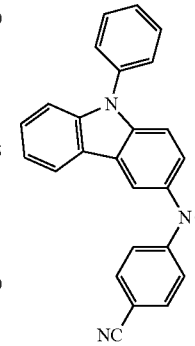

302

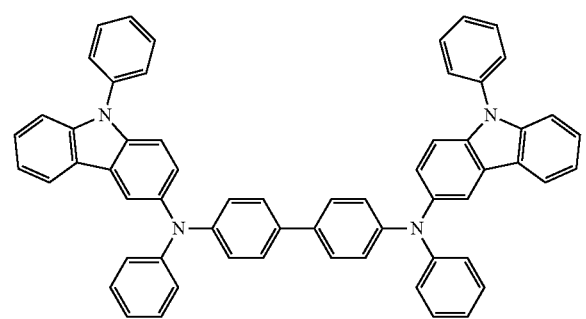

303

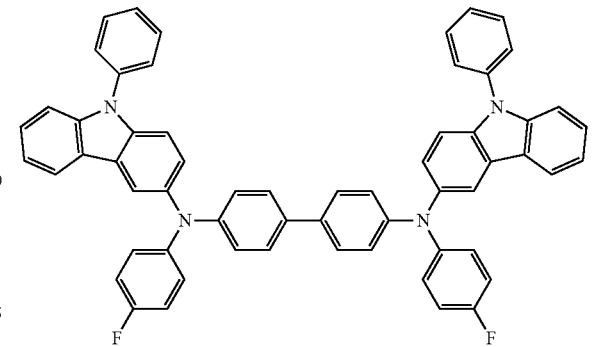

304

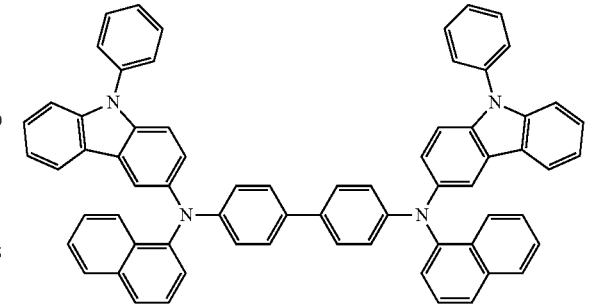

305

306

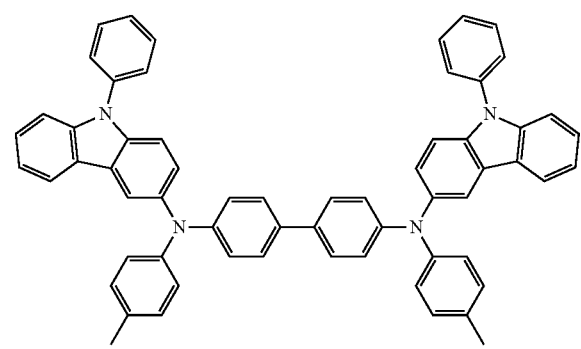

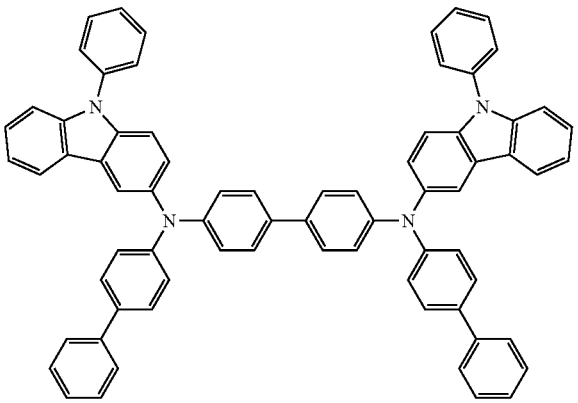

307
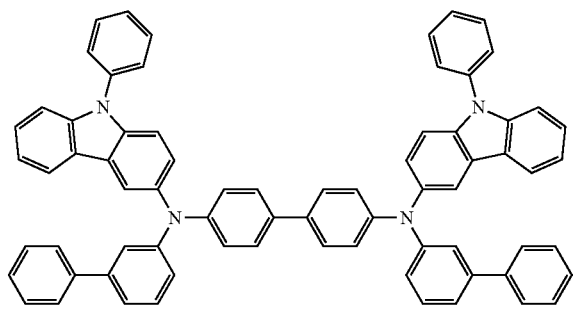
308
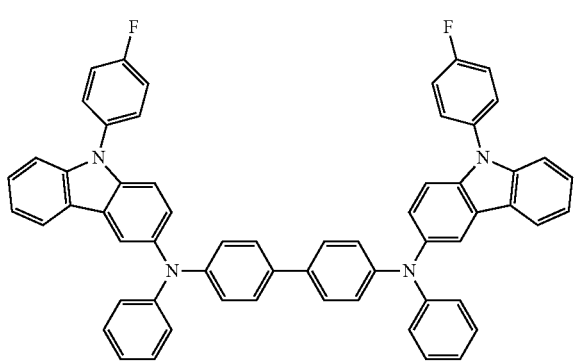
309
310
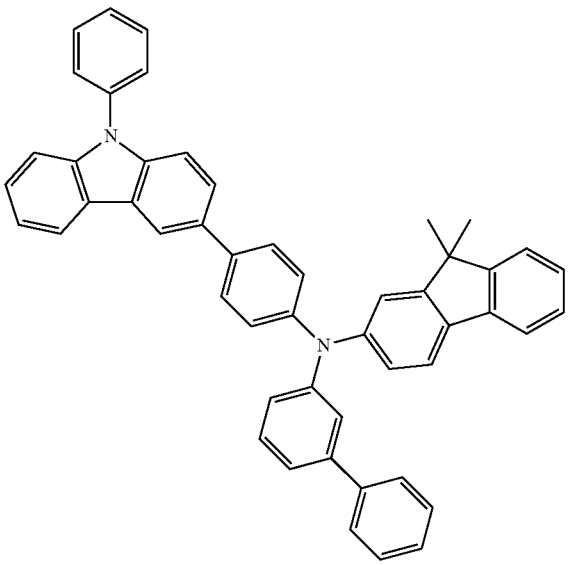
311
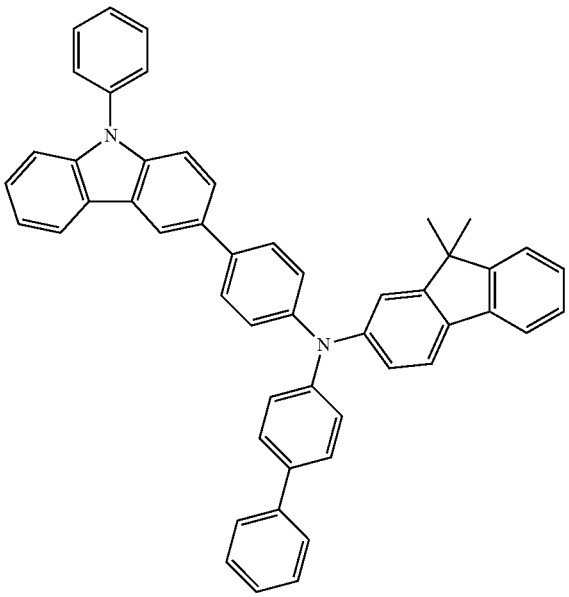

312
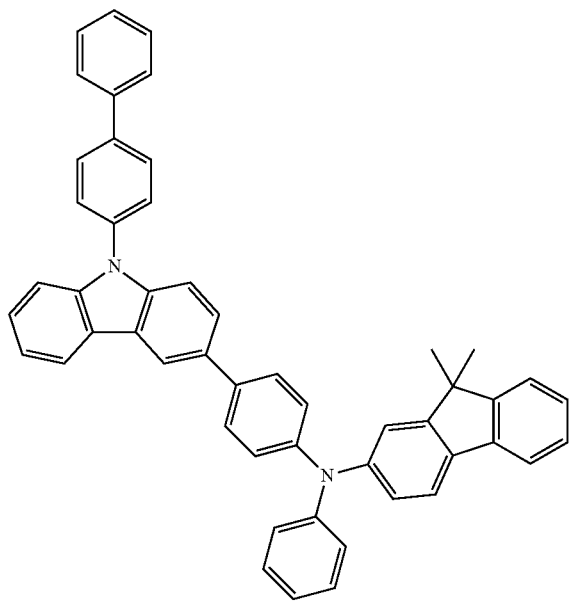
313
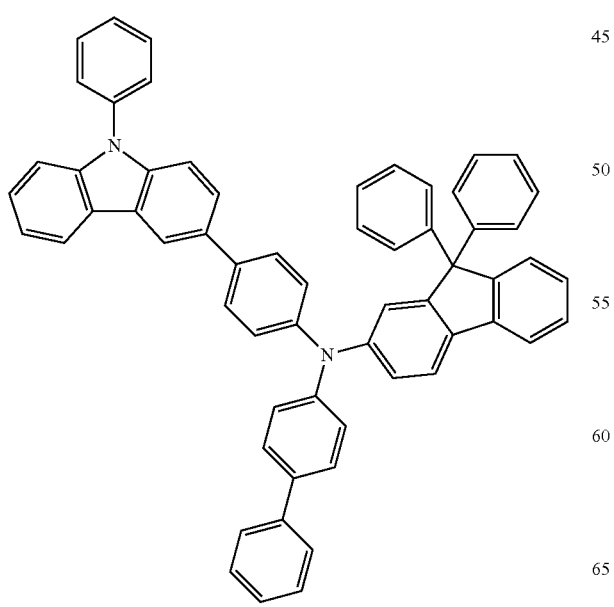
314
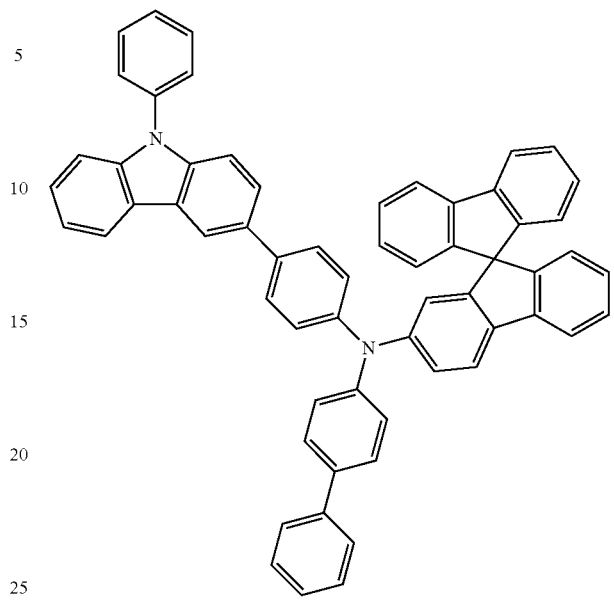
315
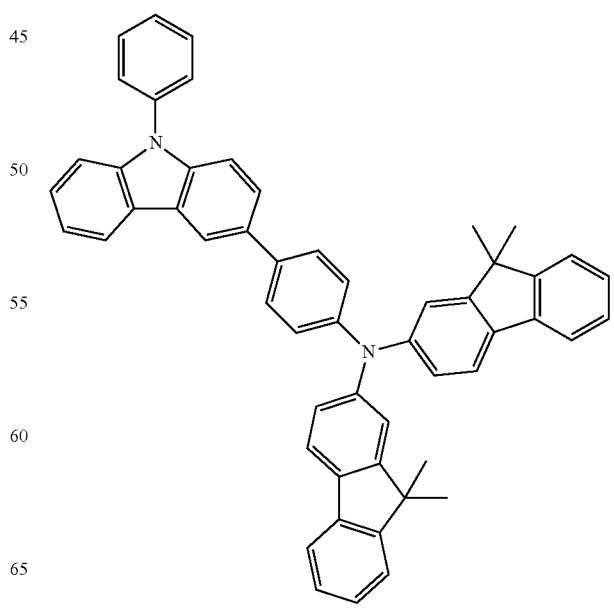

316

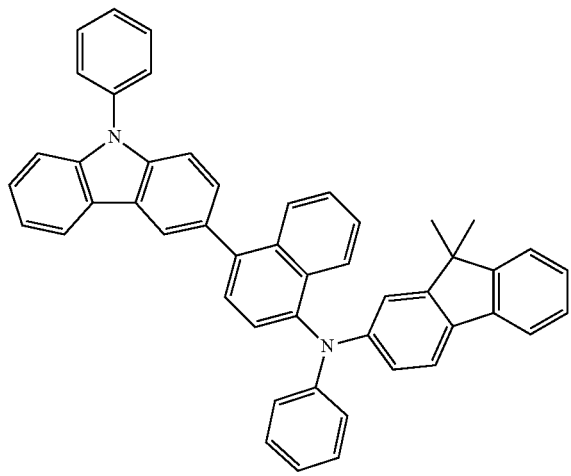

317

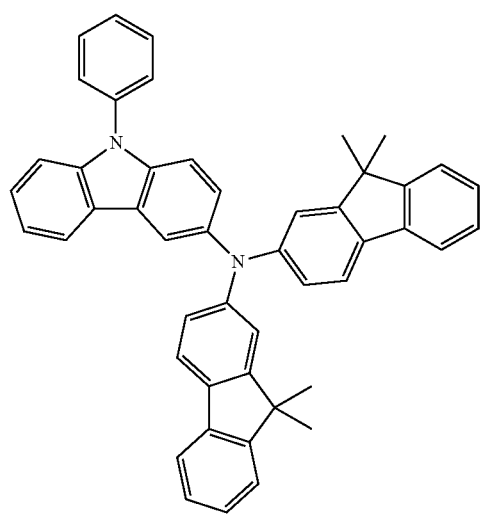

318

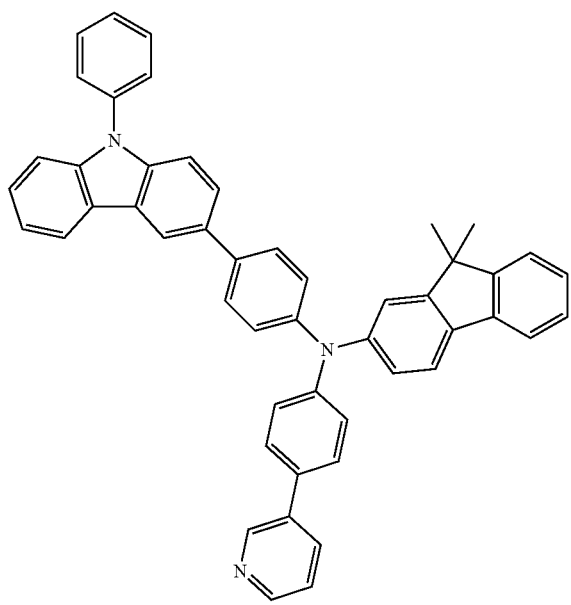

319

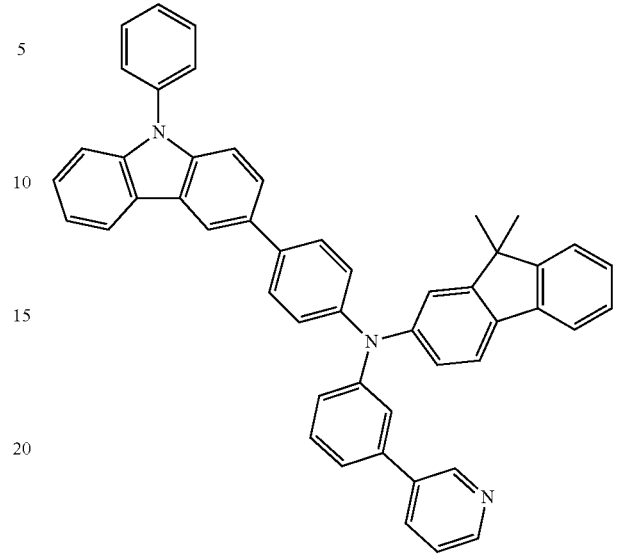

320

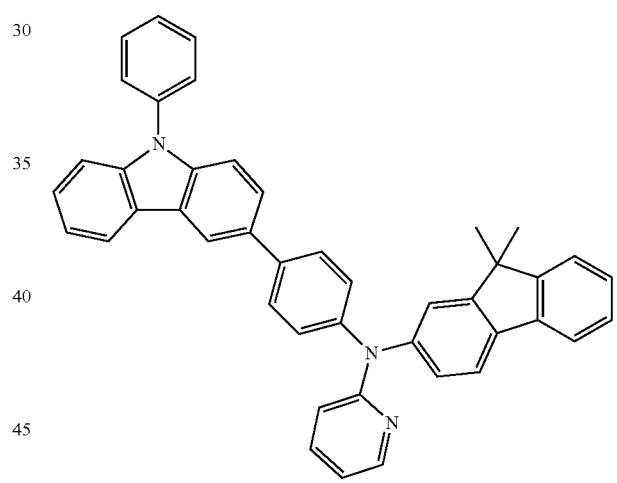

At least one layer of the HIL, HTL, and the H-functional layer may further include a charge-generating material to improve conductivity of a film, in addition to such general hole-injecting materials, general hole-transporting materials, and/or general H-functional materials having both hole injection and hole transport capabilities.

The charge-generating material may be, for example, a p-dopant. The p-dopant may be one of a quinone derivative, a metal oxide, and a compound with a cyano group, but is not limited thereto. Non-limiting examples of the p-dopant are quinone derivatives such as tetracyanoquinodimethane (TCNQ) and 2,3,5,6-tetrafluoro-tetracyano-1,4-benzoquinodimethane (F4-TCNQ); metal oxides such as a tungsten oxide and a molybdenum oxide; and cyano group-containing compounds such as Compound 200 below, but are not limited thereto:

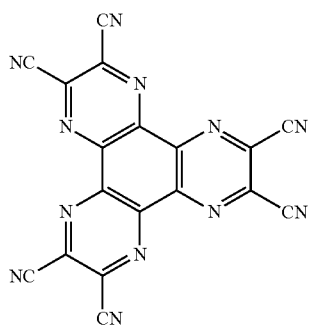

<Formula 200>

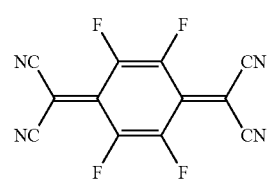

<F4-TCNQ>

When the HIL, the HTL, or the H-functional layer further includes the charge-generating material, the charge-generating material may be homogeneously dispersed or non-homogeneously distributed in the layers above.

A buffer layer may be disposed between at least one of the HIL, HTL, and the H-functional layer, and the EML. The buffer layer may compensate for an optical resonance distance of light according to a wavelength of the light emitted from the EML, and thus may increase efficiency. The buffer layer may include any suitable hole injecting material or hole transporting material. In some other embodiments, the buffer layer may include the same material as one of the materials included in the HIL, the HTL, and the H-functional layer that underlie the buffer layer.

Then, an EML may be formed on the HIL, the H-functional layer, or the buffer layer by vacuum deposition, spin coating, casting, LB deposition, or the like. When the EML is formed using vacuum deposition or spin coating, the deposition and coating conditions may be similar to those for the formation of the HIL, although the conditions for deposition and coating may vary depending on the material that is used to form the EML.

The EML may include the compound of Formula 1 as described above. In addition to the compound of Formula 1, the EML may be formed using a variety of light-emitting materials, for example, a general host and a general dopant. In regard to the dopant, both a general fluorescent dopant and a general phosphorescent dopant may be used.

Examples of the general host are Alq$_3$, 4,4'-N,N'-dicarbazole-biphenyl (CBP), poly(n-vinylcarbazole) (PVK), 9,10-di(naphthylene-2-yl)anthracene (ADN), TCTA, 1,3,5-tris(N-phenylbenzimidazole-2-yl)benzene (TPBI), 3-tert-butyl-9,10-di(naphth-2-yl)anthracene (TBADN), E3, distyrylarylene (DSA), dmCBP (see Formula below), and Compounds 501 to 509 below, but are not limited thereto.

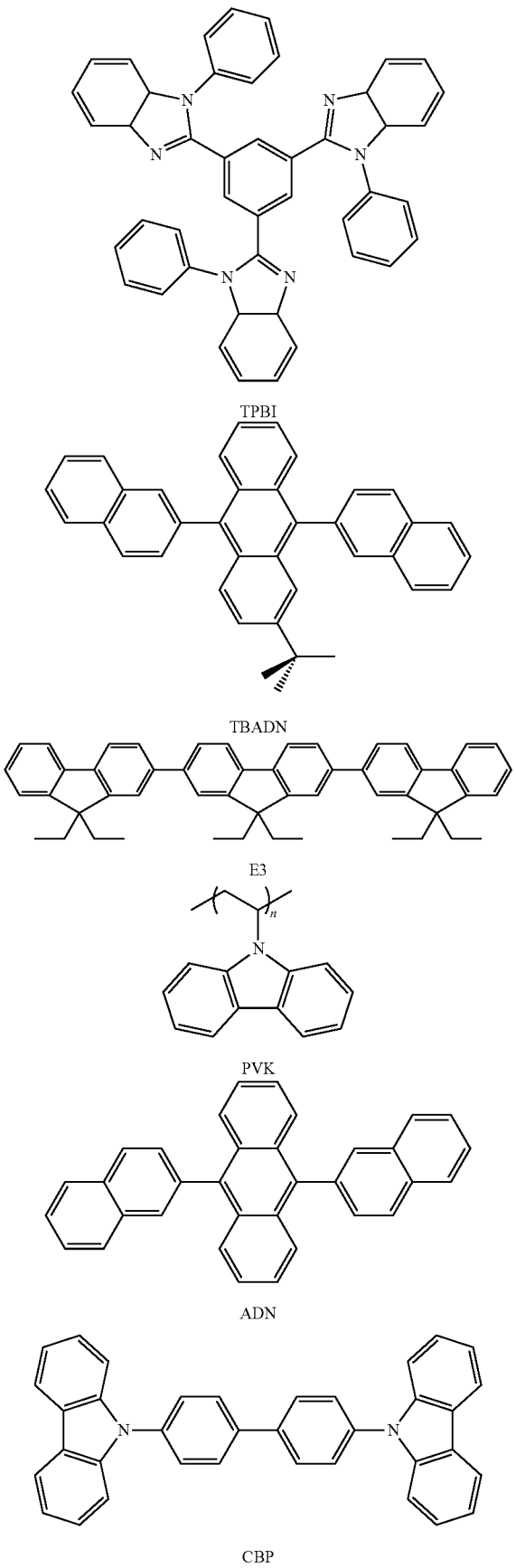

45
-continued
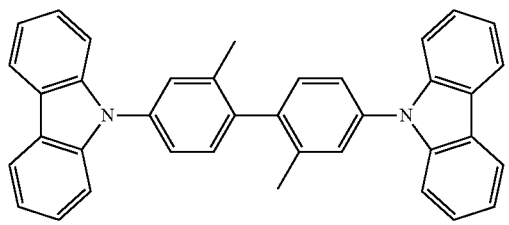
dmCBP
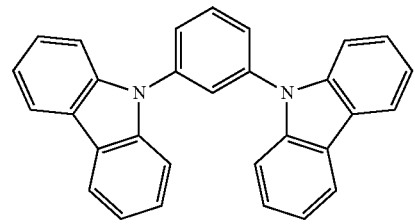
501
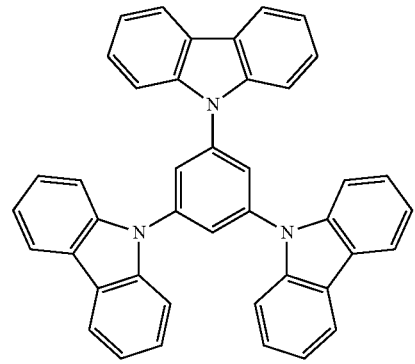
502
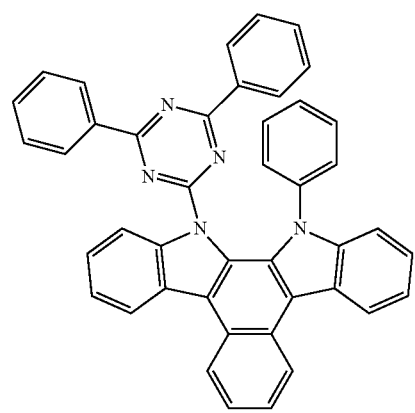
503
46
-continued
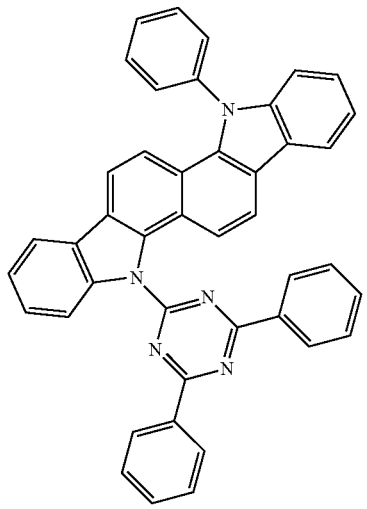
504
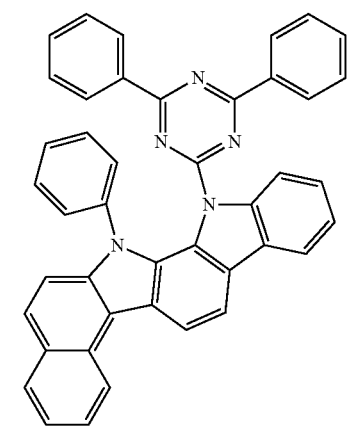
505
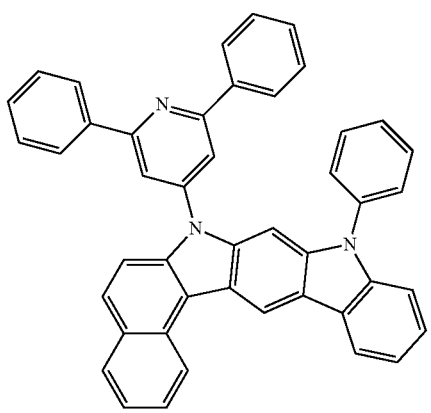
506

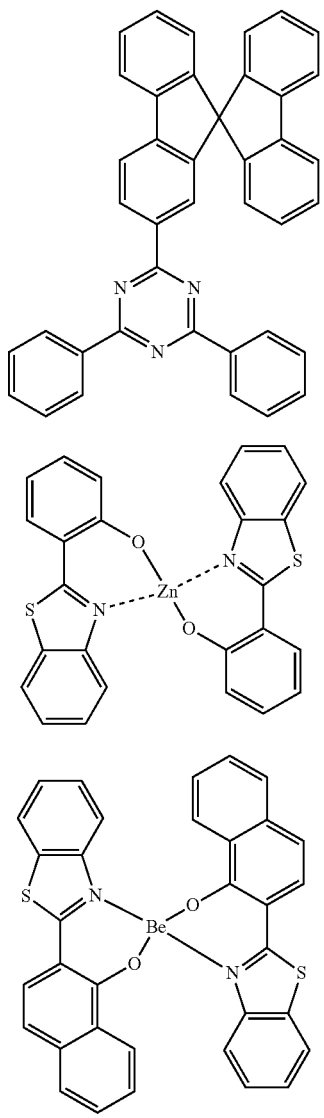

In some embodiments, an anthracene-based compound represented by Formula 400 below may be used as the host:

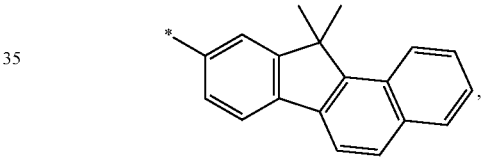

<Formula 400> wherein, in Formula 400, $Ar_{111}$ and $Ar_{112}$ may each independently be a substituted or unsubstituted $C_5$-$C_{60}$ arylene group; $Ar_{113}$ to $Ar_{116}$ may each independently be a substituted or unsubstituted $C_1$-$C_{10}$ alkyl group or a substituted or unsubstituted $C_5$-$C_{60}$ aryl group; and g, h, i and j may each independently be an integer from 0 to 4.

For example, $Ar_{11}$ and $Ar_{112}$ in Formula 400 may each independently be selected from a phenylene group, a naphthylene group, a phenanthrenylene group, or a pyrenylene group; or a phenylene group, a naphthylene group, a phenanthrenylene group, a fluorenyl group, or a pyrenylene group each substituted with at least one of a phenyl group, a naphthyl group, and an anthryl group, but is not limited thereto.

g, h, i, and j in Formula 400 may each independently be 0, 1, or 2.

$Ar_{113}$ to $Ar_{116}$ in Formula 400 may each independently be selected from a $C_1$-$C_{10}$ alkyl group substituted with at least one of a phenyl group, a naphthyl group, and an anthryl group;

a phenyl group; a naphthyl group; an anthryl group; a pyrenyl group; a phenanthrenyl group; a fluorenyl group;

a phenyl group, a naphthyl group, an anthryl group, a pyrenyl group, a phenanthrenyl group, and a fluorenyl group, each substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a phenyl group, a naphthyl group, an anthryl group, a pyrenyl group, a phenanthrenyl group, and a fluorenyl group; and

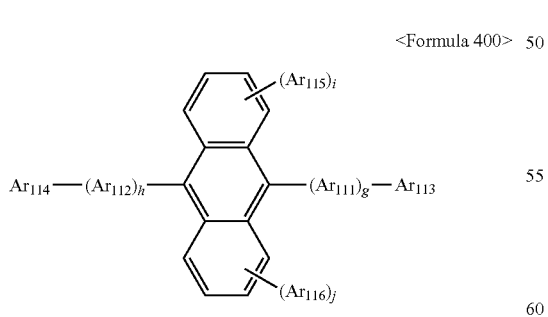

but is not limited thereto.

For example, the anthracene-based compound represented by Formula 400 above may be one of the following compounds represented by Formulas below, but is not limited thereto:

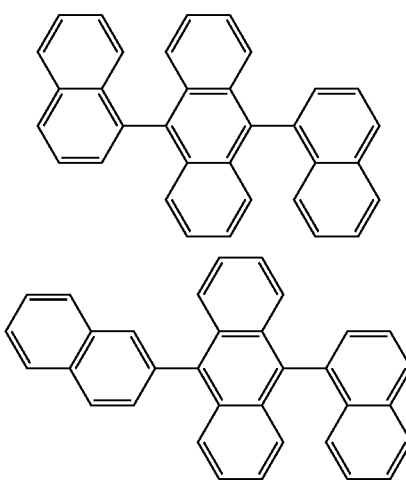

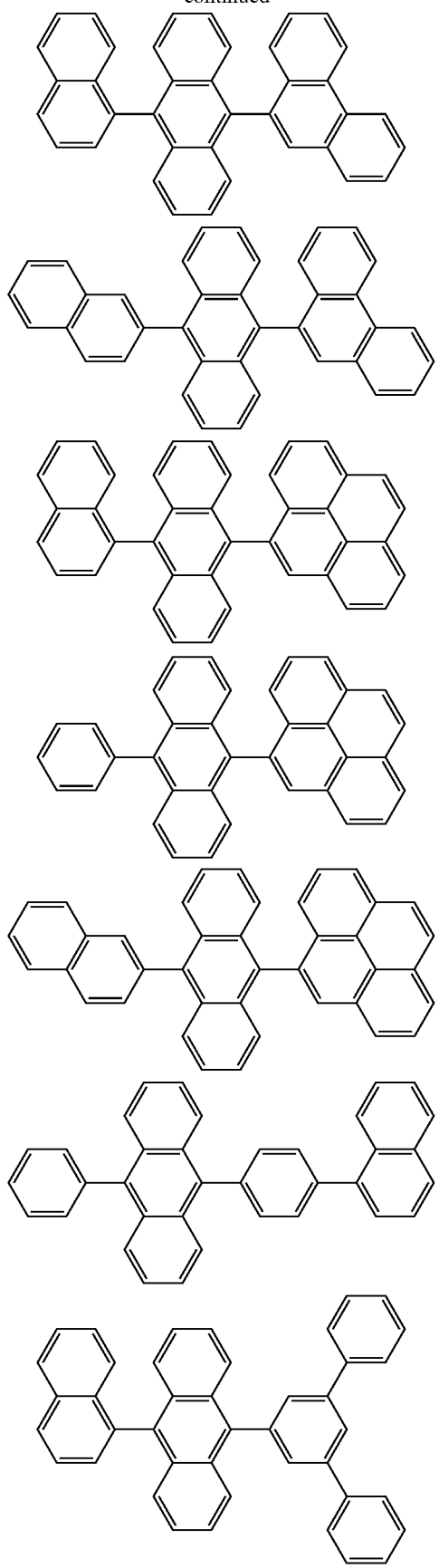
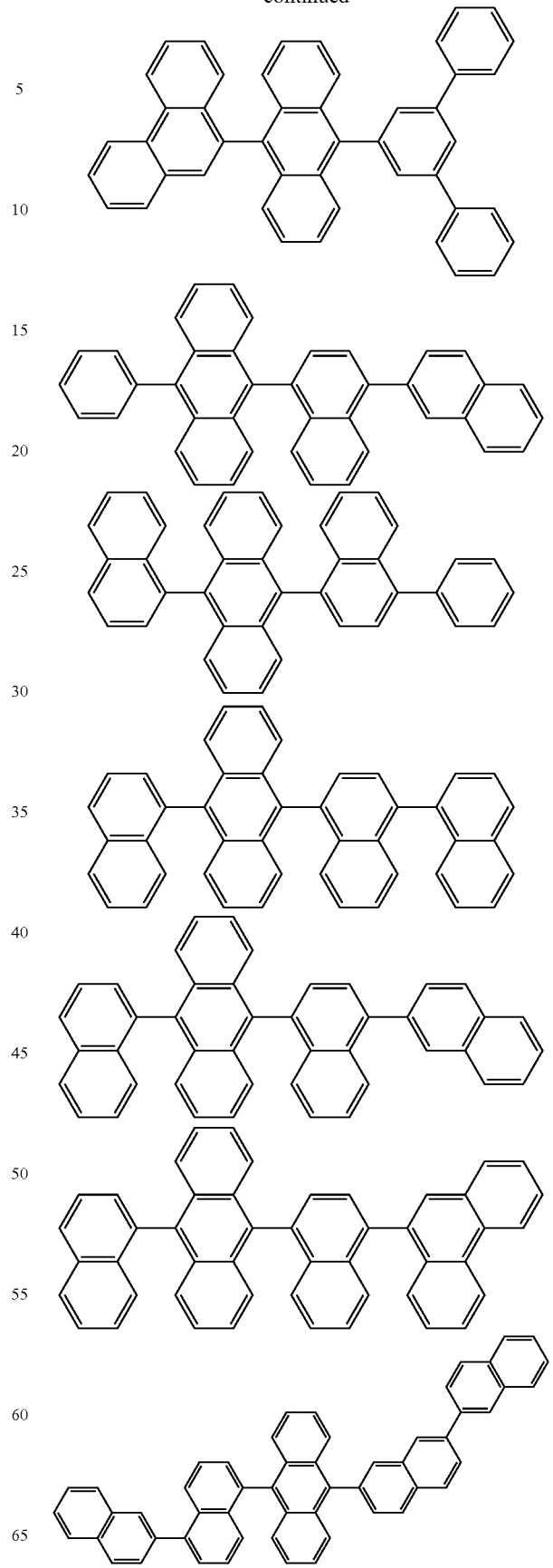

-continued
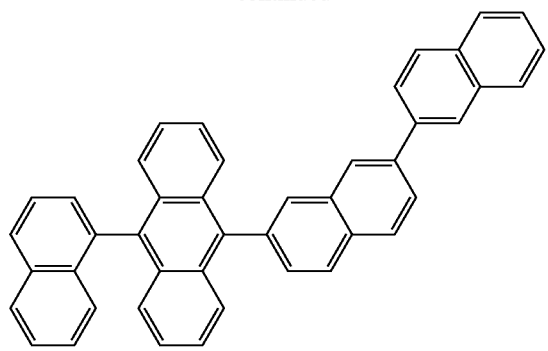
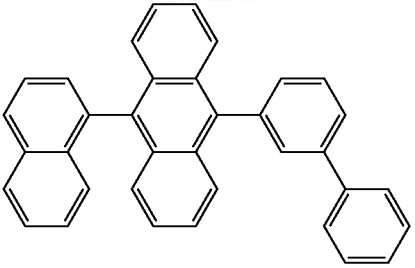

-continued
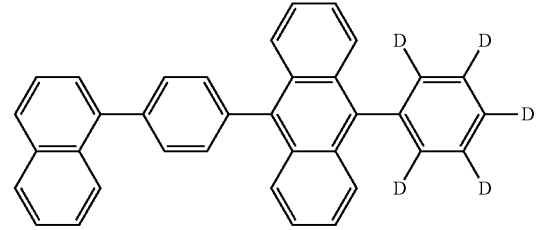
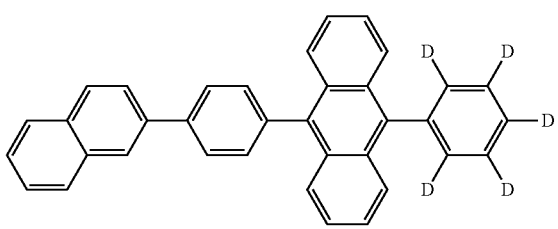
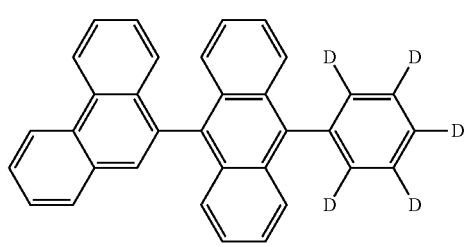
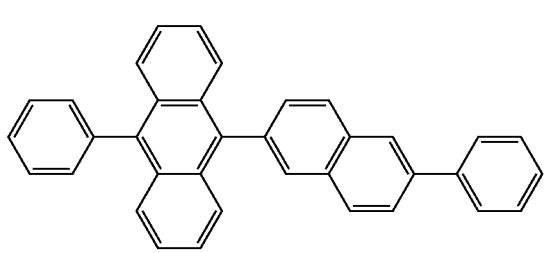
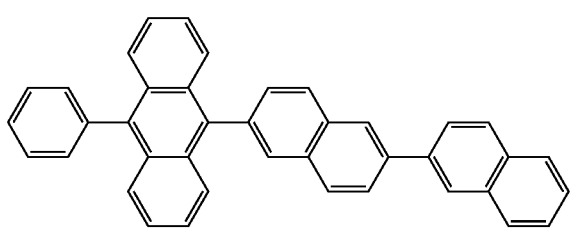
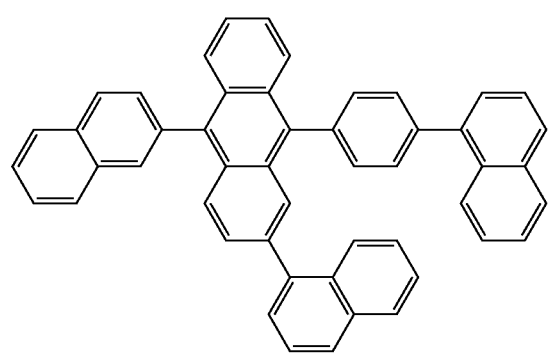
-continued
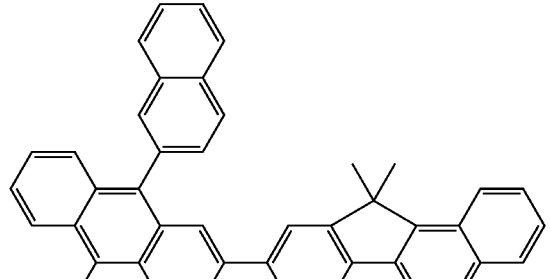
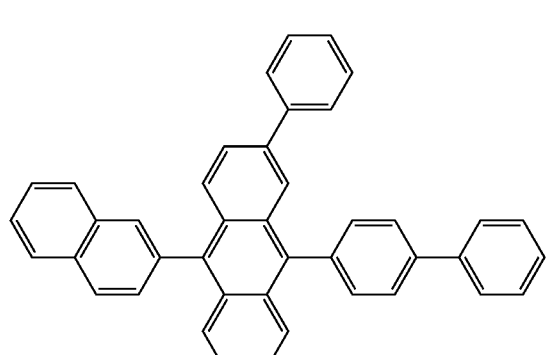
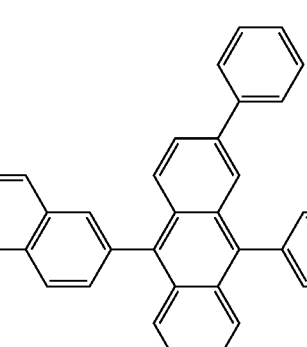
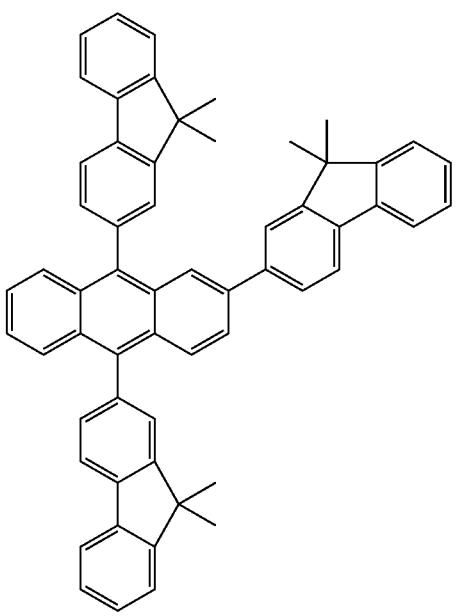

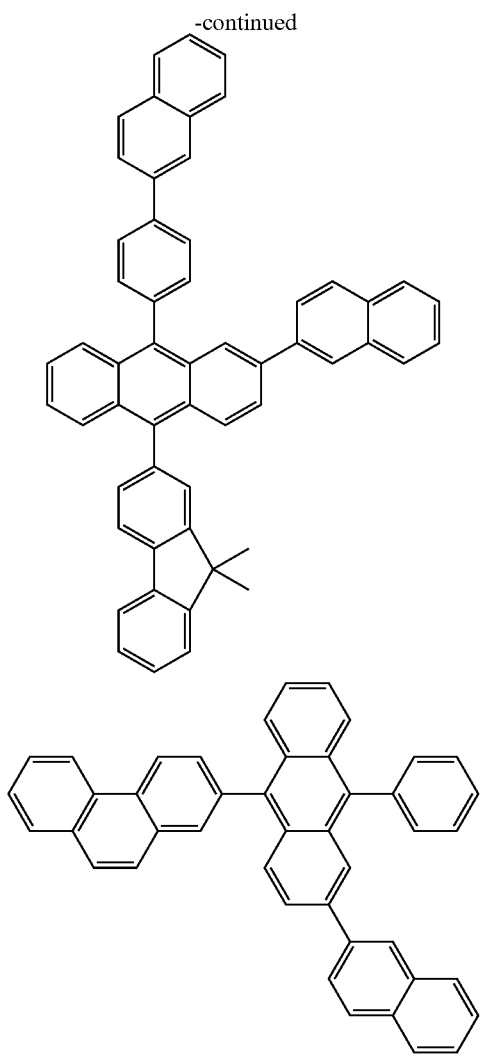

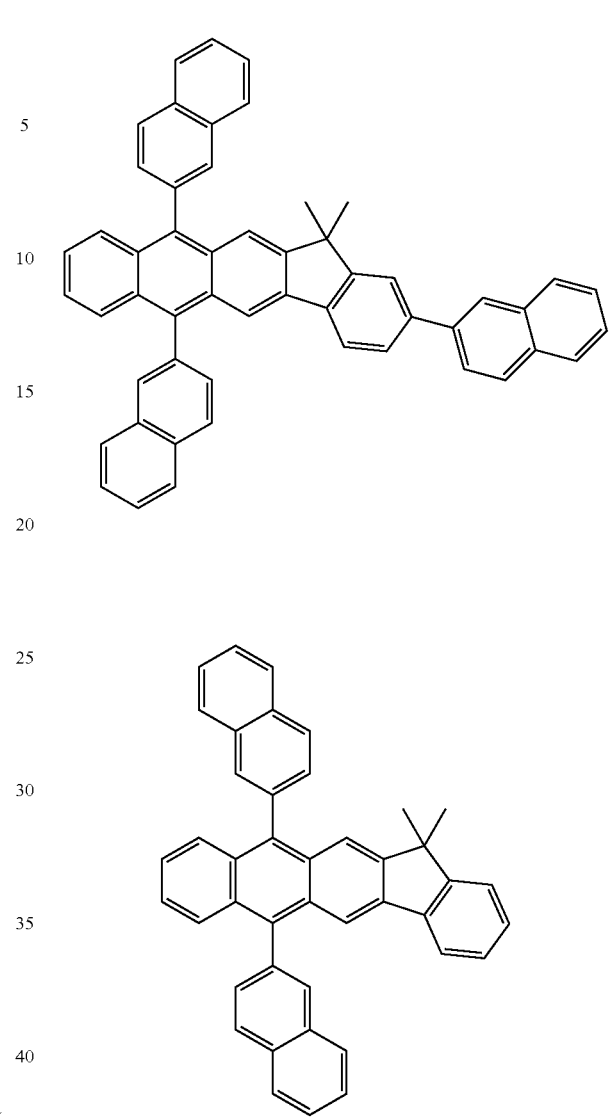

In some embodiments, an anthracene-based compound represented by Formula 401 below may be used as the host:

<Formula 401>

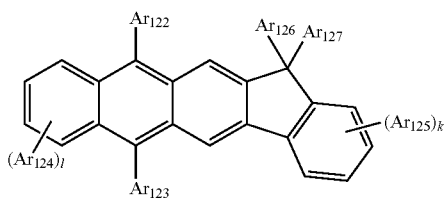

$Ar_{122}$ to $Ar_{125}$ in Formula 401 may be defined as described above with respect to $Ar_{113}$ in Formula 400, and thus detailed descriptions thereof will not be repeated here.

$Ar_{126}$ and $Ar_{127}$ in Formula 401 may each independently be a $C_1$-$C_{10}$ alkyl group (i.e., a methyl group, an ethyl group, or a propyl group).

k and l in Formula 401 may each independently be an integer from 0 to 4. For example, k and l may be 0, 1, or 2.

In some embodiments, the anthracene-based compound represented by Formula 401 may be one of the following compounds represented by Formulas below, but is not limited thereto:

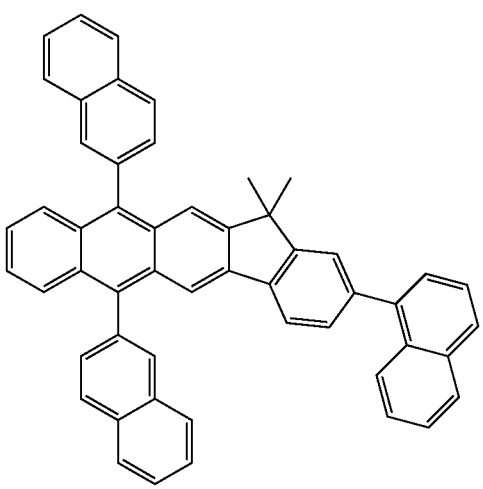

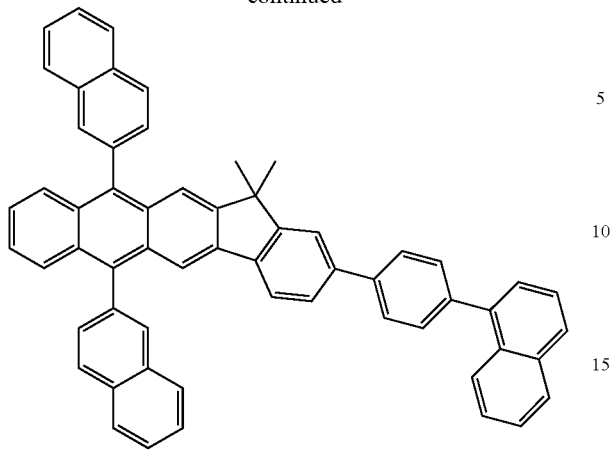
When the OLED is a full color OLED, the EML may be patterned into a red EML, a green EML, and a blue EML.
Meanwhile, at least one the red EML, the green EML, and the blue EML may include one of the following dopants below (ppy=phenylpyridine)
Examples of the blue dopant are the following compounds represented by Formulas below, but are not limited thereto:
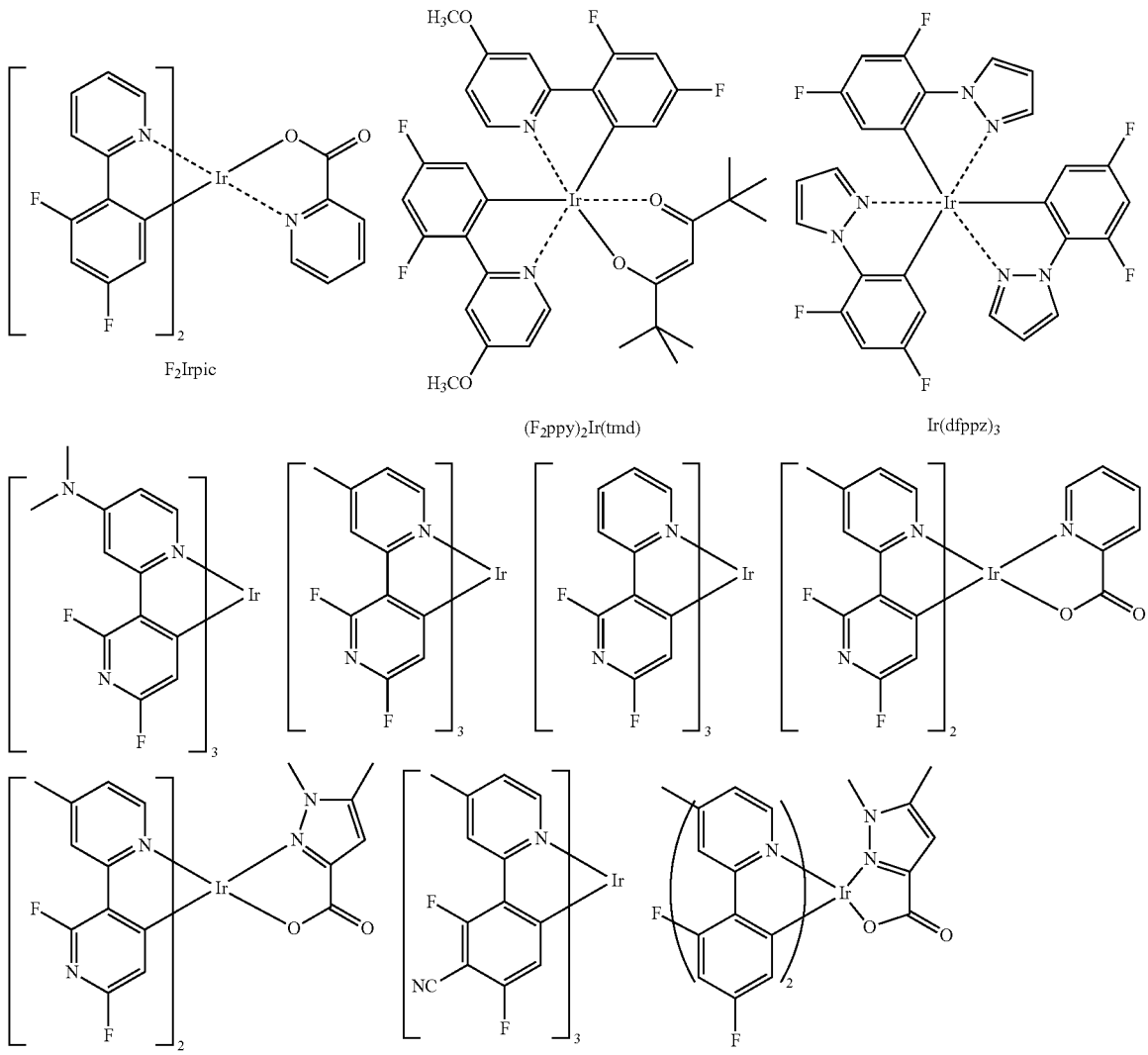

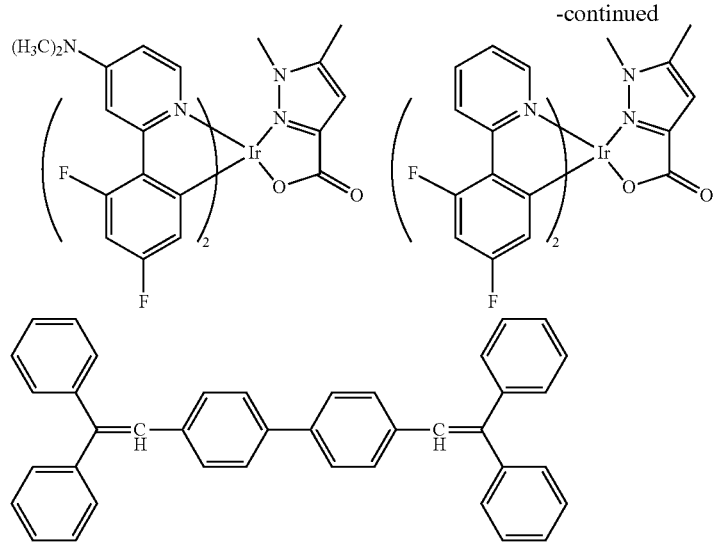
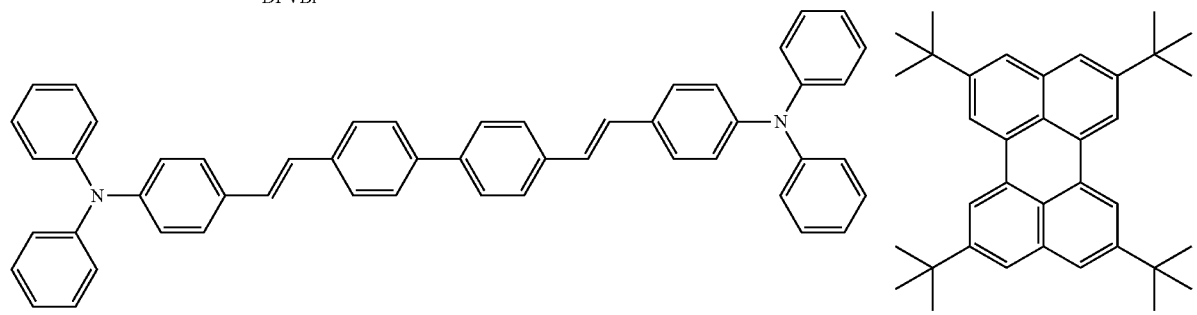
DPVBi
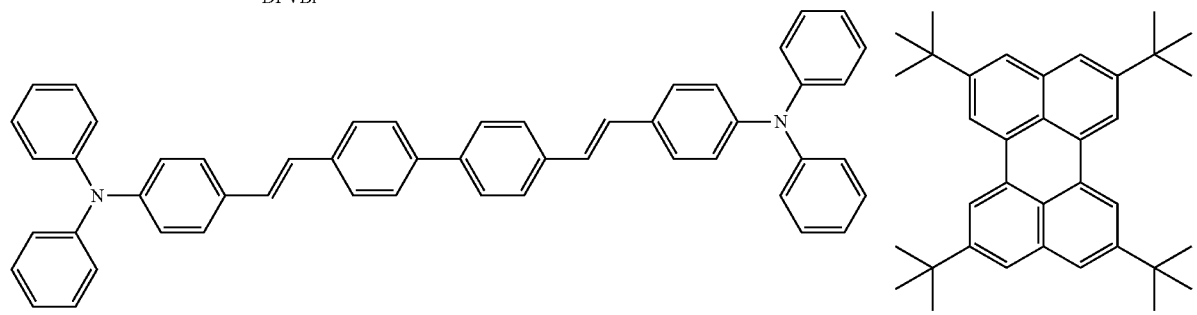
DPAVBi
TBPe
Examples of the red dopant are the following compounds represented by Formulas below, but are not limited thereto:
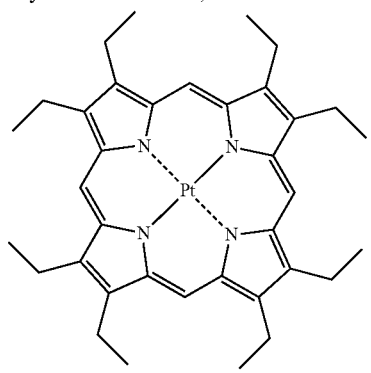
PtOEP
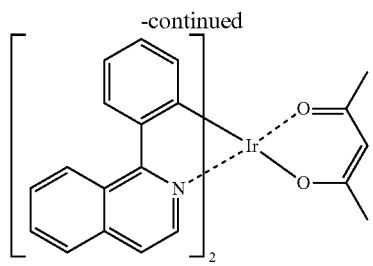
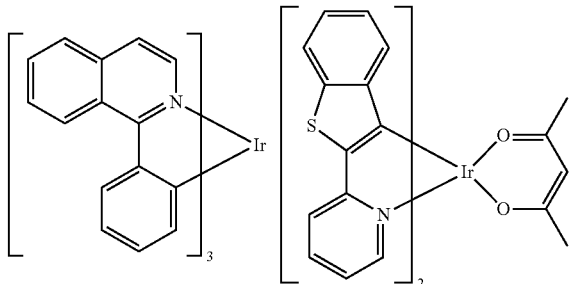
Ir(piq)₃     Btp₂Ir(acac)
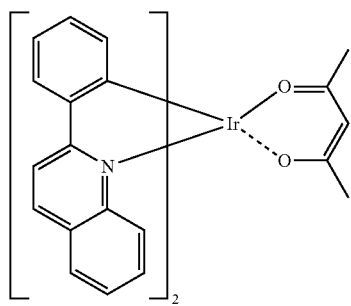
Ir(pq)₂(acac)

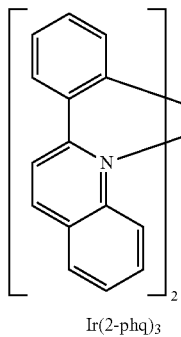
Ir(2-phq)₃
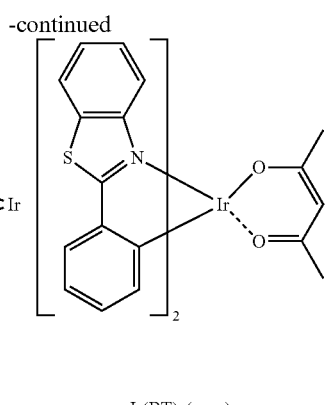
Ir(BT)₂(acac)
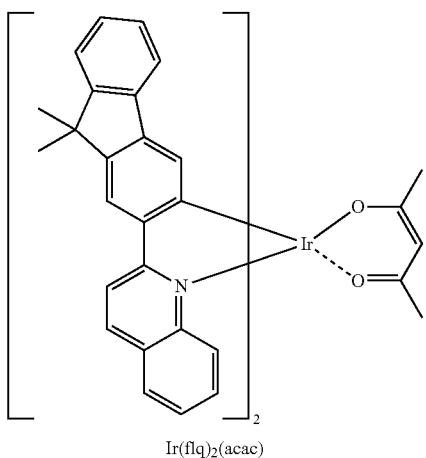
Ir(flq)₂(acac)
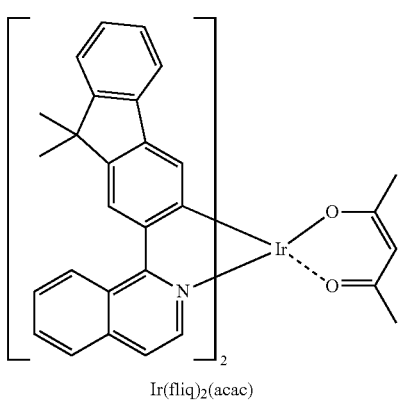
Ir(fliq)₂(acac)
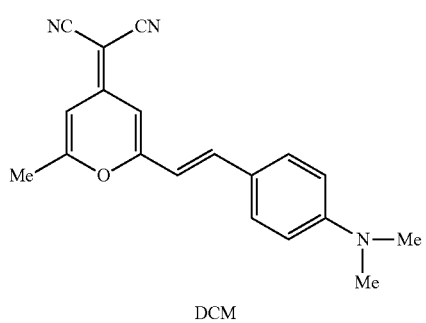
DCM
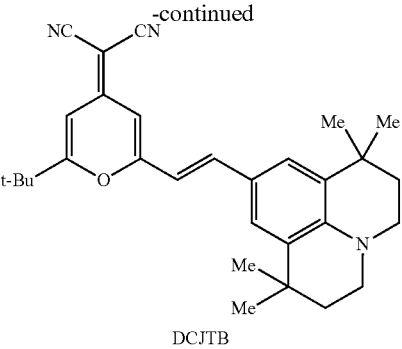
DCJTB
Examples of the green dopant are the following compounds represented by Formulas below, but are not limited thereto:
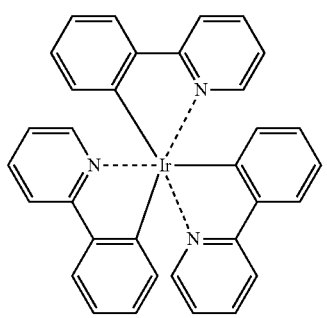
Ir(ppy)₃
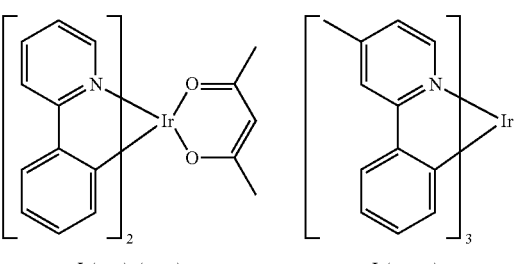
Ir(ppy)₂(acac)    Ir(mpyp)₃
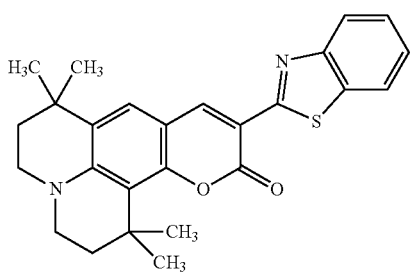
C545T
Examples of dopants that may be used in the EML are Pd complexes or Pt-complexes represented by Formulas below, but are not limited thereto:

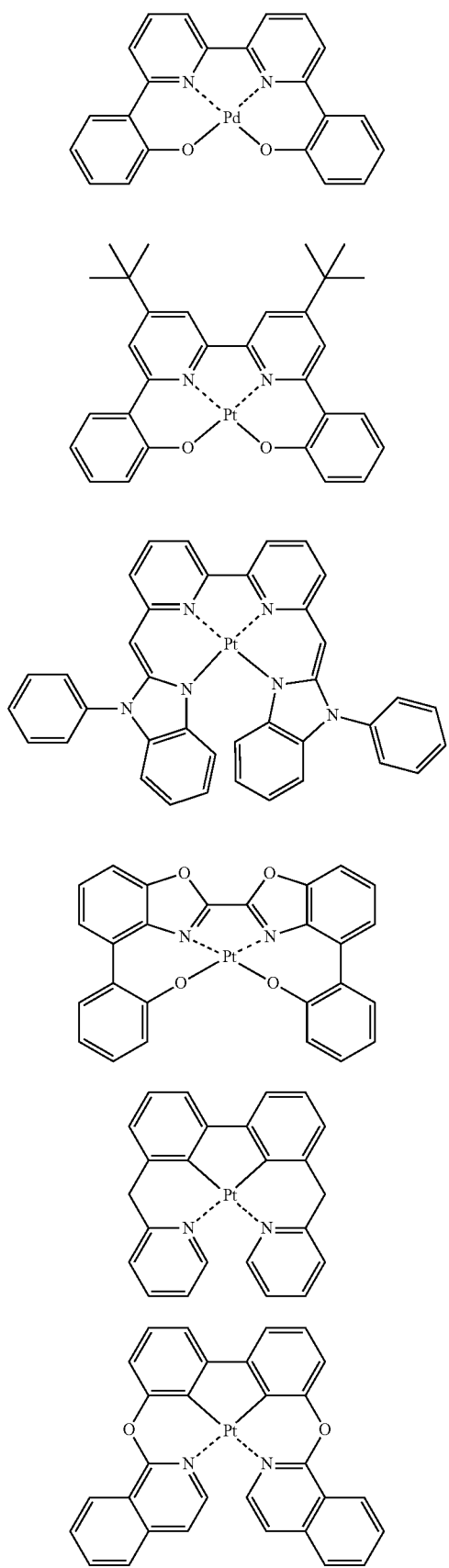
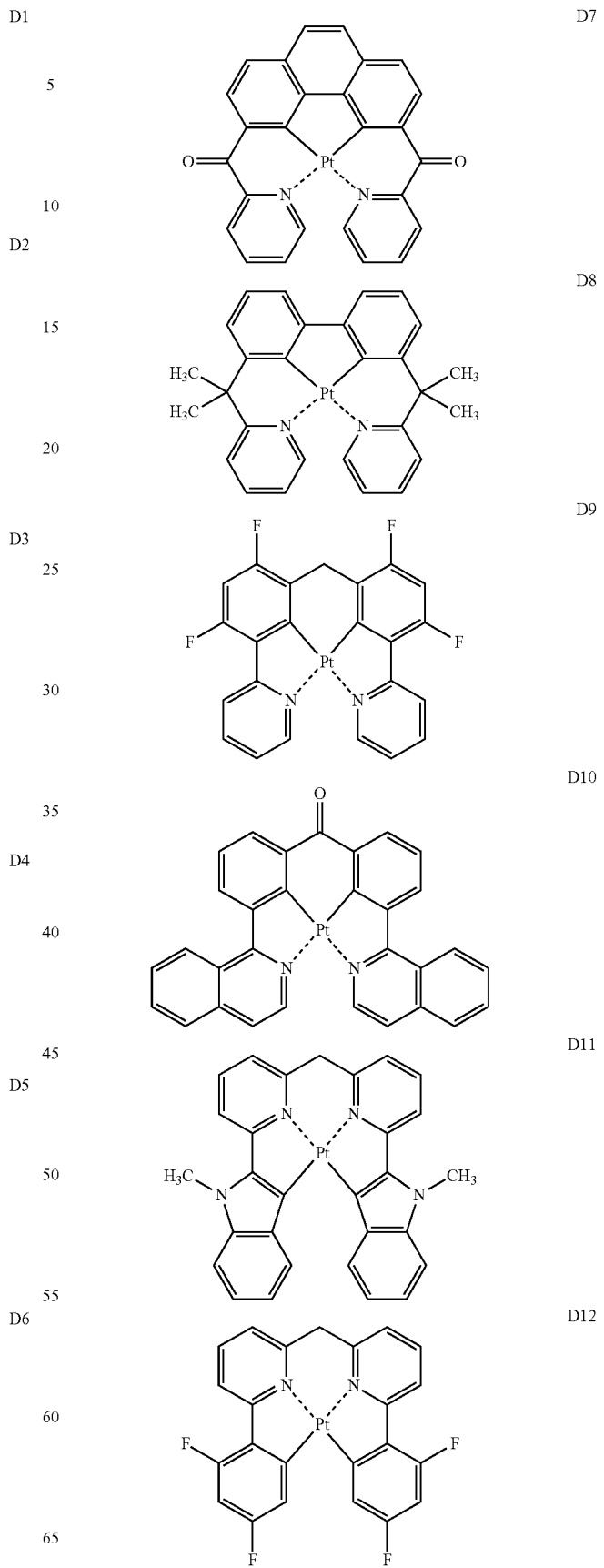

-continued
D13
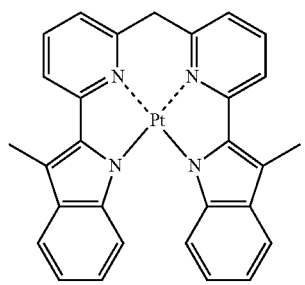
D14
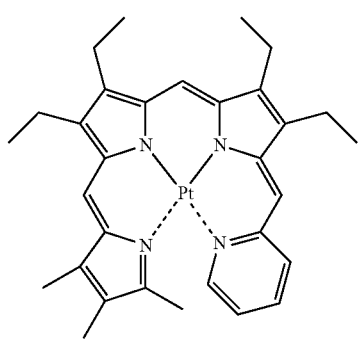
D15
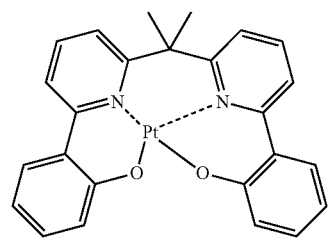
D16
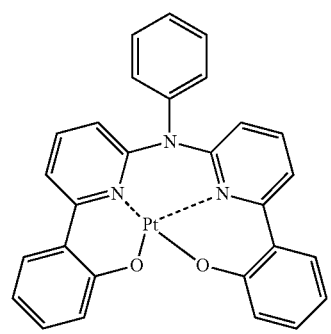
D17
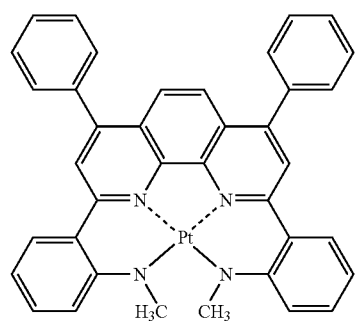
-continued
D18
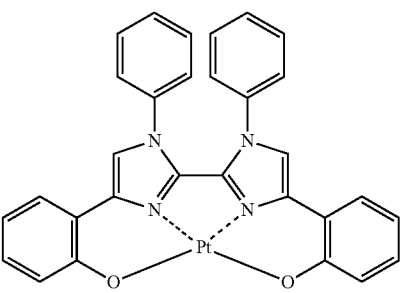
D19
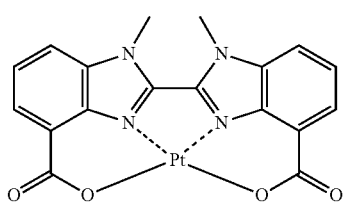
D20
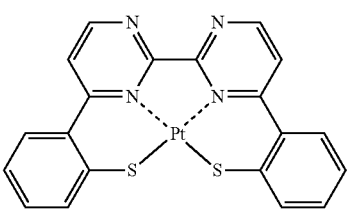
D21
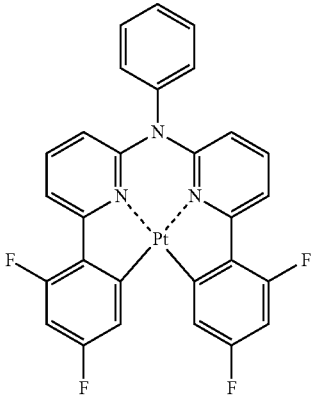
D22
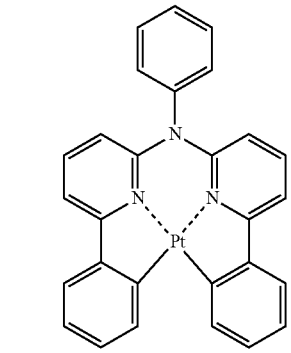

-continued
D23 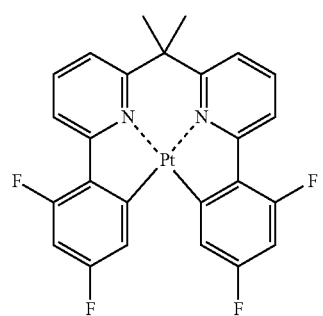
D24 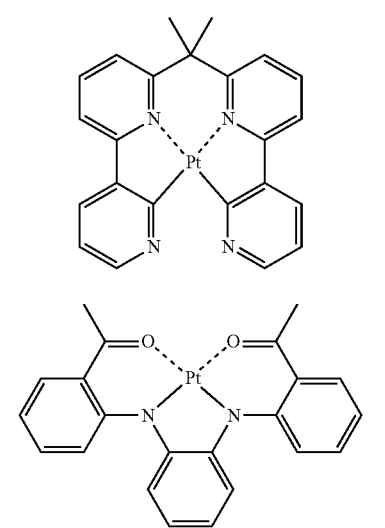
D25
D26 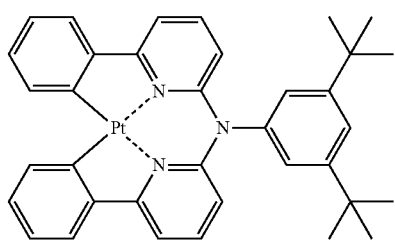
D27 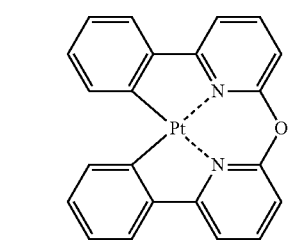
D28 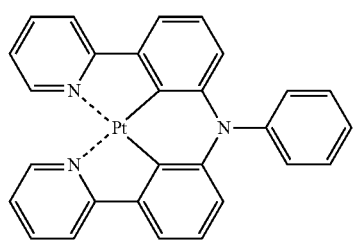
-continued
D29 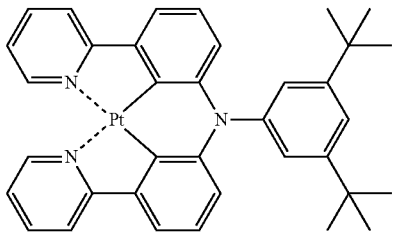
D30 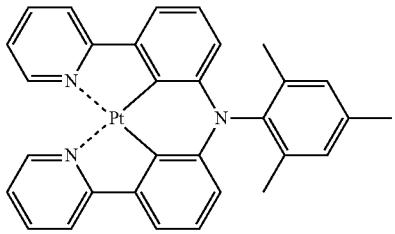
D31 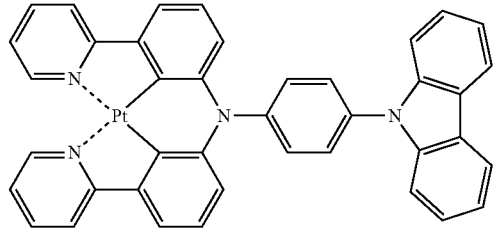
D32 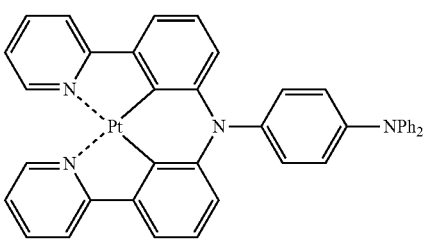
D33 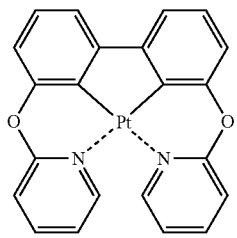
D34 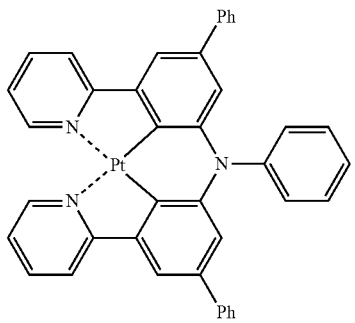

-continued
D35
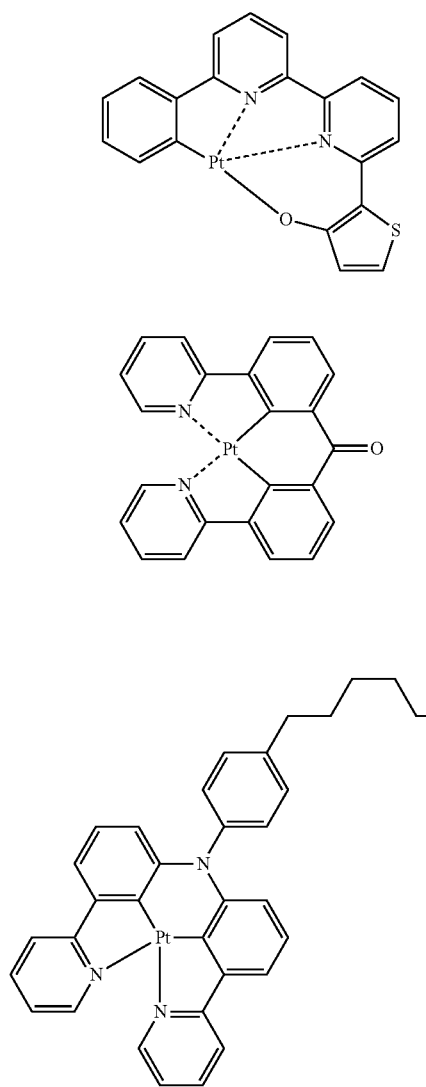
D36
D37
D38
D39
-continued
D40
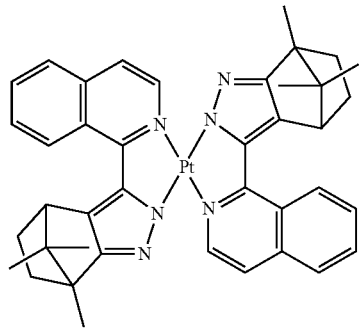
D41
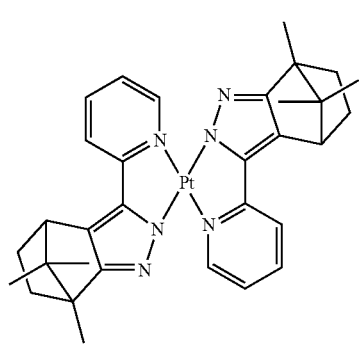
D42
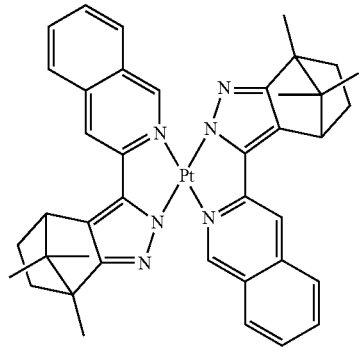
D43
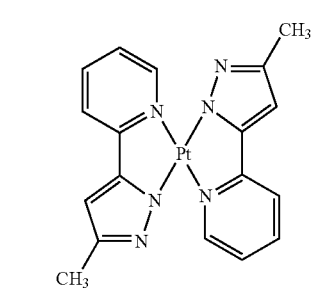
D44
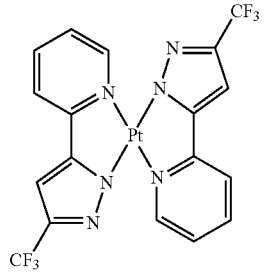

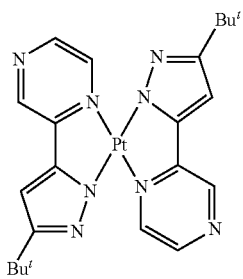
D45
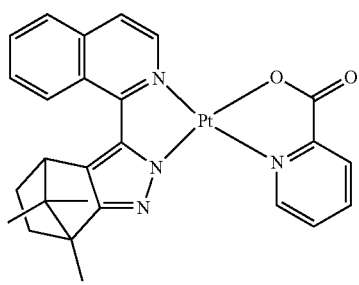
D46
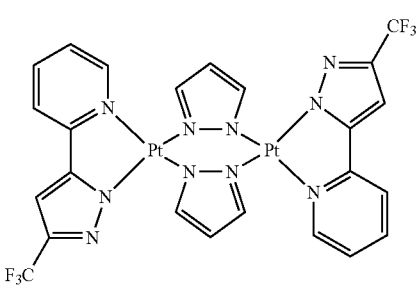
D47
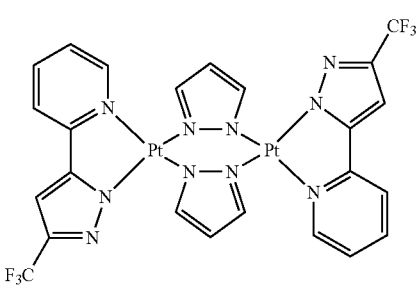
D48
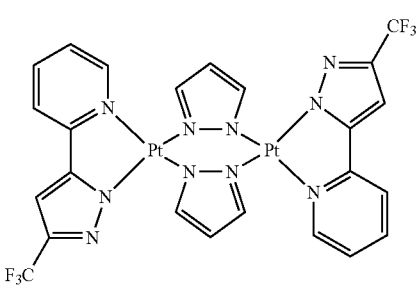
D49
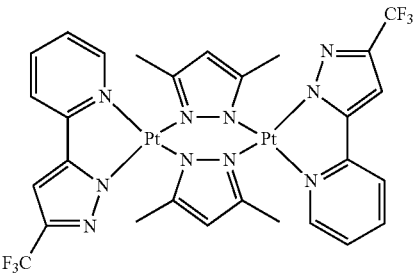
D50
Examples of dopants that may be used in the EML are Os-complexes represented by Formulas below, but are not limited thereto:
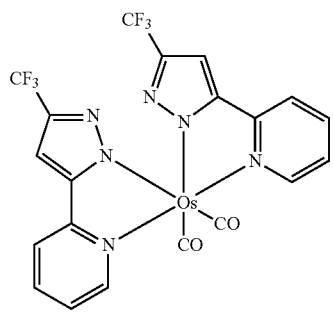
Os(fppz)$_2$(CO)$_2$
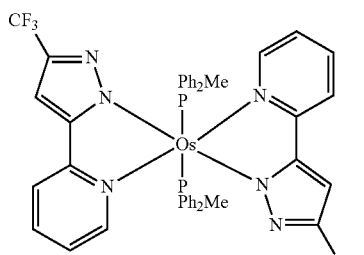
Os(fppz)$_2$(PPh$_2$Me)$_2$
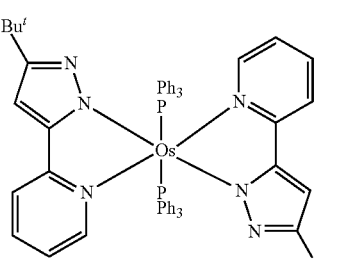
Os(bppz)$_2$(PPh$_3$)$_2$

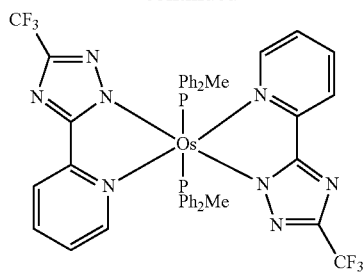

Os(fptz)₂(PPh₂Me)₂

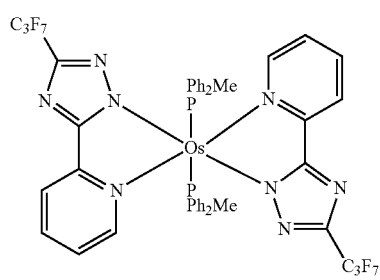

Os(hptz)₂(PPh₂Me₂)₂

When the EML includes a host and a dopant, an amount of the dopant may be in a range from about 0.01 to about 15 parts by weight based on 100 parts by weight of the host, but is not limited thereto.

A thickness of the EML may be in a range from about 100 Å to about 1,000 Å, for example, from about 200 Å to about 600 Å. When the thickness of the EML is within these ranges, the EML may have good light-emitting ability without a substantial increase in driving voltage.

Then, an ETL may be formed on the EML by vacuum deposition, spin coating, casting, or the like. When the ETL is formed using vacuum deposition or spin coating, the deposition and coating conditions may be similar to those for the formation of the HIL, although the deposition and coating conditions may vary depending on a compound that is used to form the ETL. A material for forming the ETL may be any suitable material that can stably transport electrons injected from an electron-injecting electrode (cathode). Examples of the materials for forming the ETL are a quinoline derivative such as tris(8-quinolinolate)aluminum (Alq3), TAZ, BAlq, beryllium bis(benzoquinolin-10-olate) (Bebq₂), 9,10-di (naphthalene-2-yl)anthracene ADN, Compound 201, and

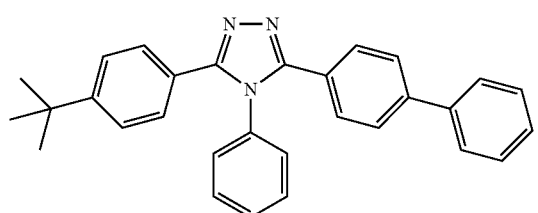

TAZ

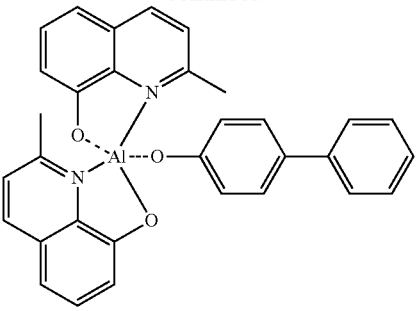

BAlq

<Compound 201>

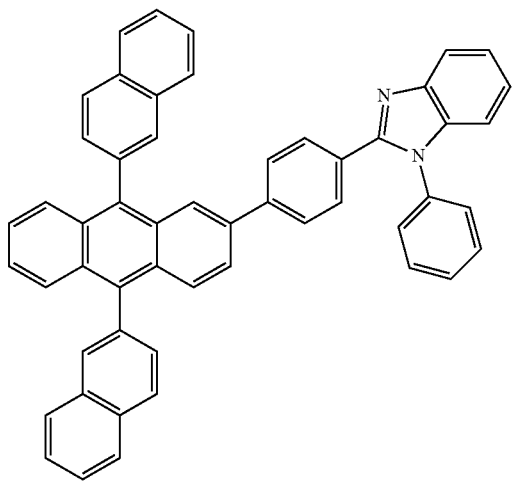

<Compound 202>

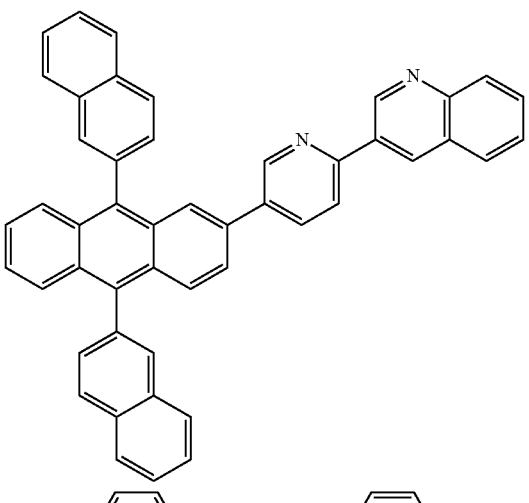

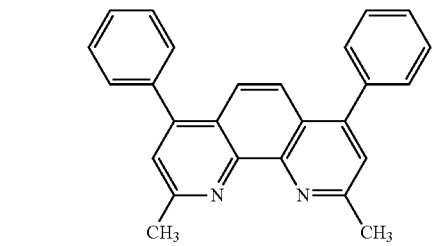

BCP

A thickness of the ETL may be in a range from about 100 Å to about 1,000 Å, for example, from about 150 Å to about 500 Å. When the thickness of the ETL is within these ranges, the ETL may have a satisfactory electron transporting ability without a substantial increase in driving voltage.

In some embodiments, the ETL may further include a metal-containing material, in addition to any suitable electron transporting organic compound.

The metal-containing material may include a lithium (Li) complex. Non-limiting examples of the Li complex are lithium quinolate (LiQ) and Compound 203 below:

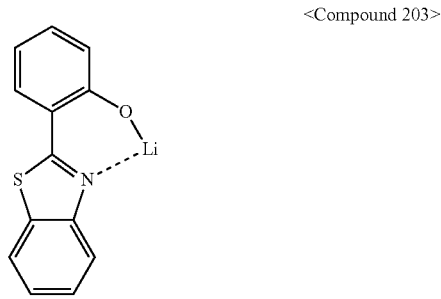

<Compound 203>

Then, an EIL, which facilitates injection of electrons from the cathode, may be formed on the ETL. Any suitable electron-injecting material may be used to form the EIL.

Examples of materials for forming the EIL are LiF, NaCl, CsF, $Li_2O$, and BaO. Deposition conditions of the EIL may be similar to those for the formation of the HIL, although the conditions may vary depending on a material that is used to form the EIL.

A thickness of the EIL may be in a range from about lA to about 100 Å, for example, from about 3 Å to about 90 Å. When the thickness of the EIL is within these ranges, the EIL may have satisfactory electron injection ability without a substantial increase in driving voltage.

A second electrode is disposed on the organic layer. The second electrode may be a cathode that is an electron injection electrode. Here, a material for forming the second electrode may be a metal, an alloy, and an electro-conductive compound, which have a low work function, or a mixture thereof. In this regard, the second electrode may be formed of lithium (Li), magnesium (Mg), aluminum (Al), aluminum-lithium (Al—Li), calcium (Ca), magnesium-indium (Mg—In), magnesium-silver (Mg—Ag), or the like, and may be formed as a thin film type transmission electrode. In some embodiments, to manufacture a top-emission light-emitting diode, the transmission electrode may be formed of indium tin oxide (ITO) or indium zinc oxide (IZO).

An OLED according to an example embodiment has already been described above with reference to FIG. 1, but is not limited to the structure illustrated in FIG. 1.

In addition, when the EML is formed using a phosphorescent dopant, to prevent diffusion of triplet excitons or holes toward the ETL, a hole blocking layer (HBL) may be formed between the ETL and the EML or between the E-functional layer and the EML by a method such as, for example, vacuum deposition, spin coating, casting, LB, or the like. When the HBL is formed using vacuum deposition or spin coating, the deposition and coating conditions may be similar to those for the formation of the HIL, although the conditions for deposition and coating may vary depending on the material that is used to form the HBL. Any suitable hole-blocking material may be used. Non-limiting examples of hole-blocking materials are oxadiazole derivatives, triazole derivatives, and phenanthroline derivatives. For example, BCP illustrated below may be used as a material for the HBL.

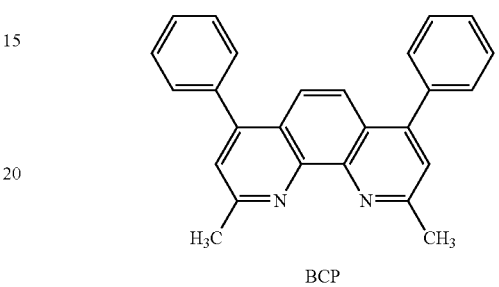

BCP

A thickness of the HBL may be in a range from about 20 Å to about 1,000 Å, for example, from about 30 Å to about 300 Å. When the thickness of the HBL is within these ranges, the HBL may have an improved hole blocking ability without a substantial increase in driving voltage.

The OLED according to an embodiment may be provided in various types of flat panel display devices such as passive matrix OLED devices and active matrix OLED devices. In particular, when the OLED is provided in an active matrix OLED, the first electrode on the substrate, which acts as a pixel electrode, may be electrically connected to a source electrode or a drain electrode of a thin-film transistor (TFT). In addition, the OLED may be provided in a flat panel display device having double-sided screens.

In some embodiments the organic layer of the organic light-emitting device may be formed of the compound of Formula 1 by using a deposition method or may be formed using a wet process of coating a solution of the compound of Formula 1.

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

EXAMPLE

Synthesis Example 1

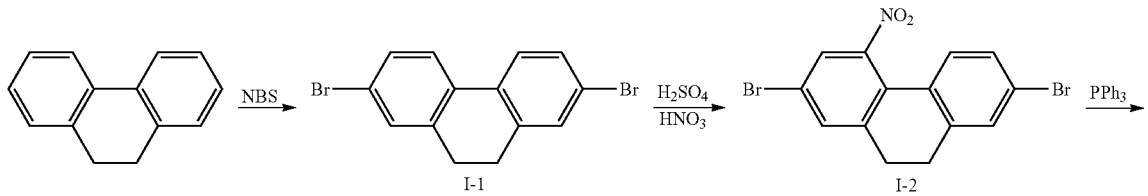

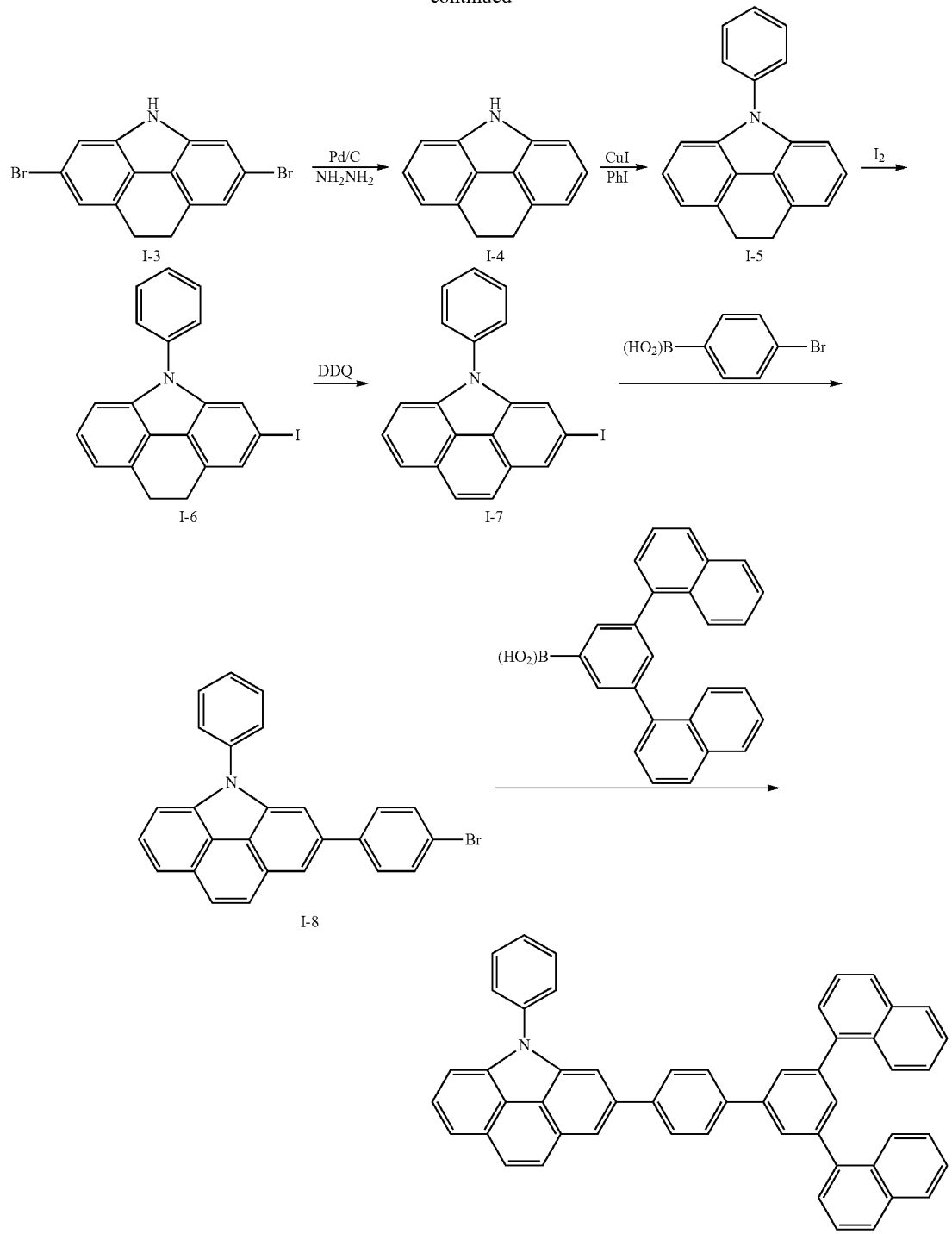

Synthesis of Intermediate I-1

After dissolving 10.0 g (55.4 mmol) of 9,10-dihydrophenanthrene, 21.8 g (121.0 mmol) of N-bromosuccinimide, and 0.5 g (2.7 mmol) of p-TsOH in 30 mL of acetonitrile, the reaction solution was stirred at a temperature of 50° C. for 12 hours. The reaction solution was cooled to room temperature, and then stirred for 30 minutes to precipitate crystals. The crystals obtained by a pressure reducing filter were washed with methanol to obtain 8.4 g (Yield: 45%) of Intermediate I-1 in gray. The obtained compound was identified by LC-MS ($C_{14}H_{10}Br_2$ $M^+$ 336.9).

Synthesis of Intermediate I-2

After completely dissolving 5.0 g (15.0 mmol) of Intermediate I-1 in 50 mL of dichloromethane, 1.7 g (30.0 mmol) of nitric acid was added thereto at room temperature. Then, 1.5 g (15.0 mmol) of sulfuric acid was slowly added thereto, and then the reaction solution was stirred at a temperature of 30° C. for 6 hours. After completion of the reaction, the reaction solution was cooled to room temperature, 50 mL of methanol was added thereto, and then stirred for 2 hours to precipitate crystals. The crystals obtained by a pressure reducing filter were washed with methanol to obtain 5.2 g (Yield: 90%) of Intermediate I-2 in yellow. The obtained compound was identified by LC-MS ($C_{14}H_9Br_2NO_2$ $M^+$ 381.9).

Synthesis of Intermediate I-3

After completely dissolving 4.6 g (12.0 mmol) of Intermediate I-2 in 30 mL of o-dichlorobenzene and heating the reaction solution, 4.7 g (18.0 mmol) of triphenylphosphine was added thereto. Then the reaction solution was stirred at a temperature of 180° C. for 3 hours. After the reaction solution was cooled to room temperature, a solvent was evaporated and the residual was separation-purified by silica gel column chromatography, and then washed with methanol to obtain 2.9 g (Yield: 70%) of Intermediate I-3 in white. The obtained compound was identified by LC-MS ($C_{14}H_9Br_2N$ $M^+$ 349.9).

Synthesis of Intermediate I-4

After dissolving 10 g (28.5 mmol) of Intermediate I-3 and 0.03 g (0.28 mmol) of Pd/c (10%) in 100 mL of ethanol at room temperature, a temperature of the reaction solution was increased up to 50° C., 5.48 g (171 mmol) of hydrazine was added thereto, and then stirred for 24 hours. The reaction solution was cooled to room temperature, and washed with acetone. Then, 100 mL of ice water was added thereto to obtains 3.63 g (Yield: 66%) of Intermediate I-4 in white. The obtained compound was identified by LC-MS ($C_{14}H_{11}N$ M+ 194.1).

Synthesis of Intermediate I-5

After dissolving 1.93 g (10.0 mmol) of Intermediate I-4, 2.5 g (12.0 mmol) of iodobenzene, 0.2 g (1.0 mmol) of 1,10-phenanthroline, 0.2 g (2.0 mmol) of CuI, and 4.1 g (30.0 mmol) of $K_2CO_3$ in 30 mL of N,N-dimethylformamide (DMF), the reaction solution was stirred at a temperature of 80° C. for 24 hours. The reaction solution was cooled to room temperature, and then, was extracted three times with 30 mL of water and 40 mL of diethyl ether. An organic layer obtained therefrom was dried with magnesium sulfate, a solvent was evaporated, and the residual was separation-purified by silica gel column chromatography to obtain 2.39 g (Yield: 89%) of Intermediate I-5. The obtained compound was identified by LC-MS ($C_{20}H_{15}N$ $M^+$ 270.1).

Synthesis of Intermediate I-6

After completely dissolving 10 g (37.1 mmol) of Intermediate I-5 in 100 ml of dichloromethane, 3.58 g (14.1 mmol) of iodine and 2.38 g (11.13 mmol) of $KIO_3$ were added thereto to 1/5 split. The reaction solution was stirred for 6 hours and then washed with methanol to obtain 8.06 g (Yield: 55%) of Intermediate I-6. The obtained compound was identified by LC-MS ($C_{20}H_{14}IN$ M+ 396.1).

Synthesis of Intermediate I-7

After dissolving 10 g (25.3 mmol) of Intermediate I-6 in 100 ml of toluene in an oxygen atmosphere, 1.57 g (7.6 mmol) of 2,3-dichloro-5,6-dicyano-1,4-benzoquinone and 0.52 g (7.6 mmol) of $NaNO_2$ were added thereto at room temperature. The reaction solution was stirred at a temperature of 110° C. for 6 hours, and after cooling the reaction solution to room temperature, a solvent was evaporated and the residual was separation-purified by silica gel column chromatography to obtain 8.94 g (Yield: 90%) of Intermediate I-7. The obtained compound was identified by LC-MS ($C_{20}H_{12}IN$ M+ 394.0)

Synthesis of Intermediate I-8

After dissolving 3.93 g (10 mmol) of Intermediate I-7, 2 g (10.0 mmol) of 4-bromophenyl-boronic acid, 0.58 g (0.5 mmol) of Pd(PPh_3)_4, and 4.15 g (30.0 mmol) $K_2CO_3$ in 40 mL of $THF/H_2O$ (volume ratio 2/1), the reaction solution was stirred at a temperature of 70° C. for about 5 hours. The reaction solution was cooled to room temperature, 40 mL of water was added thereto, and then, was extracted three times with 50 mL of ethyl ether. An organic layer obtained therefrom was dried with magnesium sulfate, a solvent was evaporated, and the residual was separation-purified by silica gel column chromatography to obtain 3.67 g (Yield: 87%) of Intermediate I-8. The obtained compound was identified by LC-MS ($C_{26}H_{16}BrN$: M+ 422.0).

Synthesis of Compound 3

5.44 g (Yield: 81%) of Compound 3 was synthesized in the same manner as used to synthesize Intermediate I-8, except that Intermediate I-8 was used instead of Intermediate I-7 and 3,5-di(naphthylene-1-yl)phenyl-boronic acid was used instead of 4-bromophenyl-boronic acid. The obtained compound was identified by MS/FAB and $^1$H NMR ($C_{52}H_{33}N$ cal. 671.26. found 673.26).

$^1$H NMR (CDCl_3, 400 MHz) δ=8.08 (m, 1H), 8.01-7.99 (m, 1H), 7.98 (m, 1H), 7.94 (t, 1H), 7.92-7.88 (m, 4H), 7.85-7.84 (d, 2H), 7.82-7.81 (m, 2H), 7.78-7.74 (m, 3H), 7.58-7.53 (m, 4H), 7.51 (s, 1H), 7.48-7.45 (m, 3H), 7.40-7.36 (m, 4H), 7.32-7.31 (d, 1H), 7.29 (d, 2H), 7.25-7.21 (m, 1H), 7.16-7.12 (m, 2H)

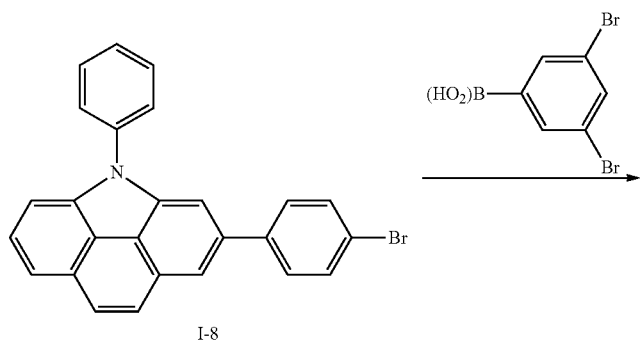

I-8

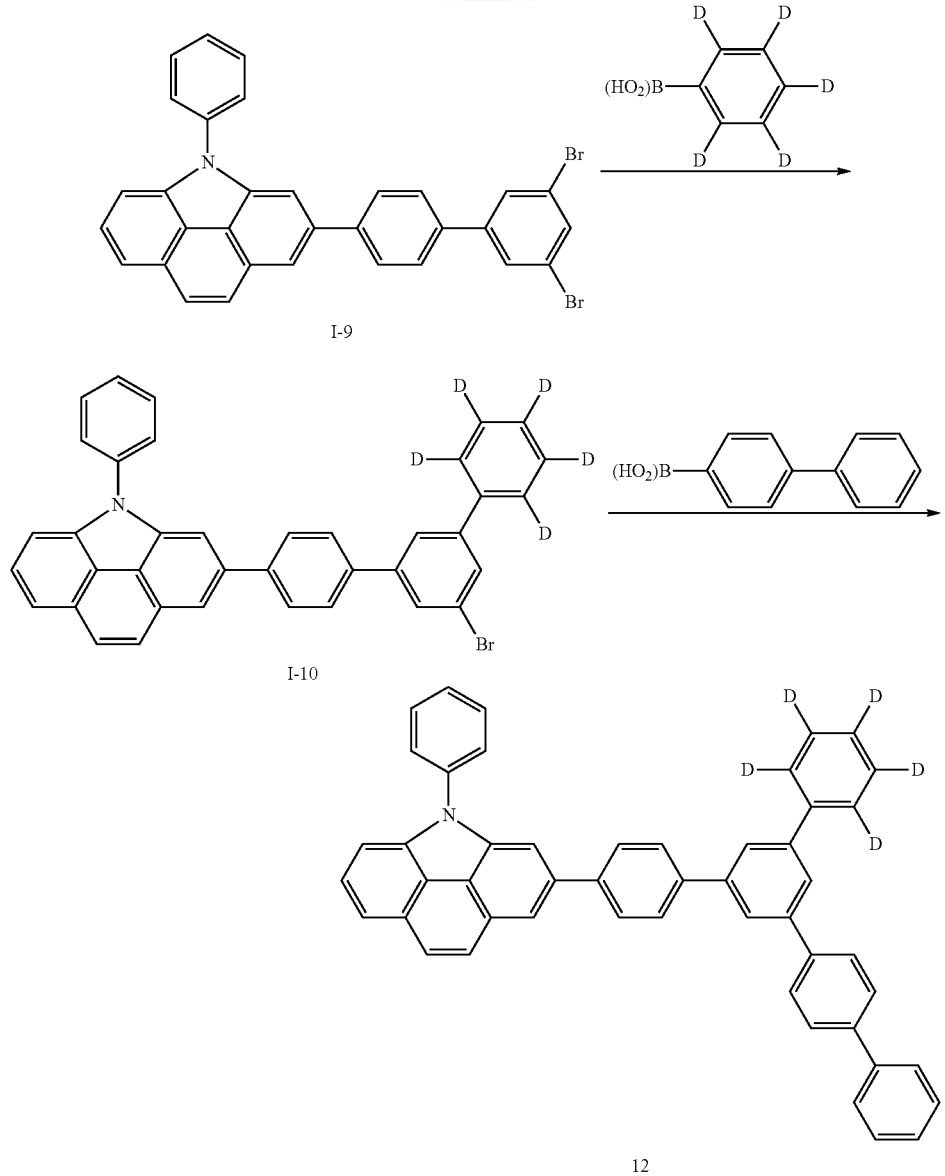

Synthesis of Intermediate I-9

4.62 g (Yield: 80%) of Intermediate I-9 was synthesized in the same manner as used to synthesize Intermediate I-8, except that Intermediate I-8 was used instead of Intermediate I-7 and 3,5-dibromophenyl-boronic acid was used instead of 4-bromophenyl-boronic acid. The obtained compound was identified by LC-MS ($C_{32}H_{19}Br_2N$ M+ 575.99).

Synthesis of Intermediate I-10

4.46 g (Yield: 77%) of Intermediate I-10 was synthesized in the same manner as used to synthesize Intermediate I-8, except that Intermediate I-9 was used instead of Intermediate I-7 and phenyl-boronic acid-d5 was used instead of 4-bromophenyl-boronic acid. The obtained compound was identified by LC-MS ($C_{38}H_{19}D_5Br_2N$ M+ 579.1).

Synthesis of Compound 12

5.35 g (Yield: 82%) of Compound 12 was synthesized in the same manner as used to synthesize Intermediate I-8, except that Intermediate I-10 was used instead of Intermediate I-7 and biphenyl-4-yl-boronic acid was used instead of 4-bromophenyl-boronic acid. The obtained compound was identified by MS/FAB and $^1$H NMR ($C_{50}H_{28}D_5N$ cal. 652.29. found 653.29).

$^1$H NMR (CDCl$_3$, 400 MHz) δ=8.08 (m, 1H), 7.94-7.88 (m, 4H), 7.78-7.75 (m, 2H), 7.73-7.67 (m, 6H), 7.62-7.45 (m, 10H), 7.42-7.35 (m, 3H), 7.32 (d, 1H), 7.29 (d, 1H)

By using the same method of the synthetic methods above and suitable Intermediate materials (i.e., a substance with corresponding Br substituent, a substance with corresponding B(OH)$_2$ substituent, and the like), other additional compounds were synthesized. Results of $^1$H NMR and MS/FAB of the obtained compounds are shown in Table 1 below.

In addition to the compounds shown in Table 1, it would be apparent to those of skill in the art to easily recognize the same method and materials as those described above.

TABLE 1

| Cmpd | ¹H NMR (CDCl₃, 400 MHz) | MS/FAB found | MS/FAB calc. |
|---|---|---|---|
| 3 | δ = 8.08 (m, 1H), 8.01-7.99 (m, 1H), 7.98 (m, 1H), 7.94 (t, 1H), 7.92-7.88 (m, 4H), 7.85-7.84 (d, 2H), 7.82-7.81 (m, 2H), 7.78-7.74 (m, 3H), 7.58-7.53 (m, 4H), 7.51 (s, 1H), 7.48-7.45 (m, 3H), 7.40-7.36 (m, 4H), 7.32-7.31 (d, 1H), 7.29 (d, 2H), 7.25-7.21 (m, 1H), 7.16-7.12 (m, 2H) | 672.26 | 671.26 |
| 7 | δ = 8.08 (m, 1H), 7.94-7.88 (m, 4H), 7.81 (m, 1H), 7.79 (m, 1H), 7.78-7.77 (m, 2H), 7.72 (s, 1H), 7.70-7.69 (d, 2H), 7.62 (t, 1H), 7.58-7.52 (m, 5H), 7.49-7.45 (m, 3H), 7.40-7.35 (m, 3H), 7.33 (d, 1H), 7.32 (t, 1H), 7.29-7.28 (m, 3H), 7.16-7.09 (m, 4H), 1.57 (s, 12H) | 804.36 | 803.36 |
| 10 | δ = 8.08 (m, 1H), 7.94-7.88 (m, 4H), 7.78-7.76 (m, 1H), 7.69-7.67 (m, 6H), 7.64-7.63 (t, 1H), 7.60 (m, 2H), 7.58-7.51 (m, 5H), 7.49-7.45 (m, 3H), 7.40-7.36 (m, 2H), 7.32-7.29 (dd, 2H), 0.35 (s, 18H) | 716.31 | 715.31 |
| 12 | δ = 8.08 (m, 1H), 7.94-7.88 (m, 4H), 7.78-7.75 (m, 2H), 7.73-7.67 (m, 6H), 7.62-7.45 (m, 10H), 7.42-7.35 (m, 3H), 7.32 (d, 1H), 7.29 (d, 1H) | 653.29 | 652.29 |
| 15 | δ = 8.08 (m. 1H), 7.94-7.89 (m, 4H), 7.81-7.78 (m, 1H), 7.76-7.73 (m, 5H), 7.70 (t, 1H), 7.67 (t, 3H), 7.62-7.46 (m, 12H), 7.42-7.35 (m, 3H), 7.33-7.28 (m, 3H), 7.16-7.09 (m, 2H), 1.57 (s, 6H) | 764.32 | 763.32 |
| 21 | δ = 8.08 (m, 1H), 7.94-7.93 (d, 2H), 7.85 (dd, 1H), 7.83 (dd, 1H), 7.78-7.77 (m, 1H), 7.76-7.72 (m, 5H), 7.58-7.53 (m, 5H), 7.49-7.35 (m, 13H), 7.32 (t, 1H), 7.29-7.28 (m, 3H) | 752.32 | 751.32 |
| 24 | δ = 8.71-8.69 (m, 1H), 8.18 (d, 1H), 8.02-8.00 (m, 1H), 7.94-7.93 (d, 2H), 7.82-7.80 (m, 2H), 7.76-7.72 (m, 6H), 7.67-7.64 (m, 2H), 7.57-7.54 (m, 6H), 7.49-7.36 (m, 12H), 7.32-7.24 (m, 4H), 7.01-6.98 (m, 2H) | 798.31 | 797.31 |
| 27 | δ = 8.05 (m, 1H), 7.97-7.94 (dd, 1H), 7.87-7.84 (dd, 1H), 7.78-7.76 (m, 1H), 7.74-7.73 (t, 1H), 7.69-7.65 (m, 6H), 7.61 (s, 1H), 7.59-7.53 (m, 3H), 7.49-7.36 (m, 12H), 7.32-7.30 (dd, 1H), 7.27-7.23 (m, 4H), 7.20-7.17 (dd, 2H), 7.13-7.07 (m, 7H) | 812.32 | 811.32 |
| 28 | δ = 8.80-8.18 (m, 3H), 8.14-8.13 (m, 2H), 8.06-8.04 (m, 1H), 8.01-7.91 (m, 6H), 7.78-7.76 (dd, 1H), 7.74-7.71 (m, 3H), 7.68-7.66 (m, 5H), 7.58-7.53 (m, 3H), 7.49-7.35 9m, 12H), 7.32-7.30 (dd, 1H) | 748.29 | 747.29 |
| 29 | δ = 8.34-8.33 (m, 2H), 8.08-8.07 (d, 2H), 7.89-7.88 (t, 1H), 7.83-7.82 (dd, 2H), 7.78-7.76 (m, 2H), 7.73-7.71 (m, 2H), 7.61-7.51 (m, 8H), 7.49 (s, 1H), 7.48-7.45 (m, 5H), 7.39-7.36 (m, 6H), 7.33-7.31 (m, 4H), 7.30-7.28 (m, 2H), 7.08-7.05 (m, 2H), 2.43 (s, 3H) | 875.33 | 874.33 |
| 33 | δ = 8.31 (m, 1H), 8.14 (m, 1H), 7.94-7.93 (m, 1H), 7.82-7.80 (q, 2H), 7.78-7.77 (m, 2H), 7.76 (m, 1H), 7.72-7.66 (m, 4H), 7.61-7.54 (m, 6H), 7.51 (s, 1H), 7.49-7.36 (m, 14H), 7.32-7.31 (d, 1H), 7.30-7.29 (d, 1H), 7.26-7.22 (t, 1H) | 761.29 | 760.29 |
| 34 | δ = 8.31 (m, 2H), 8.14 (m, 1H), 7.94-7.93 (m, 1H), 7.90-7.89 (t, 1H), 7.86 (d, 2H), 7.78-7.75 (m, 3H), 7.72-7.67 (m, 2H), 7.61-7.54 (m, 9H), 7.51 (s, 1H), 7.49-7.45 (m, 10H), 7.40-7.35 (m, 8H), 7.32-7.30 (dd, 2H), 7.26-7.22 (m, 1H) | 950.35 | 949.35 |
| 38 | δ = 8.31 (m, 2H), 8.00-7.99 (t, 1H), 7.94-7.90 (m, 5H), 7.87 (d, 2H), 7.83-7.82 (m, 2H), 7.78-7.74 (m, 4H), 7.61-7.53 (m, 8H), 7.51 (s, 1H), 7.49-7.45 (m, 7H), 7.40-7.36 (m, 6H), 7.31-7.30 (dd, 2H), 7.25-7.21 (m, 2H), 7.16-7.13 (m, 2H) | 937.35 | 936.35 |
| 40 | δ = 8.31 (m, 2H), 7.93-7.92 (t, 1H), 7.88-7.87 (d, 2H), 7.79-7.78 (m, 2H), 7.76-7.75 (m, 4H), 7.73-7.72 (m, 2H), 7.70-7.67 (m, 5H), 7.62-7.45 (m, 22H), 7.42-7.35 (m, 6H), 7.31-7.30 (dd, 2H) | 989.38 | 988.38 |
| 41 | δ = 8.08 (m, 1H), 7.94-7.88 (m, 4H), 7.78-7.75 (m, 1H), 7.69-7.68 (d, 2H), 7.65-7.64 (t, 1H), 7.60-7.54 (m, 7H), 7.49-7.45 (m, 3H), 7.40-7.35 (m, 2H), 7.32 (d, 1H), 7.29 (q, 1H), 7.00-6.98 (m, 4H), 3.84 (s, 6H) | 632.25 | 631.25 |
| 43 | δ = 8.08 (m, 1H), 8.03-8.02 (d, 1H), 8.01-8.00 (d, 1H), 7.97 (m, 1H), 7.93-7.88 (m, 5H), 7.78-7.75 (m, 1H), 7.73-7.66 (m, 9H), 7.58-7.53 (m, 5H), 7.51 (d, 1H), 7.49-7.45 (m, 2H), 7.43-7.41 (m, 2H), 7.39-7.35 (m, 2H), 7.32 (d, 1H), 7.29 (m, 1H) | 752.25 | 751.25 |
| 44 | δ = 8.08 (m, 1H), 7.96-7.89 (m, 5H), 7.86-7.85 (m, 3H), 7.78-7.74 (m, 4H), 7.70-7.65 (m, 3H), 7.63-7.60 (m, 5H), 7.56-7.48 (m, 5H), 7.46-7.39 (m, 7H), 7.35-7.34 (t, 1H), 7.32-7.31 (m, 1H), 7.29 (d, 1H), 7.25 (s, 1H), 7.23 (d, 1H), 7.21 (s, 1H) | 774.31 | 773.31 |
| 46 | δ = 8.08 (m, 1H), 7.94-7.88 (m, 4H), 7.81-7.79 (m, 1H), 7.76-7.72 (m, 5H), 7.70 (t, 1H), 7.67 (t, 3H), 7.63-7.58 (m, 4H), 7.55-7.47 (m, 9H), 7.41-7.38 (m, 2H), 7.35-7.30 (m, 5H), 7.29-7.28 (m, 2H), 7.16-7.09 (m, 2H), 1.57 (s, 6H) | 840.36 | 839.36 |

TABLE 1-continued

| Cmpd | $^1$H NMR (CDCl$_3$, 400 MHz) | MS/FAB found | MS/FAB calc. |
|---|---|---|---|
| 47 | δ = 8.71-8.69 (m, 1H), 8.18 (m, 1H), 8.02-8.00 (ss, 1H), 7.94-7.93 (d, 2H), 7.82-7.80 (m, 2H), 7.76-7.72 (m, 6H), 7.67-7.64 (m, 3H), 7.57-7.54 (m, 3H), 7.48-7.40 (m, 8H), 7.36-7.25 (m, 7H), 7.21-7.15 (m, 3H), 7.01-6.98 (m, 1H), 2.70-2.65 (m, 2H), 1.26 (s, 3H) | 826.34 | 825.34 |
| 50 | δ = 8.87-8.86 (m, 1H), 8.60-8.58 (m, 1H), 8.08 (m, 1H), 7.93-7.89 (m, 5H), 7.81-7.80 (d, 2H), 7.77-7.67 (m, 10H), 7.57-7.53 (m, 3H), 7.49-7.44 (m, 4H), 7.40-7.35 (m, 2H), 7.32-7.31 (d, 1H), 7.30-7.29 (m, 1H) | 674.25 | 673.25 |
| 55 | δ = 8.94 (m, 1H), 8.67-8.66 (m, 1H), 8.08-8.03 (m, 2H), 7.93-7.88 (m, 4H), 7.83-7.73 (m, 6H), 7.58-7.45 (m, 8H), 7.40-7.28 (m, 6H), 7.15-7.09 (m, 2H), 1.57 (s, 6H) | 689.29 | 688.29 |

Example 1

An anode was prepared by cutting a Corning 15 Ω/cm$^2$ (1,200 Å) ITO glass substrate to a size of 50 mm×50 mm×0.7 mm, sonicated in isopropyl alcohol for 5 minutes and in pure water for 5 minutes, and then cleaned by irradiation of ultraviolet rays for 30 minutes, and exposed to ozone. The resulting glass substrate was loaded into a vacuum deposition device.

2-TNATA was vacuum deposited on the anode to a thickness of 600 Å to form an HIL, and 4'-bis[N-(1-naphthyl)-N-phenylamino]biphenyl (hereinafter, NPB) as a hole transporting compound was vacuum-deposited on the HIL to a thickness of 300 Å.

Compound 3 of Formula 1 above as a general blue fluorescent host, and 4,4'-bis[2-(4-(N,N-diphenylamino)phenyl)vinyl]biphenyl (hereinafter, DPAVBi) as a general blue fluorescent dopant, were co-deposited at a weight ratio of 98:2 on the HTL to form an EML having a thickness of 300 Å.

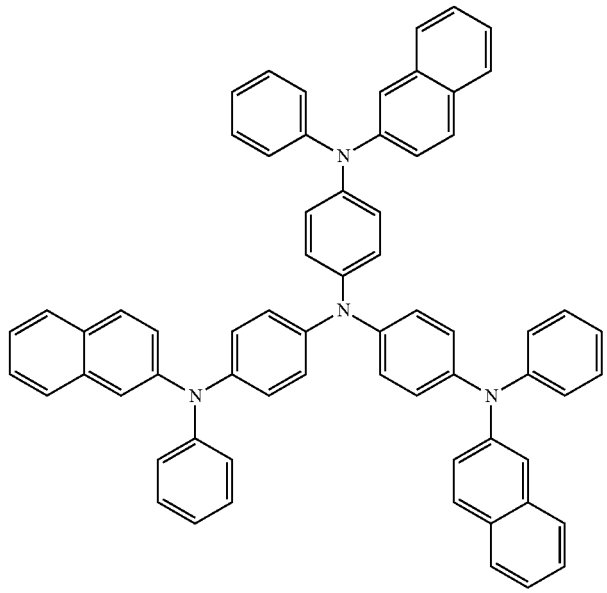

2-TNATA

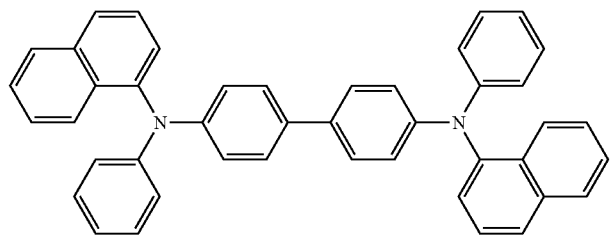

NPB

-continued

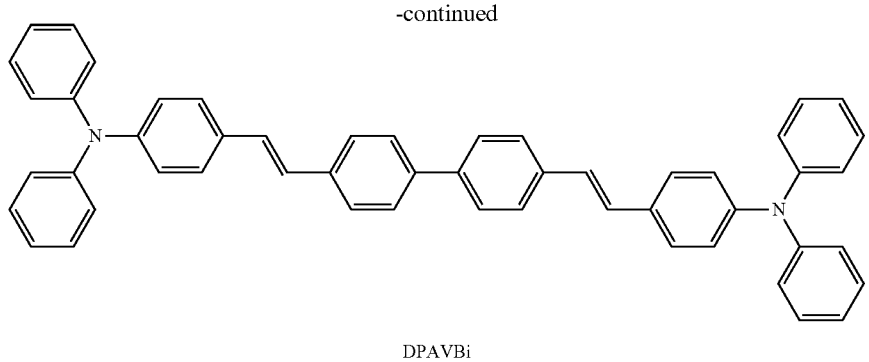

DPAVBi

Next, $Alq_3$ was deposited on the EML to form an ETL to a thickness of 300 Å, and then LiF, which is a halogenated alkali metal, was deposited on the ETL to form an EIL to a thickness of 10 Å. Then, Al (cathode electrode) was vacuum-deposited on the EIL to a thickness of 3,000 Å, thereby forming a LiF/Al electrode and completing the manufacture of an OLED.

The OLED had a driving voltage of about 6.44 V at a current density of 50 mA/cm$^2$, a luminosity of 2,800 cd/m$^2$, a luminescent efficiency of 5.60 cd/A and a half life-span (hr@100 mA/cm$^2$) of about 287 hours.

Example 2

An OLED was manufactured in the same manner as in Example 1, except that Compound 21 was used instead of Compound 3 to form the EML The OLED had a driving voltage of about 6.61 V at a current density of 50 mA/cm$^2$, a luminosity of 2,820 cd/m$^2$, a luminescent efficiency of 5.64 cd/A, and a half life-span (hr@100 mA/cm$^2$) of about 261 hours.

Example 3

An OLED was manufactured in the same manner as in Example 1, except that Compound 24 was used instead of Compound 3 to form the EML.

The OLED had a driving voltage of about 6.52 V at a current density of 50 mA/cm$^2$, a luminosity of 2,965 cd/m$^2$, a luminescent efficiency of 5.93 cd/A, and a half life-span (hr@100 mA/cm$^2$) of about 307 hours.

Example 4

An OLED was manufactured in the same manner as in Example 1, except that Compound 27 was used instead of Compound 3 to form the EML.

The OLED had a driving voltage of about 6.48 V at a current density of 50 mA/cm$^2$, a luminosity of 2,895 cd/m$^2$, a luminescent efficiency of 5.79 cd/A, and a half life-span (hr@100 mA/cm$^2$) of about 302 hours.

Example 5

An OLED was manufactured in the same manner as in Example 1, except that Compound 40 was used instead of Compound 3 to form the EML.

The OLED had a driving voltage of about 6.59 V at a current density of 50 mA/cm$^2$, a luminosity of 2,950 cd/m$^2$, a luminescent efficiency of 5.90 cd/A, and a half life-span (hr@100 mA/cm$^2$) of about 322 hours.

Example 6

An OLED was manufactured in the same manner as in Example 1, except that Compound 44 was used instead of Compound 3 to form the EML.

The OLED had a driving voltage of about 6.56 V at a current density of 50 mA/cm$^2$, a luminosity of 2,890 cd/m$^2$, a luminescent efficiency of 5.78 cd/A, and a half life-span (hr@100 mA/cm$^2$) of about 304 hours.

Example 7

An OLED was manufactured in the same manner as in Example 1, except that Compound 50 was used instead of $Alq_3$ to form the ETL.

The OLED had a driving voltage of about 6.05 V at a current density of 50 mA/cm$^2$, a luminosity of 3,110 cd/m$^2$, a luminescent efficiency of 6.12 cd/A, and a half life-span (hr@100 mA/cm$^2$) of about 315 hours.

Example 8

An OLED was manufactured in the same manner as in Example 7, except that Compound 55 was used instead of Compound 50 to form the ETL.

The OLED had a driving voltage of about 6.11 V at a current density of 50 mA/cm$^2$, a luminosity of 3,025 cd/m$^2$, a luminescent efficiency of 6.05 cd/A, and a half life-span (hr@100 mA/cm$^2$) of about 299 hours.

Comparative Example 1

An OLED was manufactured in the same manner as in Example 1, except that the general 9,10-di-naphthalene-2-yl-anthracene (hereinafter, referred as DNA) was used instead of Compound 1 to form the EML.

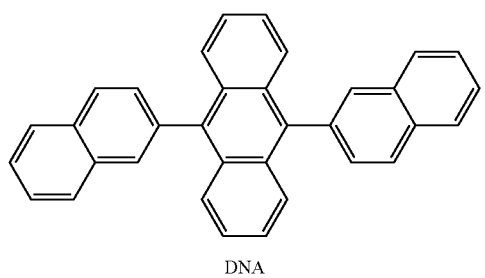 [SMILES: c1ccc2cc(-c3c4ccccc4c(-c4ccc5ccccc5c4)c4ccccc34)ccc2c1]

DNA

The OLED had a driving voltage of about 7.35 V at a current density of 50 mA/cm$^2$, a luminosity of 2,065 cd/m$^2$, a luminescent efficiency of 4.13 cd/A, and a half life-span (hr@100 mA/cm$^2$) of about 145 hours.

When the compound of Formula 1 according to the present example embodiment was used as a host material of a blue EML or an electron-transporting material, compared to the general DNA and Alq$_3$, the OLED including the compound had an improved driving voltage and showed excellent I-V-L characteristics with greatly improved efficiency, in particularly with regard to lifetime improvement. Results of representative properties and lifetimes of the compounds are summarized and shown in Table 2 below:

TABLE 2

|  | Light-emitting layer material, electron-transporting material | Driving voltage (V) | Current density (mA/cm$^2$) | Luminosity (cd/m$^2$) | Luminescent efficiency (cd/A) | Luminescence color | Half-life lifetime (hr @ 100 mA/cm$^2$) |
|---|---|---|---|---|---|---|---|
| Example 1 | Compound 3 | 6.44 | 50 | 2,800 | 5.60 | Blue | 287 hr |
| Example 2 | Compound 21 | 6.61 | 50 | 2,820 | 5.64 | Blue | 261 hr |
| Example 3 | Compound 24 | 6.52 | 50 | 2,965 | 5.93 | Blue | 307 hr |
| Example 4 | Compound 27 | 6.48 | 50 | 2,895 | 5.79 | Blue | 302 hr |
| Example 5 | Compound 40 | 6.59 | 50 | 2,950 | 5.90 | Blue | 322 hr |
| Example 6 | Compound 44 | 6.56 | 50 | 2,890 | 5.78 | Blue | 304 hr |
| Example 7 | Compound 50 | 6.05 | 50 | 3,110 | 6.12 | Blue | 315 hr |
| Example 8 | Compound 55 | 6.11 | 50 | 3,025 | 6.05 | Blue | 299 hr |
| Comparative Example 1 | DNA | 7.35 | 50 | 2,065 | 4.13 | Blue | 145 hr |

By way of summation and review, a typical diode may have a structure including a substrate, an anode formed on the substrate, and a hole transport layer (HTL), an emission layer (EML), an electron transport layer (ETL), and a cathode which are sequentially stacked on the substrate. The HTL, the EML, and the ETL may be organic thin films formed of organic compounds.

An operating principle of an OLED having the above-described structure may be as follows.

When a voltage is applied between the anode and the cathode, holes injected from the anode may move to the EML via the HTL, and electrons injected from the cathode may move to the EML via the ETL. The holes and electrons (carriers) may recombine in the EML to generate excitons. When the excitons drop from an excited state to a ground state, light may be emitted.

There is interest in a material having improved electrical stability, high charge-transfer or emission capability, a high glass transition temperature that is high enough to prevent crystallization, in regard to existing unimolecular materials.

As described above, a compound of Formula 1 according to an embodiment may provide excellent light-emitting capability, and thus may be suitable for fluorescent and phosphorescent devices, e.g., of a color of red, green, blue, or white. Therefore, an organic light-emitting device having high efficiency, low driving voltages, high luminance, and long lifetime may be manufactured using the compound.

Embodiments may provide a compound and an organic light-emitting diode (OLED) including the same. The compound may provide excellent electrical properties, high charge-transporting abilities, or high light-emitting abilities. The compound may be a material having a high glass transition temperature and may be capable of preventing crystallization, and may be effectively used as an electron-transporting material that is suitable for a fluorescent and a phosphorescent diode of emitting colors such as red, green, blue, and white. Therefore, an OLED including the compound and having high efficiency, low voltage, high brightness, and long lifetime characteristics may be provided.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:
1. A compound represented by Formula 1 below:

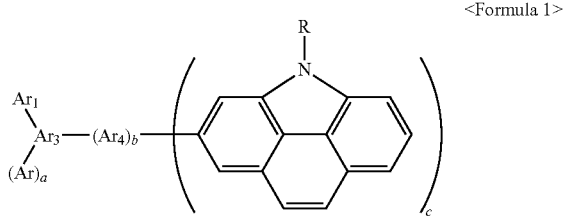

<Formula 1> wherein, in Formula 1,
R is represented by Formula 5a or Formula 5b below:

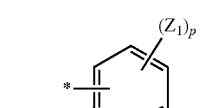

5a

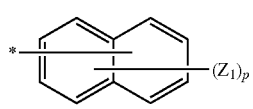

5b wherein, in Formulas 5a and 5b,
Z$_1$ is a hydrogen atom, a deuterium atom, a substituted or unsubstituted C$_1$-C$_{20}$ alkyl group, a substituted or unsubstituted C$_6$-C$_{20}$ aryl group, a substituted or unsubstituted $C_3$-$C_{20}$ heteroaryl group, a substituted or unsubstituted $C_6$-$C_{20}$ condensed polycyclic group, a halogen atom, a cyano group, a nitro group, a hydroxyl group, or a carboxyl group;

p is an integer from 1 to 7; and

* is a binding site;

$Ar_1$, $Ar_2$, $Ar_3$, and $Ar_4$ are each independently a substituted or unsubstituted $C_6$-$C_{60}$ aryl group, a substituted or unsubstituted $C_{10}$-$C_{60}$ condensed polycyclic group, or a substituted or unsubstituted $C_3$-$C_{60}$ heteroaryl group;

a is an integer from 0 to 2, b is an integer from 0 to 4, c is an integer from 1 to 3, and when b is 2 or more, $Ar_4$ is identical to or different from each other.

2. The compound of claim 1, wherein $Ar_1$ and $Ar_2$ are each independently one of the following compounds represented by Formulas 2a to 2e below:

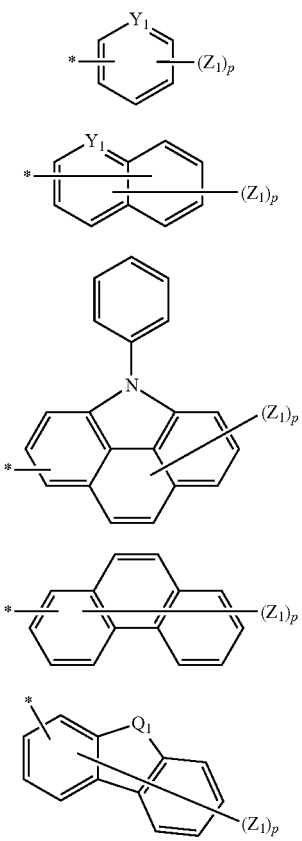

wherein, in Formulas 2a to 2e, $Q_1$ is a group represented by —C($R_{30}$)($R_{31}$)—, —N($R_{32}$)—, —S—, or —O—;

$Y_1$ is CH or N;

$Z_1$, $R_{30}$, $R_{31}$, and $R_{32}$ are each independently a hydrogen atom, a deuterium atom, a substituted or unsubstituted $C_1$-$C_{20}$ alkyl group, a substituted or unsubstituted $C_6$-$C_{20}$ aryl group, a substituted or unsubstituted $C_3$-$C_{20}$ heteroaryl group, a substituted or unsubstituted $C_6$-$C_{20}$ condensed polycyclic group, —Si($R_{40}$)$_3$, a halogen atom, a cyano group, a nitro group, a hydroxyl group, or a carboxyl group;

$R_{40}$ is a substituted or unsubstituted $C_1$-$C_{20}$ alkyl group, a substituted or unsubstituted $C_6$-$C_{20}$ aryl group, a substituted or unsubstituted $C_3$-$C_{20}$ heteroaryl group, or a substituted or unsubstituted $C_6$-$C_{20}$ condensed polycyclic group;

p is an integer from 1 to 9; and

* is a binding site.

3. The compound of claim 1, wherein $Ar_3$ is represented by Formula 3a or Formula 3b below:

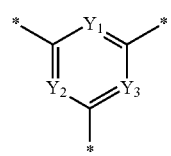

3a

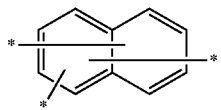

3b wherein, in Formulas 3a and 3b, $Y_1$, $Y_2$, and $Y_3$ are each independently CH or N, and

* is a binding site.

4. The compound of claim 1, wherein $Ar_4$ is one of the following compounds represented by Formulas 4a to 4f:

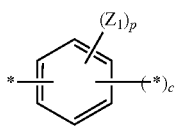

4a

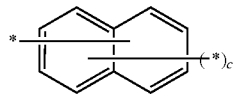

4b

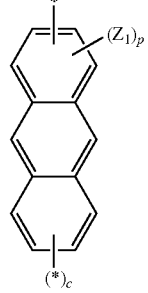

4c

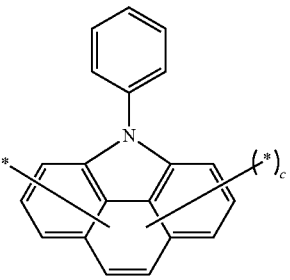

4d

-continued

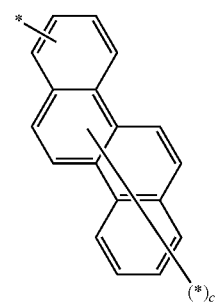
4e

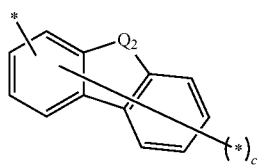
4f wherein, in Formulas 4a to 4f, $Q_2$ is a group represented by —$C(R_{30})(R_{31})$—;

$Z_1$, $R_{30}$, and $R_{31}$ are each independently a hydrogen atom, a deuterium atom, a substituted or unsubstituted $C_1$-$C_{20}$ alkyl group, a substituted or unsubstituted $C_6$-$C_{20}$ aryl group, a substituted or unsubstituted $C_3$-$C_{20}$ heteroaryl group, a substituted or unsubstituted $C_6$-$C_{20}$ condensed polycyclic group, a halogen atom, a cyano group, a nitro group, a hydroxyl group, or a carboxyl group;

p is an integer from 1 to 9;

c is an integer from 1 to 3; and

* is a binding site.

5. The compound of claim 1, wherein the compound of Formula 1 above is one of the following compounds below:

3

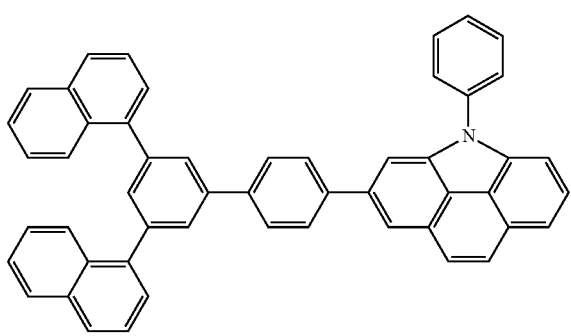

21

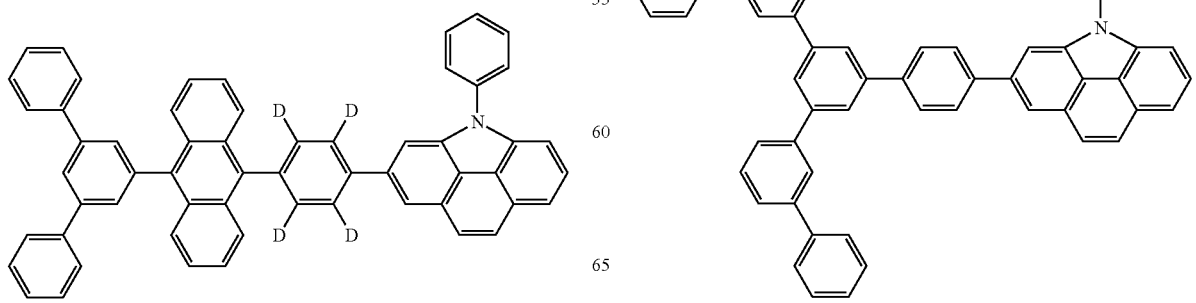

-continued

24

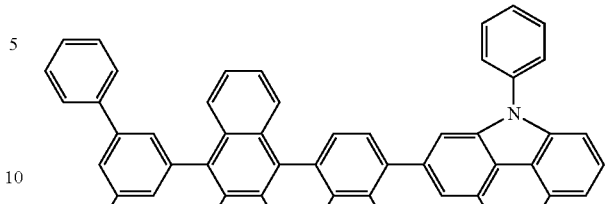

27

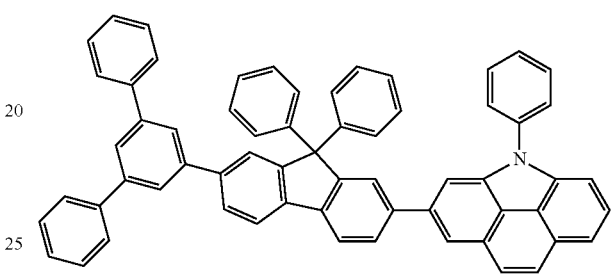

40

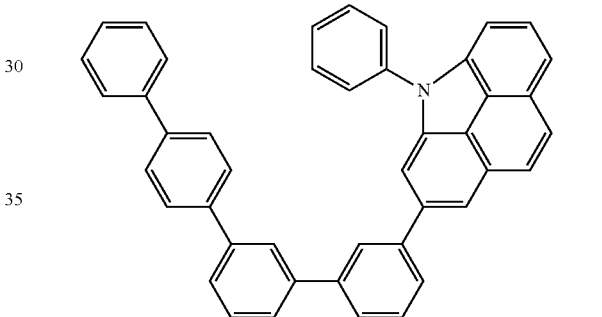

44

-continued

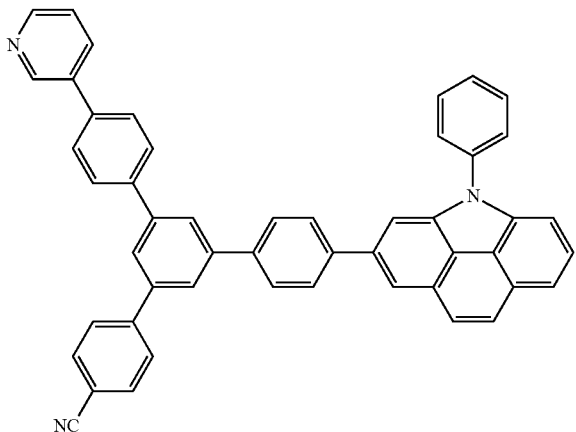

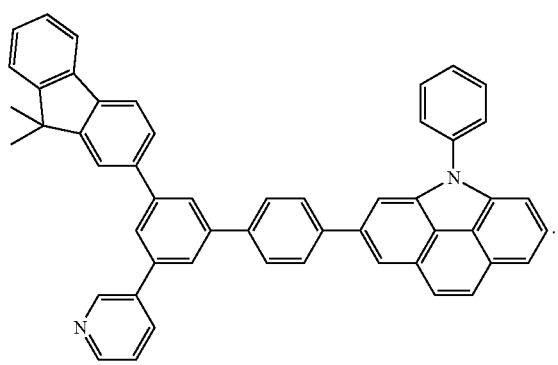

6. An organic light-emitting diode (OLED), comprising:
a first electrode;
a second electrode; and
an organic layer that is disposed between the first electrode and the second electrode, and includes the compound of claim 1.

7. The OLED of claim 6, wherein the organic layer is a blue emission layer or an electron transport layer.

8. The OLED of claim 6, comprising a hole injection layer, a hole transport layer, or a functional layer having both hole injection and hole transport capabilities, and
an emission layer that includes the compound of claim 1, the emission layer further including an anthracene-based compound, an arylamine-based compound, or a styryl-based compound.

9. The OLED of claim 6 comprising a hole injection layer, a hole transport layer, or a functional layer having both hole injection and hole transport capabilities, and
an emission layer that includes the compound of claim 1, wherein at least one of a red emission layer, a green emission layer, a blue emission layer, and a white emission layer of the emission layer includes a phosphorescent compound.

10. The OLED of claim 9, wherein the hole injection layer, the hole transport layer, or the functional layer having both hole injection and hole transport capabilities includes a charge-generating material.

11. The OLED of claim 10, wherein the charge-generating material is a p-dopant.

12. The OLED of claim 11, wherein the p-dopant is a quinone derivative.

13. The OLED of claim 11, wherein the p-dopant is a metal oxide.

14. The OLED of claim 11, wherein the p-dopant is a cyano group-containing compound.

15. The OLED of claim 6, wherein the organic layer includes an electron transport layer, and the electron transport layer includes an electron-transporting organic compound and a metal complex.

16. The OLED of claim 15, wherein the metal complex is a lithium complex.

17. The OLED of claim 15, wherein the metal complex is lithium quinolate or Compound 203:

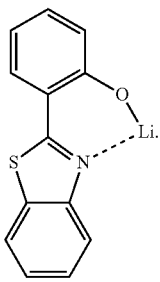

<Compound 203>

18. The OLED of claim 6, wherein the organic layer is formed of the compound of claim 1 by using a wet process.

19. A flat panel display device comprising the OLED of claim 6,
wherein the first electrode of the OLED is electrically connected to a source electrode or a drain electrode in a thin film transistor.

* * * * *